US011591599B2

(12) United States Patent
Gomis et al.

(10) Patent No.: US 11,591,599 B2
(45) Date of Patent: Feb. 28, 2023

(54) METHOD FOR THE DIAGNOSIS, PROGNOSIS AND TREATMENT OF CANCER METASTASIS

(71) Applicants: Fundació Institut de Recerca Biomèdica (IRB Barcelona), Barcelona (ES); Institució Catalana de Recerca I Estudis Avançats, Barcelona (ES)

(72) Inventors: Roger Gomis, Barcelona (ES); Anna Arnal, Barcelona (ES); Maria Tarragona, Barcelona (ES); Milica Pavlovic, Lajkovac (RS); Evarist Planet, Barcelona (ES)

(73) Assignees: Fundació Institut de Recerca Biomèdica (IRB Barcelona), Barcelona (ES); Institució Catalana de Recerca i Estudis Avançais, Barcelona (ES)

( * ) Notice: Subject to any disclaimer, the term of this patent is extended or adjusted under 35 U.S.C. 154(b) by 272 days.

(21) Appl. No.: 15/944,499

(22) Filed: Apr. 3, 2018

(65) Prior Publication Data

US 2019/0309299 A1 Oct. 10, 2019

Related U.S. Application Data

(63) Continuation of application No. 14/776,453, filed as application No. PCT/IB2014/001128 on Mar. 14, 2014, now abandoned.

(30) Foreign Application Priority Data

Mar. 15, 2013 (ES) ................. ES201330384

(51) Int. Cl.
*C12N 15/113* (2010.01)
*C12Q 1/6886* (2018.01)
*C07K 16/32* (2006.01)
*A61K 38/17* (2006.01)

(52) U.S. Cl.
CPC .......... *C12N 15/1135* (2013.01); *A61K 38/17* (2013.01); *C07K 16/32* (2013.01); *C12Q 1/6886* (2013.01); *C12N 2310/11* (2013.01); *C12N 2310/14* (2013.01); *C12N 2320/30* (2013.01); *C12Q 2600/118* (2013.01); *C12Q 2600/158* (2013.01); *Y10T 436/143333* (2015.01)

(58) Field of Classification Search
CPC ............ C12N 15/1135; C12N 2310/11; C12N 2310/14; C12N 2320/30; A61K 38/017; C07K 16/32; C12Q 1/6886; C12Q 2600/118; C12Q 2600/158; Y10T 436/143333
See application file for complete search history.

(56) References Cited

U.S. PATENT DOCUMENTS

| 5,093,246 | A | 3/1992 | Cech et al. |
|---|---|---|---|
| 5,176,996 | A | 1/1993 | Hogan et al. |
| 5,256,775 | A | 10/1993 | Froehler |
| 5,264,564 | A | 11/1993 | Matteucci |
| 5,527,772 | A | 6/1996 | Holick |
| 5,958,671 | A | 9/1999 | Glimcher et al. |
| 6,090,367 | A | 7/2000 | Khalil |
| 6,274,338 | B1 | 8/2001 | Glimcher et al. |
| 6,287,813 | B1 | 9/2001 | Fussenegger et al. |
| 6,362,163 | B1 | 3/2002 | Gardella et al. |
| 7,863,269 | B2 | 1/2011 | Heinelt et al. |
| 9,702,878 | B2 | 7/2017 | Gomis et al. |
| 10,006,091 | B2 | 6/2018 | Gomis et al. |
| 10,047,398 | B2 | 8/2018 | Gomis et al. |
| 10,114,022 | B2 | 10/2018 | Gomis et al. |
| 10,119,171 | B2 | 11/2018 | Gomis et al. |
| 10,793,642 | B2 | 10/2020 | Gomis et al. |
| 10,866,241 | B2 | 12/2020 | Gomis et al. |
| 11,041,213 | B2 | 6/2021 | Gomis et al. |
| 11,041,861 | B2 | 6/2021 | Gomis et al. |

(Continued)

FOREIGN PATENT DOCUMENTS

| AU | 2011311452 B2 * | 4/2012 | ....... G01N 33/57415 |
|---|---|---|---|
| EP | 1961825 A1 | 8/2008 | |

(Continued)

OTHER PUBLICATIONS

Rudikoff et al., Single amino acid substitution altering antigen-binding specificity, Proc. Natl. Acad. Sci. USA, 1982,79:1979-1983 (Year: 1982).*

Riemer et. al., Matching of trastuzumab (Herceptin) epitope mimics onto the surface of Her-2/neu—a new method of epitope definition, Molecular Immunology, 2005, 42:1121-1124, Publication Date: Jan. 8, 2005 (Year: 2005).*

Almagro et al. Humanization of antibodies, Frontiers in Bioscience, 2008 13:1619-1633, Publication Date: Jan. 1, 2008 (Year: 2008).*

Uray et al., Estradiol down-regulates CD36 expression in human breast cancer cells, Cancer Letters, 2004, 207:101-107, Publication Date: Dec. 23, 2003 (Year: 2003).*

(Continued)

*Primary Examiner* — Peter J Reddig
*Assistant Examiner* — Cheng Lu
(74) *Attorney, Agent, or Firm* — Sterne, Kessler, Goldstein & Fox P.L.L.C.

(57) ABSTRACT

This study describes a method to determine the likelihood of the development of metastasis in a subject suffering from cancer, in addition to a method to design a customized therapy in a subject suffering from cancer, in particular breast, colon, lung, kidney and thyroid cancer, based on the determination of the expression level of one or more genes whose expression is modulated by an increase in c-MAF expression. It also describes a method for the identification of marker genes with a propensity for metastatic cancer based on inducing the modulation of the c-MAF expression Finally, the use of PTHLH and PODXL inhibitors and RERG activators in the treatment and/or prevention of the cancer, in particular breast, colon, lung, kidney and thyroid cancer.

8 Claims, 16 Drawing Sheets

Specification includes a Sequence Listing.

(56) References Cited

U.S. PATENT DOCUMENTS

| | | |
|---|---|---|
| 11,072,831 B2 | 7/2021 | Gomis et al. |
| 2004/0132086 A1 | 7/2004 | Horwitz et al. |
| 2005/0181375 A1 | 8/2005 | Aziz et al. |
| 2007/0010469 A1 | 1/2007 | Chan et al. |
| 2007/0203071 A1 | 8/2007 | Gardella et al. |
| 2009/0048117 A1 | 2/2009 | Glimcher et al. |
| 2011/0152113 A1 | 6/2011 | Escudero et al. |
| 2012/0195890 A1* | 8/2012 | Cabon ............... A61P 43/00 424/133.1 |
| 2014/0057796 A1 | 2/2014 | Gomis et al. |
| 2014/0105918 A1 | 4/2014 | Gomis et al. |
| 2014/0162887 A1 | 6/2014 | Martin et al. |
| 2014/0314792 A1 | 10/2014 | Gomis et al. |
| 2015/0152506 A1 | 6/2015 | Gomis et al. |
| 2015/0293100 A1 | 10/2015 | Gomis et al. |
| 2015/0362495 A1 | 12/2015 | Gomis et al. |
| 2016/0032399 A1 | 2/2016 | Gomis et al. |
| 2016/0032400 A1 | 2/2016 | Gomis et al. |
| 2016/0040247 A1 | 2/2016 | Gomis et al. |
| 2017/0002357 A1 | 1/2017 | Gomis et al. |
| 2017/0101683 A1 | 4/2017 | Gomis et al. |
| 2017/0121777 A1 | 5/2017 | Gomis et al. |
| 2017/0298130 A1 | 10/2017 | Henriksen et al. |
| 2017/0369589 A1 | 12/2017 | Gomis et al. |
| 2017/0370935 A1 | 12/2017 | Gomis et al. |
| 2019/0119757 A1 | 4/2019 | Gomis et al. |
| 2019/0169693 A1 | 6/2019 | Gomis et al. |
| 2019/0242898 A1 | 8/2019 | Gomis et al. |
| 2019/0256922 A1 | 8/2019 | Gomis et al. |
| 2019/0269707 A1 | 9/2019 | Gomis et al. |
| 2021/0137952 A1 | 5/2021 | Gregory et al. |
| 2021/0190784 A1 | 6/2021 | Gomis et al. |
| 2021/0317534 A1 | 10/2021 | Gomis et al. |

FOREIGN PATENT DOCUMENTS

| | | |
|---|---|---|
| EP | 2412825 A1 | 2/2012 |
| KR | 20070016092 A | 2/2007 |
| WO | WO-8604920 A1 | 8/1986 |
| WO | WO-8809810 A1 | 12/1988 |
| WO | WO-8910134 A1 | 11/1989 |
| WO | WO-9509853 A1 | 4/1995 |
| WO | WO-9738117 A1 | 10/1997 |
| WO | WO-0175171 A2 | 10/2001 |
| WO | WO-03027275 A1 | 4/2003 |
| WO | WO-03059249 A2 | 7/2003 |
| WO | WO-2004060386 A1 | 7/2004 |
| WO | WO-2004103273 A2 | 12/2004 |
| WO | WO-2005026322 A2 | 3/2005 |
| WO | WO-2005046731 A1 | 5/2005 |
| WO | WO-2005063252 A1 | 7/2005 |
| WO | WO-2006012221 A2 | 2/2006 |
| WO | WO-2006135436 A2 | 12/2006 |
| WO | WO-2007045996 A1 | 4/2007 |
| WO | WO-2007069090 A2 | 6/2007 |
| WO | WO-2008014888 A2 | 2/2008 |
| WO | WO-2008086800 A2 | 7/2008 |
| WO | WO-2008098351 A1 | 8/2008 |
| WO | WO-2008133766 A1 | 11/2008 |
| WO | WO-2009049410 A1 | 4/2009 |
| WO | WO-2009146546 A1 | 12/2009 |
| WO | WO-2010000907 A1 | 1/2010 |
| WO | WO-2010003773 A1 | 1/2010 |
| WO | WO-2011003935 A1 | 1/2011 |
| WO | WO-2011039734 A2 | 4/2011 |
| WO | WO-2012045905 A2 | 4/2012 |
| WO | WO-2013153458 A2 | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2015193737 A1 | 12/2015 |
| WO | WO-2016092524 A1 | 6/2016 |
| WO | WO-2017203468 A1 | 11/2017 |
| WO | WO-2019102380 A1 | 5/2019 |

OTHER PUBLICATIONS

DeFilippis et al., CD36 repression activates a multicellular stromal program shared by high mammographic density and tumor tissues, Cancer Discovery, 2012, 2(9):826-839, Publication Date: Jul. 9, 2012 (Year: 2012).*

Clezardin et al. Expression of Thrombospondin (TSP1) and its receptors (CD36 and CD51) in normal, hyperplastic, and neoplastic human breast, Cancer Reseach, 1993, (53) 1421-1430, Publication Date: Mar. 15, 1993 (Year: 1993).*

Scott et al., Antibody therapy of cancer, Nature Review Cancer, 12, 278-287 (Year: 2012).*

Cohen-Dvashi, H., et al., "Navigator-3, a Modulator of Cell Migration, May Act as a Suppressor of Breast Cancer Progression," EMBO Molecular Medicine 7(3):299-314, Wiley-Blackwell, England (2015).

Dhesy-Thind, S., et al., "Use of Adjuvant Bisphosphonates and Other Bone-Modifying Agents in Breast Cancer: A Cancer Care Ontario and American Society of Clinical Oncology Clinical Practice Guideline," J Clin Oncol 35, American Society of Clinical Oncology, United States, 22 pages (published online before print Mar. 6, 2017).

Hurt, E.M., et al., "Overexpression of c-maf is a Frequent Oncogenic Event in Multiple Myeloma that Promotes Proliferation and Pathological Interactions with Bone Marrow Stroma," Cancer Cell 5(2):191-199, Cell Press, United States (Feb. 2004).

Khaled, W.T., et al., "BCL11A is a Triple-Negative Breast Cancer Gene with Critical Functions in Stem and Progenitor Cells," Nature Communications 6:5987, 10 pages, Macmillan Publishers Limited, London (2015).

Porcs-Makkay, M. et al., "New Practical Synthesis of Tenidap," Organic Process Research & Development 4:10-16, ACS Publications (2000).

Co-Pending U.S. Appl. No. 16/766,043, Int'l Filing Date Nov. 21, 2018, inventor Gregory: Walter Martin, et al. (Unpublished).

Koch., et al., "CD36-Mediated Activation of Endothelial Cell Apoptosis by an N-Terminal Recombinant Fragment of Thrombospondin-2 Inhibits Breast Cancer Growth and Metastasis In Vivo," Breast Cancer Research and Treatment, 128(2):337-346, Kluwer Academic, Netherlands (Jul. 2011).

Abe, M., et al., "Characterization of Cis-acting Elements Regulating Transcription of the Human Df3 Breast Carcinoma-associated Antigen (Muc1) Gene," Proceedings of the National Academy of Sciences of the United States of America 90(1):282-286, National Academy of Sciences, United States (Jan. 1993).

Akiyama, T., et al., "G1 Phase Accumulation Induced by Ucn-01 Is Associated With Dephosphorylation of Rb and Cdk2 Proteins as Well as Induction of Cdk Inhibitor P21/cip1/waf1/sdi1 in P53-mutated Human Epidermoid Carcinoma A431 Cells," Cancer Research 57(8):1495-1501, American Association for Cancer Research, United States (Apr. 1997).

Altschul, S.F., et al., "Basic Local Alignment Search Tool," Journal of Molecular Biology 215(3):403-410, Elsevier, England (Oct. 1990).

Andrews, N.C., et al., "The Ubiquitous Subunit of Erythroid Transcription Factor NF-E2 is a Small Basic-leucine Zipper Protein Related to the v-maf Oncogene," Proceedings of the National Academy of Sciences of USA 90(24):11488-11492, National Academy of Sciences, United States (1993).

Arris, C.E., et al., "Identification of Novel Purine and Pyrimidine Cyclin-dependent Kinase Inhibitors With Distinct Molecular Interactions and Tumor Cell Growth Inhibition Profiles," Journal of Medicinal Chemistry 43(15):2797-2804, American Chemical Society, United States (Jul. 2000).

Attaby, F.A., et al., "Synthesis of Pyrimidine, Thiazolopyrimidine, Pyrimidotriazine and Triazolopyrimidine Derivatives and their Biological Evaluation," Journal of Natural Science, 54b:788-798, (1999).

(56) References Cited

OTHER PUBLICATIONS

Co-pending Application, U.S. Appl. No. 16/303,945, inventor Gregory, Walter Martin., filed Nov. 21, 2018 (Not yet Published).
Barvian, M., et al., "Pyrido[2,3-d]pyrimidin-7-one Inhibitors of Cyclin-dependent Kinases," Journal of Medicinal Chemistry 43(24):4606-4616, American Chemical Society, United States (Nov. 2000).
Basset, P., et al., "A Novel Metalloproteinase Gene Specifically Expressed in Stromal Cells of Breast Carcinomas," Nature 348(6303):699-704, Nature Publishing Group, England (Dec. 1990).
Begemann, M., et al., "Treatment of Human Glioblastoma Cells With the Staurosporine Derivative Cgp 41251 Inhibits Cdc2 and Cdk2 Kinase Activity and Increases Radiation Sensitivity," Anticancer Research 18(4A):2275-2282, International Institute of Anticancer Research, Greece (Jul.-Aug. 1998).
Co-pending Application, U.S. Appl. No. 16/142,168, inventor Gomis, R., et al., filed Sep. 26, 2018 (Not yet Published).
Bos, P.D., et al., "Genes that Mediate Breast Cancer Metastasis to the Brain," Nature 459(7249):1005-1009, Nature Publishing Group, England (2009).
Brooks, E.E., et al., "CVT-313, a Specific and Potent Inhibitor of Cdk2 That Prevents Neointimal Proliferation," Journal of Biological Chemistry 272(46):29207-29211, American Society for Biochemistry and Molecular Biology, United States (Nov. 1997).
Byrns, M.C. and Penning, T.M., "Type 5 17 beta-Hydroxysteroid Dehydrogenase/Prostaglandin F Synthase (AKR1C3): Role in Breast Cancer and Inhibition by Nonsteroidal Antiinflammatory Drug Analogs," Chemico-Biological Interactions 178(1-3): 221-227, Elsevier, Ireland (Mar. 2009).
Cao, S., et al., "The Protooncogene C-Maf is an Essential Transcription Factor for IL-10 Gene Expression in Macrophages," Immunology 174(6):3484-3492, American Association of Immunologists, United States (Mar. 2005).
Carlson, B.A., et al., "Flavopiridol Induces G1 Arrest With Inhibition of Cyclin-dependent Kinase (Cdk) 2 and Cdk4 in Human Breast Carcinoma Cells," Cancer Research 56(13):2973-2978, American Association for Cancer Research, United States (Jul. 1996).
Chang, Y.T., et al., "Synthesis and Application of Functionally Diverse 2,6,9-trisubstituted Purine Libraries as Cdk Inhibitors," Chemical biology 6(6):361-375, Elsevier, United States (Jun. 1999).
Christopherson, K.S., et al., "Ecdysteroid-dependent Regulation of Genes in Mammalian Cells by a Drosophila Ecdysone Receptor and Chimeric Transactivators," Proceedings of the National Academy of Sciences of the United States of America 89(14):6314-6318, National Academy of Sciences, United States (1992).
Clinicaltrials.gov, "An Investigational Drug (CAL) Versus Zoledronic Acid (Zometa®) in Patients With Breast Cancer," Accession No. NCT, accessed at https://clinicaltrials.gov/ct2/show/NCT00051779, accessed on Mar. 28, 2016.
Co-pending Application, U.S. Appl. No. 16/028,530, inventor Gomis, R., et al., filed Jul. 6, 2018 (Not yet Published).
Co-pending Application, U.S. Appl. No. 16/369,586, inventor Gregory, W., et al., filed Nov. 21, 2018 (Not yet Published).
Co-pending Application, U.S. Appl. No. 15/944,510, inventors Gomis R., et al., filed Apr. 3, 2018 (Not yet Published).
Co-pending Application, U.S. Appl. No. 15/955,790, Inventors Gomis, R., et al., filed Apr. 18, 2018 (Not yet Published).
Davies, T.G., et al., "Inhibitor Binding to Active and Inactive Cdk2: the Crystal Structure of Cdk2-cyclin a/indirubin-5-sulphonate," Structure 9(5):389-397, Cell Press, United States (May 2001).
Davies, T.G., et al., "Structure-based Design of a Potent Purine-based Cyclin-dependent Kinase Inhibitor," Nature Structural & Molecular Biology 9(10):745-749, Nature Publishing, United States (Oct. 2002).
Davis, S.T., et al., "Prevention of Chemotherapy-induced Alopecia in Rats by Cdk Inhibitors," Science 291(5501):134-137, American Association for the Advancement of Science, United States (Jan. 2001).
Doppelt, S.H., et al., "Inhibition of the in Vivo Parathyroid Hormone-mediated Calcemic Response in Rats by a Synthetic Hormone Antagonist," Proceedings of the National Academy of Sciences of the United States of America 83(19):7557-7560, National Academy of Sciences, United States (Oct. 1986).
Co-pending Application, U.S. Appl. No. 15/984,629, inventor Gomis, R., et al., filed May 21, 2018 (Not yet Published).
Dreyer, M.K., et al., "Crystal Structure of Human Cyclin-dependent Kinase 2 in Complex With the Adenine-derived Inhibitor H717," Journal of Medicinal Chemistry 44(4):524-530, American Chemical Society, United States (Feb. 2001).
Egholm, M., et al., "PNA Hybridizes to Complementary Oligo-nucleotides Obeying the Watson-crick Hydrogen-bonding Rules," Nature 365(6446):566-568, Nature Publishing Group, England (Oct. 1993).
Extended European Search Report for EP Application No. EP17181286, Munich Germany, dated Mar. 8, 2018, 27 pages.
Eychene, A., et al., "A New MAFia in Cancer," Nature Reviews Cancer 8(9):683-693, Nature Publishing Group, England (2008).
Fabbro, D., et al., "Inhibitors of Protein Kinases: Cgp 41251, a Protein Kinase Inhibitor With Potential as an Anticancer Agent," Pharmacology & Therapeutics 82(2-3):293-301, Pergamon Press, England (May-Jun. 1999).
Fujiwara, K.T., et al., "Two New Members of the maf Oncogene Family, mafK and mafF, Encode Nuclear b-Zip Proteins Lacking Putative Trans-Activator Domain," Oncogene 8(9):2371-2380, Nature Publishing Group, England (1993).
Ghoussaini, M., et al., "Genome-Wide Association Analysis Identifies Three New Breast Cancer Susceptibility Loci," Nature Genetics 44(3):312-318, Nature Pub, United States (Jan. 2012).
Gossen, M. and Bujard, H., "Tight Control of Gene Expression in Mammalian Cells by Tetracycline-responsive Promoters," Proceedings of the National Academy of Sciences of the United States of America 89(12):5547-5551, National Academy of Sciences, United States (1992).
Gossen, M., et al., "Transcriptional Activation by Tetracyclines in Mammalian Cells," Science 268(5218):1766-1769, American Association for the Advancement of Science, United States (Jun. 1995).
Gray, N.S., et al., "Exploiting Chemical Libraries, Structure, and Genomics in the Search for Kinase Inhibitors," Science 281(5376):533-538, American Association for the Advancement of Science, United States (Jul. 1998).
Habashy, H.O., et al., "RERG (Ras-Like, Oestrogen-Regulated, Growth-Inhibitor) Expression in Breast Cancer: A Marker of Er-Positive Luminal-Like Subtype," Breast Cancer Research and Treatment 128(2):315-326, Kluwer Academic, Netherlands (Jul. 2011).
Hammond, M.E.H., et al., "American Society of Clinical Oncology/College of American Pathologists Guideline Recommendations for Immunohistochemical Testing of Estrogen and Progesterone Receptors in Breast Cancer," Journal of Clinical Oncology 28(16):2784-2795, American Society of Clinical Oncology, United States (2010).
Helene, C., "The Anti-gene Strategy: Control of Gene Expression by Triplex-forming-oligonucleotides," Anti-cancer Drug Design 6(6):569-584, Oxford University Press, United States (1991).
Hideshima, T., et al., "Understanding Multiple Myeloma Pathogenesis in the Bone Marrow to Identify New Therapeutic Targets," Nature Reviews. Cancer 7(8):585-598, Nature Pub. Group, England (Aug. 2007).
Hoare, S.R., et al., "Specificity and Stability of a New Pth1 Receptor Antagonist, Mouse Tip(7-39)," Peptides 23(5):989-998, Elsevier Science Inc, United States (May 2002).
Hoessel, R., et al., "Indirubin, the active constituent of a Chinese antileukaemia medicine, inhibits cyclin-dependent kinases," Nature Cell Biology 1:60-67, Nature Publishing (1999).
Honma, T., et al., "A Novel Approach for the Development of Selective Cdk4 Inhibitors: Library Design Based on Locations of Cdk4 Specific Amino Acid Residues," Journal of Medicinal Chemistry 44(26):4628-4640, American Chemical Society, United States (Dec. 2001).
Honma, T., et al., "Structure-based Generation of a New Class of Potent Cdk4 Inhibitors: New De Novo Design Strategy and Library Design," Journal of Medicinal Chemistry 44(26):4615-4627, American Chemical Society, United States (Dec. 2001).
Igarashi, K., et al., "Activity and Expression of Murine Small Maf Family Protein MafK," The Journal of Biological Chemistry

(56) References Cited

OTHER PUBLICATIONS

270(13):7615-7624, The American Society for Biochemistry and Molecular Biology, Inc., United States (1995).
Imbach, P., et al., "2,6,9-trisubsistuted purines: optimization towards highly potent and selective CDK1 inhibitors" Bioorganic & Medicinal Chemistry Letters 9:91-96, Elsevier, Netherlands (Jan. 1999).
International Preliminary Report on Patentability for International Application No. PCT/IB2014/001128, European Patent Office, Rijswijk, dated Sep. 15, 2015, 12 pages.
International Search Report and Written Opinion for International Application No. PCT/IB2014/001128, European Patent Office, Rijswijk, dated Mar. 2, 2015, 13 pages.
Kataoka, K., et al., "Small Maf Proteins Heterodimerize with Fos and May Act as Competitive Repressors of the NF-E2 Transcription Factor," Molecular and Cellular Biology 15(4):2180-2190, American Society for Microbiology, United States (1995).
Kataoka, K., et al., "Transactivation Activity of Maf Nuclear Oncoprotein is Modulated by Jun, Fos and Small Maf Proteins," Oncogene 12:53-62, Stockton Press, England (1996).
Kataoka, K., "Multiple Mechanisms and Functions of maf Transcription Factors in the Regulation of Tissue-specific Genes," Journal of Biochemistry 141(6):775-781, Oxford University Press, England (Jun. 2007).
Kawakami, K., et al., "UCN-01,7-Hydroxyl-staurosporine, Inhibits Kinase Activity of Cyclin-dependent Kinases and Reduces the Phosphorylation of the Retinoblastoma Susceptibility Gene Product in A549 Human Lung Cancer Cell Line," Biochemical and Biophysical Research Communications 219(3):778-783, Elsevier, United States (Feb. 1996).
Kaykas, A. and Moon, R.T., "A plasmid-based system forexpressing small interfering RNA libraries in mammalian cells," BMC Cell Biology 5:1-11, BioMed Central Ltd., England (2004).
Kitagawa, M., et al., "Butyrolactone I, a Selective Inhibitor of Cdk2 and Cdc2 Kinase," Oncogene 8(9):2425-2432, Nature Publishing Group, England (Sep. 1993).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kurschner, C., et al., "The maf Proto-Oncogene Stimulates Transcription from Multiple Sites in a Promoter That Directs Purkinje Neuron-Specific Gene Expression," Molecular and Cellular Biology 15(1):246-254, American Society for Microbiology, United States (Jan. 1995).
Lee, N.S., et al., "Expression of small interfering RNAs targeted against HIV-1 rev transcripts in human cells," Nature Biotechnology 20(5):500-505, Nature American Publishing, United States (2002).
Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).
Letsinger, R.L., et al., "Cholesteryl-conjugated Oligonucleotides: Synthesis, Properties, and activity as Inhibitors of Replication of Human Immunodeficiency Virus in Cell Culture," Proceedings of the National Academy of Sciences USA 86(17):6553-6556, National Academy of Science, United States (Sep. 1989).
Lewis, M.J., et al., "Expression of Progesterone Metabolizing Enzyme Genes (AKR1C1, AKR1C2, AKR1C3, SRD5A1, SRD5A2) Is Altered in Human Breast Carcinoma," BMC cancer 4(1): 27, BioMed Central, England (Jun. 2004).
Lindgren, M., et al., "Cell-penetrating Peptides," Trends in Pharmacological Sciences 21(3):99-103, Elsevier, England (2000).
Lundberg, M., et al., "Cell Surface Adherence and Endocytosis of Protein Transduction Domains," Molecular Therapy 8(1):143-150, Academic Press, United States (2003).
Makkay, M.P., et al., "Synthesis of 1,3-di[alkoxy(Aryloxy)carbonyl]-2-Oxo-2,3-Dihydroindoles," Tetrahedron 56(32):5893-5903, (Aug. 2000).

Marko, D., et al., "Inhibition of Cyclin-dependent Kinase 1 (Cdk1) by Indirubin Derivatives in Human Tumour Cells," British Journal of Cancer 84(2):283-289, Nature Publishing Group on behalf of Cancer Research UK, England (Jan. 2001).
Mcclue, S.J., et al., "In Vitro and in Vivo Antitumor Properties of the Cyclin Dependent Kinase Inhibitor Cyc202 (R-roscovitine)," International Journal of Cancer 102(5):463-468, Wiley-Liss, United States (Dec. 2002).
Meijer, L., et al., "Biochemical and Cellular Effects of Roscovitine, a Potent and Selective Inhibitor of the Cyclin-dependent Kinases Cdc2, Cdk2 and Cdk5," European Journal of Biochemistry 243(1-2):527-536, Blackwell Science Ltd. on behalf of the Federation of European Biochemical Societies, England (Jan. 1997).
Meijer, L, et al., "Inhibition of cyclin-dependent kinases, GSK-3beta and CK1 by hymenialdisine, a marine sponge constituent," Chemistry and Biology 7(1):51-63, 1999.
Mettey, Y., et al., "Aloisines, a New Family of Cdk/gsk-3 Inhibitors. Sar Study, Crystal Structure in Complex With Cdk2, Enzyme Selectivity, and Cellular Effects," Journal of Medicinal Chemistry 46(2):222-236, American Chemical Society, United States (Jan. 2003).
GenBank database NCBI Reference Sequence AAA60360.1 form A, accessed at https://www.ncbi.nlm.nih.gov/protein/AAA60360.1, accessed on Jul. 30, 2018, 1 page.
GenBank database NCBI Reference Sequence AAA60358.1 form B accessed at https://www.ncbi.nlm.nih.gov/protein/AAA60358.1, accessed on Aug. 20, 2018, 1 page.
GenBank database NCBI Reference Sequence AAA60359.1 form C accessed at https://www.ncbi.nlm.nih.gov/protein/AAA60359.1, accessed on Aug. 20, 2018, 1 page.
GenBank database NCBI Reference Sequence NM_001018111.2 variant 1 accessed at https://www.ncbi.nlm.nih.gov/nuccore/NM_001018111.2, accessed on Jul. 30, 2018, 6 pages.
GenBank database NCBI Reference Sequence NM_005397.3 variant 2 accessed at https://www.ncbi.nlm.nih.gov/nuccore/NM_005397.3, accessed on Aug. 20, 2018, 5 pages.
GenBank database NCBI Reference Sequence NP_001018121.1 isoform 1 accessed at https://www.ncbi.nlm.nih.gov/protein/NP_001018121.1, accessed on Jul. 30, 2018, 3 pages.
GenBank database NCBI Reference Sequence NP_005388.2 isoform 2 accessed at https://www.ncbi.nlm.nih.gov/protein/NP_005388.2, accessed on Aug. 20, 2018, 3 pages.
GenBank database NCBI Reference Sequence NM_198965.1 variant 1 accessed at https://www.ncbi.nlm.nih.gov/nuccore/NM_198965.1, accessed on Jul. 30, 2018, 4 pages.
GenBank database NCBI Reference Sequence NM_002820.2 variant 2 accessed at https://www.ncbi.nlm.nih.gov/nuccore/NM_002820.2, accessed on Aug. 20, 2018, 4 pages.
GenBank database NCBI Reference Sequence NM_198964.1 variant 3 accessed at https://www.ncbi.nlm.nih.gov/nuccore/NM_198964.1, accessed on Aug. 20, 2018, 4 pages.
GenBank database NCBI Reference Sequence NM_198966.1 variant 4 accessed at https://www.ncbi.nlm.nih.gov/nuccore/NM_198966.1, accessed on Aug. 20, 2018, 4 pages.
GenBank database NCBI Reference Sequence NP_116307 isoform 1 accessed at https://www.ncbi.nlm.nih.gov/protein/NP_116307, accessed on Jul. 30, 2018, 3 pages.
GenBank database NCBI Reference Sequence NP_001177655 isoform 2 accessed at https://www.ncbi.nlm.nih.gov/protein/NP_001177655, accessed on Aug. 20, 2018, 3 pages.
GenBank database NCBI Reference Sequence NM_032918.2 variant 1 accessed at https://www.ncbi.nlm.nih.gov/nuccore/NM_032918.2, accessed on Jul. 30, 2018, 3 pages.
GenBank database NCBI Reference Sequence NM_001190726.1 variant 2 accessed at https://www.ncbi.nlm.nih.gov/nuccore/NM_001190726.1, accessed on Aug. 20, 2018, 3 pages.
GenBank database NCBI Reference Sequence NG_016440 accessed at https://www.ncbi.nlm.nih.gov/nuccore/NG_016440, accessed on Jul. 30, 2018, 5 pages.
GenBank database NCBI Reference Sequence NG_023197 accessed at https://www.ncbi.nlm.nih.gov/nuccore/NG_023197, Mar. 30, 2018, 7 pages.

(56) References Cited

OTHER PUBLICATIONS

GenBank database NCBI Reference Sequence NM_005360.4 accessed at https://www.ncbi.nlm.nih.gov/nuccore/NM_005360.4, accessed on Jul. 30, 2018, 4 pages.
GenBank database NCBI Reference Sequence NM_001031804.2 accessed at https://www.ncbi.nlm.nih.gov/nuccore/NM_001031804.2, accessed on Aug. 20, 2018, 5 pages.
No, D., et al., "Ecdysone-inducible Gene Expression in Mammalian Cells and Transgenic Mice," Proceedings of the National Academy of Sciences USA 93(8):3346-3351, National Academy of Sciences, United States (Apr. 1996).
Nugiel, D.A., et al., "Indenopyrazoles as Novel Cyclin Dependent Kinase (Cdk) Inhibitors," Journal of Medicinal Chemistry 44(9):1334-1336, American Chemical Society, United States (Apr. 2001).
Nugiel, D.A., et al., "Synthesis and Evaluation of Indenopyrazoles as Cyclin-dependent Kinase Inhibitors. 2. Probing the Indeno Ring Substituent Pattern," Journal of Medicinal Chemistry 45(24):5224-5232, American Chemical Society, United States (Nov. 2002).
Nutt, R.F., et al., "Removal of Partial Agonism From Parathyroid Hormone (Pth)-related Protein-(7-34)nh2 by Substitution of Pth Amino Acids at Positions 10 and 11," Endocrinology 127(1):491-493, Oxford University Press, United States (Jul. 1990).
Olstad, O.K., et al., "Expression and Characterization of a Recombinant Human Parathyroid Hormone Partial Agonist With Antagonistic Properties: Gly-hpth(−1→+84)," Peptides 16(6):1031-1037, Elsevier Science Inc, United States (1995).
Peng, S., et al., "C-Maf Increases Apoptosis in Peripheral CD8 Cells by Transactivating Caspase 6," Immunology 127(2):267-278, Blackwell Scientific Publications, England (Jun. 2009).
Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).
Rialet, V., et al., "A New Screening Test for Antimitotic Compounds Using the Universal M Phase-specific Protein Kinase, P34cdc2/cyclin Bcdc13, Affinity-immobilized on P13suc1-coated Microtitration Plates," Anticancer Research 11(4):1581-1590, International Institute of Anticancer Research, Greece (Jul.-Aug. 1991).
Rivera, V.M., et al., "A Humanized System for Pharmacologic Control of Gene Expression," Nature Medicine 2(9):1028-1032, Nature Publishing Company, United States (Sep. 1996).
Rossi, F.M. and Blau, H.M., "Recent Advances in Inducible Gene Expression Systems," Current Opinion in Biotechnology 9(5):451-456, Elsevier, England (1998).
Rossi, J.J., et al., "Practical Ribozymes. Making Ribozymes Work in Cells," Current Biology 4(5):469-471, Cell Press, England (May 1994).
Roubini, E., et al., "Synthesis of Fully Active Biotinylated Analogues of Parathyroid Hormone and Parathyroid Hormone-related Protein as Tools for the Characterization of Parathyroid Hormone Receptors," Biochemistry 31(16):4026-4033, American Chemical Society, United States (Apr. 1992).
Co-pending Application, U.S. Appl. No. 16/134,449, inventor Gomis, R., et al., filed Sep. 18, 2018 (Not yet Published).
Schultz, C., et al., "Paullones, a Series of Cyclin-dependent Kinase Inhibitors: Synthesis, Evaluation of Cdk1/cyclin B Inhibition, and in Vitro Antitumor Activity," Journal of Medicinal Chemistry 42(15):2909-2919, American Chemical Society, United States (Jul. 1999).
Schwarze, S.R. and Dowdy, S.F., "In Vivo Protein Transduction: Intracellular Delivery of Biologically Active Proteins, Compounds and DNA," Trends in Pharmacological Sciences 21(2):45-48, Elsevier, England (2000).
Sielecki, T.M., et al., "Quinazolines as Cyclin Dependent Kinase Inhibitors," Bioorganic & Medicinal Chemistry Letters 11(9):1157-1160, England (May 2001).
Snyder, E.L. and Dowdy, S.F., "Cell Penetrating Peptides in Drug Delivery," Pharmaceutical Research 21(3):389-393, Kluwer Academic/Plenum Publishers, United States (2004).

Somasiri, A., et al., "Overexpression of the Anti-Adhesin Podocalyxin Is an Independent Predictor of Breast Cancer Progression," Cancer Research 64(15):5068-5073, American Association for Cancer Research, United States (Aug. 2004).
Stein, C.A. and Cohen, J.S., "Oligodeoxynucleotides as Inhibitors of Gene Expression: a Review," Cancer Research 48(10):2659-2668, American Association for Cancer Research, United States (1988).
Suhr, S.T., et al., "High Level Transactivation by a Modified Bombyx Ecdysone Receptor in Mammalian Cells Without Exogenous Retinoid X Receptor," Proceedings of the National Academy of Sciences of the United States of America 95(14):7999-8004, National Academy of Sciences, United States (1998).
Templeton, S.N., "Liposomal Delivery of Nucleic Acids in Vivo," DNA and Cell Biology 21(12):857-867, Mary Ann Liebert, United States (2002).
Toogood, P.L., "Cyclin-dependent Kinase Inhibitors for Treating Cancer," Medicinal Research Reviews 21(6):487-498, Wiley, United States (Nov. 2001).
Tran, N., et al., "Expressing functional siRNAs in mammalian cells using convergent transcription," BMC Biotechnology 3:21:1-9, BioMed Central Ltd., England (2003).
Van Der Krol, A.R., et al., "Modulation of Eukaryotic Gene Expression by Complementary RNA or DNA Sequences," Biotechniques 6(10):958-976, Informa Healthcare, United States (Nov. 1988).
Vesely, J., et al., "Inhibition of Cyclin-dependent Kinases by Purine Analogues," European Journal of Biochemistry 224(2):771-786, Blackwell Science Ltd. on behalf of the Federation of European Biochemical Societies, England (Sep. 1994).
Wagner, R.W., "Gene inhibition using antisense oligodeoxynucleotides," Nature 372(6504):333-335, Nature Publishing Group, England (1994).
Wang, D., et al., "Inhibition of Human Immunodeficiency Virus Type 1 Transcription by Chemical Cyclin-dependent Kinase Inhibitors," Journal of Virology 75(16):7266-7279, American Society for Microbiology, ,United States (Aug. 2001).
Wang, J., et al., "Stable and controllable RNA interference: Investigating the physiological function of glutathionylated actin," Proceedings of the National Academy of Sciences of USA 100(9):5103-5106, National Academy of Sciences, United States (2003).
Wang, Q., et al., "Apoptosis in 7-hydroxystaurosporine-treated T Lymphoblasts Correlates With Activation of Cyclin-dependent Kinases 1 and 2," Cell Growth & Differentiation 6(8):927-936, The Association, United States (Aug. 1995).
Wolff, A.C, et al., "American Society of Clinical Oncology/College of American Pathologists Guideline Recommendations for Human Epidermal Growth Factor Receptor 2 Testing in Breast Cancer," Archives of Pathology Laboratory Medicine 131(1):18-43 (2007).
Wolff, A.C., et al., "American Society of Clinical Oncology/college of American Pathologists Guideline Recommendations for Human Epidermal Growth Factor Receptor 2 Testing in Breast Cancer," Journal of Clinical Oncology 25(1):118-145, American Society of Clinical Oncology, United States (Jan. 2007).
Yue, E.W, "Synthesis and Evaluation of Indenopyrazoles as Cyclin-dependent Kinase Inhibitors. 3. Structure Activity Relationships at C3(1,2)," Journal of Medicinal Chemistry 45(24):5233-5248, American Chemical Society, United States (Nov. 2002).
Zaharevitz, D.W., et al., "Discovery and Initial Characterization of the Paullones, a Novel Class of Small-molecule Inhibitors of Cyclin-dependent Kinases," Cancer Research 59(11):2566-2569, American Association for Cancer Research, United States (Jun. 1999).
Zaug, A.J., et al., "A Labile Phosphodiester Bond at the Ligation Junction in a Circular Intervening Sequence RNA," Science 224(4649):574-578, American Association for the Advancement of Science, United States (1984).
Zheng, L., et al., "An approach to genomewide screens of expressed small interfering RNAs in mammalian cells," Proceedings of the National Academy of Sciences of USA 101(1):135-140, National Academy of Sciences, United States (2004).
Zon, G., et al., "Oligonucleotide Analogues as Potential Chemotherapeutic Agents," Pharmaceutical Research 5(9):539-549, Kluwer Academic/Plenum Publishers, United States (Sep. 1988).

(56) References Cited

OTHER PUBLICATIONS

Hashimoto, T., et al., "Hormone-Dependent Cancers and Bone Metastasis," Biotherapy, 14(11):1077-1084 (Nov. 2000).

Mercer, R.R and Mastro, A.M., "Cytokines Secreted by Bone-Metastatic Breast Cancer Cells Alter the Expression Pattern of F-Actin and Reduce Focal Adhesion Plaques in Osteoblasts through PI3K," Experimental Cell Research, 310(2):270-281, Academic Press, United States (Nov. 2005).

Partial European Search Report for Application No. EP17181286, dated Nov. 28, 2017, 23 pages.

Berre, S., et al., "CD36-specific antibodies block release of HIV-1 from infected primary macrophages and its transmission to T cells," Journal of Experimental Medicine 210(12):2523-2538, Rockefeller University Press, United States (Nov. 2013).

Huang, W., et al., "CD9 Tetraspanin Interacts with CD36 on the Surface of Macrophages: A Possible Regulatory Influence on Uptake of Oxidized Low Density Lipoprotein," PLoS ONE e29092 6(12): 1-7, PLoS ONE, United States (2011).

Xie, C., et al., "OxLDL or TLR2-induced cytokine response is enhanced by oxLDL-independent novel domain on mouse CD36," Immunol Lett. 137(1-2): 15-27, Elsevier, Netherlands (2011).

Co-Pending U.S. Appl. No. 17/108,390, inventor Gomis; R., et al., filed Dec. 1, 2020 (Un-Published).

Co-Pending U.S. Appl. No. 17/339,024, inventor Gomis; R., filed Jun. 4, 2021 (Un-Published).

Co-Pending U.S. Appl. No. 17/353,013, inventor Gomis; R., filed Jun. 21, 2021 (Un-Published).

Co-Pending U.S. Appl. No. 17/385,568, inventor Gomis; R., filed Jul. 26, 2021 (Un-Published).

Simantov, R. and Silverstein, R., "CD36: A critical anti-angiogenic receptor," Frontiers in Bioscience 8:874-882, Bioscience Research Institute, Singapore, (2003).

Aiken, M.L., et al., "Effects of OKM5, a monoclonal antibody to glycoprotein IV, on platelet aggregation and thrombospondin surface expression," Blood 76(12):2501-2509, American Society of Hematology, United States (Dec. 1990).

Delgado, A.V., et al., "Antibodies against human cell receptors, CD36, CD41a, and CD62P crossreact with porcine platelets," Cytometry B Clin Cytom. 56(l):62-67, Wiley, United States (Nov. 2003).

Diaz-Ricart, M., et al., "Antibodies to CD36 (GPIV) inhibit platelet adhesion to subendothelial surfaces under flow conditions,"Arterioscler Thromb Vasc Biol. 16(7):883-888, Lippincott Williams & Wilkins on behalf of the American Heart Association, United States (Jul. 1996).

Gillot, I., et al., "Germ cells and fatty acids induce translocation of CD36 scavenger receptor to the plasma membrane of Sertoli cells," J Cell Sci. 118:3027-3035, The Company of Biologists, United Kingdom (Jul. 2005).

Gordiyenko, N., et al., "RPE cells internalize low-density lipoprotein (LDL) and oxidized LDL (oxLDL) in large quantities in vitro and in vivo," Invest Ophthalmol Vis Sci. 45(8):2822-2829, Association for Research in Vision and Ophthalmology, United States (Aug. 2004).

Nakamura, K., et al., "Plasmodium falciparum-infected erythrocyte receptor(s) for CD36 and thrombospondin are restricted to knobs on the erythrocyte surface," J Histochem Cytochem. 40(9):1419-1422, SAGE Publications on behalf of the Histochemical Society, United States (Sep. 1992).

Stachowska, E., et al., "Conjugated linoleic acids regulate triacylglycerol and cholesterol concentrations in macrophages/foam cells by the modulation of CD36 expression," Acta Biochim Pol. 57(3):379-384, Polish Biochemical Society, United Kingdom (May 2010).

Stolzing, A., and Grune, T., "Neuronal apoptotic bodies: phagocytosis and degradation by primary microglial cells," FASEB J. 18(6):743-745, Federation of American Societies for Experimental Biology, United States (Feb. 2004).

\* cited by examiner

Bone metastasis BoM2 cells    Day 28

METHOD FOR THE DIAGNOSIS, PROGNOSIS AND TREATMENT OF CANCER METASTASIS

CROSS-REFERENCE TO RELATED APPLICATIONS

This application is a continuation of U.S. patent application Ser. No. 14/776,453 which is a National Stage of International Application Number PCT/IB2014/001128, filed Mar. 14, 2014, which claims the benefit of Spanish Application No. P201330384, filed Mar. 15, 2013, which are incorporated by reference herein in their entirety.

REFERENCE TO A SEQUENCE LISTING SUBMITTED ELECTRONICALLY VIA EFS-WEB

The content of the electronically submitted sequence listing (Name: 3190_0130003_SL.txt; Size: 4,096 bytes; and Date of Creation: Apr., 2, 2018) is herein incorporated by reference in its entirety.

OBJECTS OF THE INVENTION

This invention relates to methods to determine the likelihood a subject suffering from cancer, in particular breast, colon, lung, kidney or thyroid cancer, will develop a metastasis, in addition to methods for the creation of customized therapies for a subject suffering from cancer, in particular breast, colon, lung, kidney or thyroid cancer. Such methods consist of determining the expression level of a set of genes whose expression is related to the c-MAF gene expression. The invention also involves the use of PTHLH and PODXL inhibitors and RERG activators in the treatment and/or prevention of the metastatic cancer, in particular breast, colon, lung, kidney or thyroid cancer.

BACKGROUND OF THE INVENTION

Breast cancer is the second most common type of cancer worldwide (10.4%; after lung cancer) and the fifth most common cause of death by cancer (after lung cancer, stomach cancer, liver cancer and colon cancer). Is breast cancer the most common cause of death for women? In 2005, breast cancer led to 502,000 deaths worldwide (7% of cancer-related deaths; almost 1% of all deaths). The number of global cases has increased significantly since the 1970s, a phenomenon which is partly blamed on the modern lifestyles of the western world.

All the cells have receptors on their surface, in their cytoplasm and nucleus. Certain chemical messengers such as hormones bind to these receptors and this results in changes in the cell. Three major receptors may affect breast cancer cells: the estrogen receptor (ER), the progesterone receptor (PR) and HER2/neu. With the aim of naming the cells containing one of these receptors, a positive sign is used when the receptor is present and a negative sign when it is absent: ER positive (ER+), ER negative (ER−), PR+ (positive), PR negative (PR−), HER2+ (positive) and HER2 negative (HER2). Receptor status has become a critical evaluation of all forms of breast cancer, as it determines the suitability of the use of specific treatments such as tamoxifen or trastuzumab. The alpha isoform of the estrogen receptor (ER) is over-expressed in around 65% of diagnosed cases of breast cancer. This type of breast cancer is referred to as "ER-positive" (ER+). In this case the binding of the estrogen and ER promotes the proliferation of the cancerous mammary cells. Cancerous ER+ cells are highly dependent on this stimulus in order to spread, reason for which ER is currently used as a therapeutic target.

The fact that most deaths in cancer patients with solid tumors are caused by late metastasis make it crucial to understand the molecular and cellular mechanisms which enable a tumor to metastasize. Recent publications have illustrated how metastasis is caused by complex mechanisms about which little is known, in addition to how the different metastatic cell types exhibit a tropism for certain organs. These tissue-specific metastatic cells have a series of acquired functions which enable them to colonize specific organs.

Patent application EP1961825-A1 describes a method for forecasting the appearance of metastatic breast cancer to the bone, lung, liver and brain, consisting of defining the expression level of one or more markers in a cancerous tissue sample in relation to the corresponding expression level in a control sample, including c-MAF. Furthermore, this document requires the definition of several genes simultaneously in order to determine the survival of breast cancer patients and the relationship between the capacity of the gene signature to predict bone metastasis free-survival was not statistically significant. Bos, P. D., et al. [Nature, 2009, 459:1005-1009] describes genes involved in breast cancer metastasis to the brain.

Patent application US2005/0181375 describes methods for detecting metastatic breast cancer based on the detection of the expression levels of a number of genes which are regulated upwards or downwards in metastatic tumors, and, in particular, tumors which metastasize to the brain.

International patent application WO2010/000907 describes a genetic signature which is useful as a genomic predictor of distal metastases in breast cancer patients.

However, there is a state of the art need for genetic markers to diagnose and/or predict whether a patient suffering from a specific breast cancer, such as ER− or ER+ breast cancer, will develop a metastasis or not, thereby allowing for the use of an appropriate therapy on the subject suffering from the said cancer. The identification of new prognosis factors will serve as a guide in selecting the most appropriate treatments.

A SUMMARY OF THE INVENTION

The authors of this invention have identified a group of genes whose expression is increasing or diminishing in breast tumor samples as a result of changes in the expression of the c-MAF gene. By means of gain-of-function experiments and correlated clinical data the authors have validated the role of these genes, and, in particular, that of the RERG gene, whose expression is inversely related to that of c-MAF, and that of the PTHLH and PODXL genes, whose expression is directly related to the c-MAF expression, such as prognosis markers of ER+ breast cancer metastasizing to the bone.

Hence, in a first aspect, the invention is related to an in-vitro method for predicting metastatic cancer in a subject, in particular breast, colon, lung, kidney and thyroid cancer, but specifically breast cancer, consisting of determining the expression level in a sample of cancerous tissue of one or more genes whose expression is modulated in response to an increase in the c-MAF expression levels of the said tumor, where the changed expression levels of the aforementioned one or more genes in relation to a standard value are an indication of a high risk of developing metastatic cancer.

A second aspect of the invention relates to an in-vitro method for the creation of customized therapy for a subject suffering from cancer, in particular breast, colon, lung, kidney or thyroid cancer, but specifically breast cancer, consisting of determining the expression level in a sample of cancerous tissue of one or more genes whose expression is modulated in response to an increase in the c-MAF expression levels of the said tumor, where the changed expression levels of the aforementioned one or more genes in relation to a standard value are an indication that the subject in question is susceptible of receiving a therapy geared to the prevention of metastasis.

A third aspect of the invention relates to the use of an agent which inhibits the expression of a gene or the activity of the expression product of this gene for the preparation of a drug for the treatment and/or prevention of metastatic cancer, in particular breast, colon, lung, kidney or thyroid cancer, but specifically breast cancer, where the said gene is characterized due to the fact its expression in tumorous cells, in particular breast, colon, lung, kidney and thyroid cells, but specifically breast cancer cells, increases in response to an increase in c-MAF expression levels in these cells, or diminishes in response to a reduction in c-MAF expression levels in these cells.

A fourth aspect of the invention relates to the use of an agent which stimulates the expression of a gene or the activity of the expression product of this gene for the preparation of a drug for the treatment and/or prevention of metastatic cancer, in particular breast, colon, lung, kidney and thyroid cancer, but specifically breast cancer, where the said gene is characterized due to the fact its expression in tumorous cells, in particular breast, colon, lung, kidney and thyroid, but specifically breast cancer, increases in response to an increase in c-MAF expression levels in these cells, or diminishes in response to a reduction in c-MAF expression levels in these cells.

A final aspect of the invention relates to an in-vitro method for the identification of a marker gene in a subject suffering from cancer, in particular breast, colon, lung, kidney or thyroid cancer, but specifically breast cancer, comprising
  (i) the definition of the expression levels of a candidate and c-MAF gene in a primary cancer tumor sample, in particular breast cancer, and
  (ii) determining the change in the expression levels of the said candidate gene in a population of cancer cells, particularly breast cells, in response to a modulation of the c-MAF gene expression
where the expression levels of the said gene are statistically significant in relation to the c-MAF expression in the primary cancer tumor sample, in particular breast cancer, and the change in the expression in response to the modulation of the c-MAF gene expression is statistically significant in relation to the change in the levels of the said gene is an indication that the said gene is a marker of a subject's propensity to develop metastasis.

DETAILED DESCRIPTION OF THE INVENTION

Figure 1A:
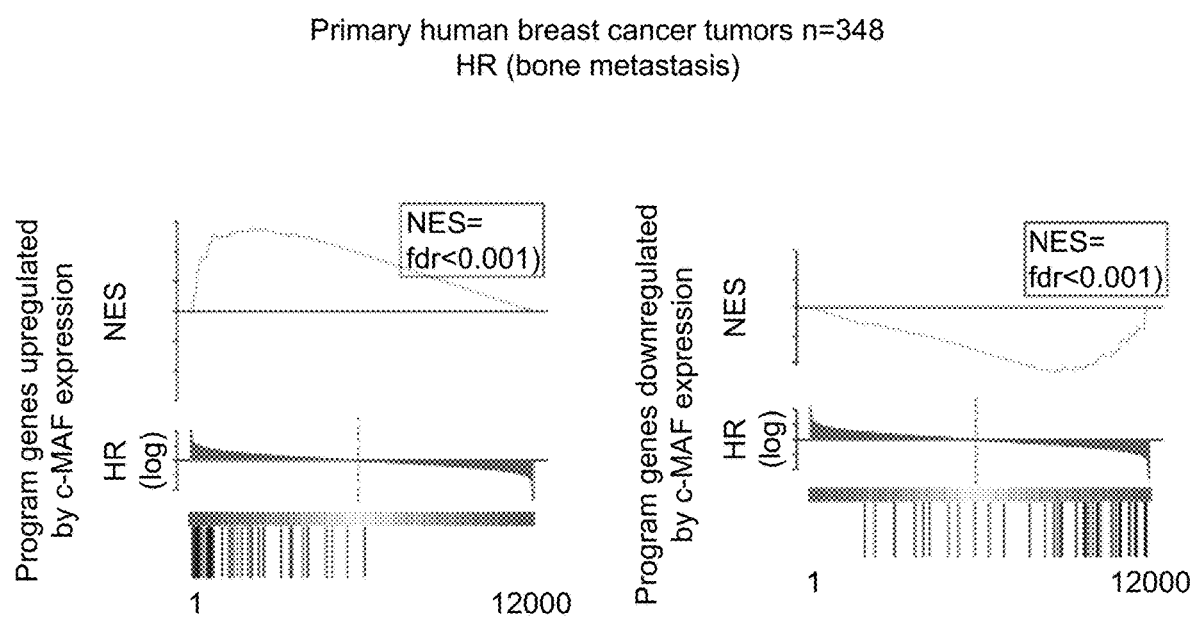
FIGS. 1A and B. (1A) Association of the increased (left) or diminished (right) MBP genes with the phenotype of bone metastasis in patients with ER+ breast cancer ("GSEA" algorithm). (1B) Association of the increased (left) or diminished (right) MBP genes with the phenotype of bone metastasis in a series of metastases to the bone, lung, liver and brain deriving from a primary breast cancer tumor ("GSEA" algorithm). The same approximation for increased genes has been conducted for metastasis to the lung, brain and liver.

Definitions of General Expressions and Terms "c-MAF inhibitor", as used in this invention, refers to any molecule capable of partially or totally inhibiting the expression of the c-MAF gene, both preventing the expression of the said gene from being produced (disrupting the transcription of the c-MAF gene and/or blocking the translation of the mRNA from the c-MAF gene expression) and directly inhibiting c-MAF protein activity. c-MAF gene expression inhibitors can be identified using methods based on the capacity of the supposed inhibitor to block the capacity of c-MAF to promote in vitro cellular proliferational as illustrated in the application for international patent WO2005/046731, based on the capacity of the supposed inhibitor to block the transcription capacity of a reporter gene under the control of a cyclin-D2 promoter or a promoter containing the c-MAF response region (MARE or c-MAF responsive element) in cells expressing c-MAF, as described in WO2008098351, or based on the capacity of the supposed inhibitor to block the expression of a gene under the control of the IL-4 promoter in response to the stimulation with PMA/ionomycin in cells expressing NFATc2 and c-MAF, as described in US2009048117A.

In the context of this invention, "inhibitor antibody" means an antibody which is capable of binding with the expression product in a specific manner and inhibiting one of more functions of that protein.

The term "small interfering RNA" ("siRNA") refers to the duplex of small RNA inhibitors which induce RNA interference. These molecules may vary in length (generally 18-30 base pairs) and contain varying degrees of complementarily to their target mRNAs in the antisense chain. Some siRNAs, but not all, feature outstanding unpaired bases on the 5' or 3' ends of the sense strand and/or the antisense strand. The term "siRNA" includes the duplex of two separate chains. As used herein, siRNA molecules are not limited to RNA molecules but also include nucleic acids with one or more chemically modified nucleotides such as morpholines.

The term "shRNA" or "short hairpin RNA" as used herein, refers to a dsRNA in which the two chains are bound by a strand without disrupting the nucleotides between the 3' end of a strand and the 5' end of the other strand to form a duplex structure.

The term "increased gene expression" refers to the fact the expression levels of a gene are high in relation to standard or control values, which correspond to the expression level of the same gene in a control sample. In accordance with this invention, the expression levels of a gene are regarded as high in relation to a standard value when the levels of a patient's sample have increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more.

"c-MAF", as used in this invention, refers to a gene also known as "v-maf musculoaponeurotic fibrosarcoma oncogene homologue" (avian), MAF or MGC71685), which is a transcription factor containing a leucine zipper which acts a homodimer or heterodimer. Depending on the DNA binding site, the encoded protein may be a transcriptional activator or repressor. The DNA sequence which encodes c-MAF is described in the NCBI database under access number NG_016440 (version of the NCBI corresponding to Dec., 18, 2011). The aforementioned DNA sequence is followed by the transcription of two messenger RNAs, each of which will give way to one of the c-MAF protein isoforms, isoform α or 1 (corresponding to the long c-MAF isoform) and isoform β or 2 (corresponding to the short c-MAF iosform). The complementary DNA sequences for each of the aforementioned isoforms are described in the NCBI database under access numbers NM_005360.4 and NM_001031804.2 respectively (version of the NCBI corresponding to Dec., 18, 2011).

The term "cancer" or "carcinoma" or "tumor" refers to an illness characterized by the uncontrolled proliferation of abnormal cells capable of invading adjacent tissues and spreading to distant organs. This term includes, but is not restricted to, cancer of the breast, heart, small intestine, colon, spleen, kidney, bladder, head, neck, ovaries, prostate gland, brain, pancreas, skin, bone, bone marrow, blood, thymus, womb, testicles, hepatobiliary system and liver; in addition to tumors such as, but not limited to, adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, hepatobiliary cancer, osteosarcoma, retinoblastoma, rhabdomyosarcoma, sarcoma and teratoma. Furthermore, this term includes acrolentiginous melanoma, actinic keratosis adenocarcinoma, adenoid cystic carcinoma, adenomas, adenosarcoma, adenosquamus carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Ewing sarcoma, focal nodular hyperplasia, germ cell tumors, glioblastoma, glucagonoma, hemangioblastoma, hemagioendothelioma, hemagioma, hepatic adenoma, hepatic adenomastosis, hepatocellular carcinoma, hepatobiliary cancer, insulinoma, intraepithelial neoplasia, squamous cell intraepithelial neoplasia, invasive squamous-cell carcinoma, large cell carcinoma, leiomyosarcoma, melanoma, malignant melonoma, malignant mesothelial tumor, medulobastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, microcytic carcinoma, soft tissue carcinoma, somatostatin secreting tumor, squamous carcinoma, squamous cell carcinoma, undifferentiated carcinoma, uveal melanoma, verrucous carcinoma, vipoma, Wilm tumor, intracerebral cancer, head and neck cancer, rectal cancer, astrocytoma, glioblastoma, microcytic cancer and non-microcytic cancer, metastatic melanoma, androgen-independent metastatic prostate cancer, androgen-dependent metastatic prostate cancer and breast cancer. In relation to this particular invention, cancer refers to breast, colon, lung, kidney or thyroid cancer, but specifically breast cancer.

The expression "colon cancer" refers to any malignant proliferative disorder of colon, rectum and appendix cells. The term colon cancer includes any of the following stages of the illness:

Stage 0: Incipient cancer in the innermost layer of the intestine

Stage 1: Cancer in the inner layers of the intestine

Stage 2: Cancer which has spread via the muscle wall of the colon

Stage 3: Cancer which has spread to the lymph nodes

Stage 4: The cancer has spread to other organs.

The expression "breast cancer", "mammary cancer" or "bosom cancer" refers to the type of cancer which originates in the mammary tissue. The term "breast cancer" includes cancers classified under any of the phases in accordance with the TNM system. Prognosis is closely linked to the results of the classification in phases, and the classification in phases is also used to assign patients treatments both in clinical trials and medical practice. The information in relation to classification in phases is as follows:

TX: The primary tumor cannot be assessed. T0: There is no evidence of a primary tumor. TIVE in situ, carcinoma, non-invasive T1: The tumor is 2.0 cm or smaller. T2: The tumor is larger than 2 cm but not larger than 5 cm. T3: The tumor is larger than 5 cm. T4: Tumor of any size growing on the chest wall or skin, inflammatory breast cancer.

NX: The neighboring lymph nodes cannot be assessed. N0: The cancer has not spread to lymph nodes. N1: The cancer has spread to 1 to 3 axillary lymph nodes or one internal mammary node. N2: The cancer has spread to 4 to 9 axillary lymph nodes or multiple internal mammary nodes. N3: Applies to one of the following:

The cancer has spread to 10 or more axillary lymph nodes, or the cancer has spread to the lymph nodes beneath the collarbone, or the cancer has spread to the lymph nodes above the collarbone, or the cancer is affecting the axillary lymph nodes and has spread to the internal mammary lymph nodes, or the cancer is affecting 4 or more axillary lymph nodes, and minimum amounts of cancer are found in the internal mammary nodes or in a sentinel lymph node biopsy.

Max The presence of distant extension (metastasis) cannot be assessed. M0:

There is no distant extension. M1: Extension to distant organs has occurred, not including the supraclavicular lymph node.

The expression "lung cancer" or "cancer of the lungs" o "pulmonary carcinoma" refers to any cancer of the lung and includes non-small-cell lung cancer, non-microcytic lung cancer (NSCLC) and small-cell lung cancer.

The expression "kidney cancer" or "renal cancer" or "renal carcinoma" refers to any malignant proliferative disorder of the kidney cells.

The expression "thyroid cancer" or "thyroid carcinoma" refers to any proliferative disorder of the thyroid gland, and includes, but is not limited to, papillary thyroid carcinoma and follicular thyroid carcinoma.

"Statistically significant correlation" as used herein to refer to two events (expression levels of a candidate gene and expression levels of a c-MAF gene) mean there is a high probability that these events are related and that the change is not random.

The expression "determine the likelihood of the development of metastatic cancer in a subject suffering from cancer", in particular breast, colon, lung, kidney or thyroid cancer, preferably in a subject suffering from breast cancer, refers to using evidence to determine whether or not the cancer affecting the said subject will turn metastatic in the future. In the context of this invention, the index is the change in the expression levels of one or more genes whose expression is se modula in response to an increase in c-MAF expression levels in relation to standard value. "A change in the expression levels of a gene" refers to a variation, either upwards or downwards, in the expression level of the gene in relation to a standard value. Hence, a "high" or "increased" or "enhanced" likelihood of the development of metastasis in a subject suffering from cancer, in particular breast, colon, lung, kidney or thyroid cancer, but specifically breast cancer, is due to the change in the expression levels of one or more genes whose expression is se modula in response to an increase in c-MAF expression levels in relation to standard value.

The term "reduced gene expression" refers to when the expression levels of a gene have fallen or diminished in relation to standard or control values, which correspond to the expression level of the same gene in a control sample. For the purposes of this invention, the expression levels of a gene in relation to a standard value will be regarded as reduced when the levels in the patient sample have fallen by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more.

The term "marker gene" or "informative gene", as used in this invention, refers to a gene which expresses itself in a differentiated manner in populations with different phenotypes and whose differential expression, separately or combined with other genes, relates to a specific phenotype to a greater extent than would be expected randomly.

"PODXL gene", also known as podocalyxin-like, refers to a gene which encodes a protein forming part of the sialomucin family, and which is an important component of glomerular podocytes. Podocytes are highly differentiated epithelial cells with interdigital protruberances covering the outer surface of the basal glomerular membrane. Other biological activity causing this protein to encode includes: the binding of the same in a membrane-protein complex with the regulatory factor of the Na+/H+ exchanger of the intracellular cytoskeletal elements and their binding to L-selectin. A description of two transcripcional PODXL variants has been filed in the NCBI database (Mar. 3, 2013 version) under access numbers NM_001018111.2 (variant 1) and NM_005397.3 (variant 2). The sequences of the protein encoded by the PODXL gene are filed in the NCBI database (Mar. 3, 2013 version) under access numbers NP_001018121.1 (isoform 1) and NP_005388.2 (isoform 2).

"The PTHLH" (parathyroid hormone-like hormone gene) is located in the human 12 chromosome and encodes a protein belonging to the parathyroid hormone family known as PTHrP (parathyroid hormone-related protein). This protein regulates endochondral bone development in addition to the interaction between the epithelium and mesenchyme during the formation of the mammary glands and teeth. The receptor for this hormone is named PTHR1. The DNA sequence in relation to PTHLH is filed in the NCBI database under access number NG_023197 (Nov. 6, 2011 version). The description of four PTHLH transcript variants are filed in the NCBI database (Nov. 20, 2011) under access number NM_198965.1 (variant 1), NM_002820.2 (variant 2), NM_198964.1 (variant 3) and NM_198966.1 (variant 4). Likewise, the sequences of the protein encoded by the PTHLH gene are filed in the NCBI database (Jan. 10, 1995 version) under access numbers AAA60360.1 (form A), AAA60358.1 (form B) and AAA60359.1 (form C).

"The RERG gene", also known as Ras-like estrogen-regulated growth inhibitor, refers to a gene which encodes a protein forming part of the RAS GTPase superfamily, and which acts as an inhibitor against cellular proliferation and the formation of tumors. The description of two transcriptional RERG variants have been filed in the NCBI database (Nov. 28, 2011 version) under access numbers NM_032918.2 (variant 1) and NM_001190726.1 (variant 2). The sequences of the protein encoded by the RERG gene are filed in the NCBI database (Nov. 28, 2011) under access numbers NP_116307 (isoform 1) and NP_001177655 (isoform 2).

"Metastasis" is the spread of a cancerous source from the initial site of the same to another organ. This normally occurs via the blood or lymphatic system. When the cancerous cells spread and cause a new tumor, this is called a secondary or metastatic tumor. The cancer cells that form the secondary tumor are like those in the original tumor. For example, if a breast cancer spreads (metastasizes) to the lung, the secondary tumor comprises malignant breast cancer cells. The disease in the lung is called metastatic breast cancer (not lung cancer). In the case of this particular invention, metastasis is breast cancer, colon cancer, lung cancer, kidney cancer or thyroid cancer which has spread (metastasized) to the bone. With even further particular respect to this invention, metastasis is ER+ breast cancer which has spread (metastasized) to the bone.

"Osteolytic bone metastasis" refers to a type of metastasis which causes bone resorption (progressive loss of bone density) in the vicinity of the metastasis resulting from the stimulation of osteoclast activity by the tumor cells and characterized by severe pain, pathological fractures, hypocalcaemia, compression of the spinal cord and other syndromes resulting from nerve compression.

The term "micro RNA" or "miRNA" refers to short single-stranded RNA molecules, typically around 21-23 nucleotidos in length and capable of regulating gene expression. miRNAs may be synthetic (in other words, recombinant) or natural. Natural miRNAs are encoded by genes which transcribe from the DNA and process from primary transcripts ("pri-miRNA") to short stem-loop structures ("pre-miRNA") and finally, to mature miRNA. Mature miRNA molecules are partially complementary to one or more mRNA molecules and reduce gene expression by means of a process similar to the interference of RNA or inhibiting the translation of the mRNA.

"Tumor tissue sample" is the tissue sample from the primary tumor, in particular breast cancer, colon cancer, lung cancer, kidney cancer or thyroid cancer, more specifically ER+ or ER–Her2– breast cancer. Said sample may be obtained through conventional methods, for example, biopsy, using methods well known by the experts in related medical techniques. The methods for obtaining a biopsy sample include splitting a tumor into large pieces, or microdissection or other cell separating methods known in the technique. The tumor cells may additionally be obtained by means of cytology through aspiration with a small gauge needle. To simplify sample preservation and handling, samples can be fixed in formalin and soaked in paraffin or first frozen and then soaked in a tissue-freezing medium such as OCT compound by means of immersion in a highly cryogenic medium which enables rapid freezing. According to the present invention, the sample also involves any body fluids that contain tissue originating from the tumor, RNA originating from the tumor, DNA originating from the tumor or protein originating from the tumor, including, but not limited to, plasma or serum, such as plasma or serum with the presence of exosomes or DNA of tumor origin.

The expression "dominant negative mutant" of a gene expression product, as it is used in the present invention, refers to a variant of said expression product that is capable of interfering with the activity of the native expression product.

The term "inhibitor peptide", as it is used herein, refers to those peptides capable of binding to an expression product and inhibiting its activity.

The term "metastasis prediction" is used herein to refer to the probability by which a patient may develop metastasis. The prediction methods of the present invention may be used clinically to make decisions about the most suitable choice for treatment for each patient in particular. The prediction methods of the present invention are valuable tools for predicting whether a patient is going to respond favorably to a treatment regimen, such as chemotherapy. The prediction may include prognosis factors. As experts in the field will understand, and although this is not preferable, prediction does not have to be correct for 100% of the subjects who may be diagnosed or evaluated.

The term, however, requires that a significant part of the subjects may be identified as those with a greater probability of having a determined result. If a subject is statistically significant, this may be determined by an expert in the field using different known statistical evaluation tools, for example, the determination of confidence intervals, determination of the p-value, cross validation rates of classification and details, etc., as shown in Dowdy and Wearden, Statistics for Research by Wiley, John & Sons, New York, 1983. The recommended confidence intervals are at least 50%, at least 60%, at least 70%, at least 80%, at least 90% or at least 95%. P-values are preferably 0.01, 0.005, or below.

The term "probability", as it is used herein, measures the frequency by which a result (or set of results) is obtained by carrying out a randomized experiment, of which all the possible results are known, under sufficiently stable conditions. Probability may be "high" or "low". As experts in the field will understand, probability does not have to be 100% for all subjects evaluated, although it should preferably be this way. Whether a correlation is statistically significant or not, can be determined without great complications, by a technician in the field, using different known statistical evaluation tools, for example, by means of the determination of confidence intervals, determination of the p-value, Student's t-test, Mann-Whitney test, etc. Additional information on these statistical tools can be found in Dowdy and Wearden, Statistics for Research. John Wiley & Sons, New York 1983. The preferred confidence intervals are at least 50%, at least 60%, at least 70%, at least 80%, at least 90% or at least 95%. The p values are, preferably, 0.05, 0.02, 0.01 or lower.

"Breast tissue-specific promoter", as used in the present invention, refers to a sequence of nucleic acids that functions as promoter and that enables the expression of a nucleic acid operatively associated to said promoter specifically in breast tissue without observing significant expression in other tissues.

The term "subject" or "patient", as used herein, refers to all animals classified as mammals and includes, but is not restricted to, domestic and farm animals, primates and humans; for example, human beings, non-human primates, cows, horses, pigs, sheep, goats, dogs, cats or rodents. Preferably, the subject is a male or female human of any age or ethnicity.

"Primary tumor" refers to a tumor that originates in the tissue or organ where it is found and that has not metastasized to said location from another location.

"ER+ tumor" refers to tumors that express ER above a determined level. ER levels above or equal to 10 fmol/mg, positive detection by immunohistochemical medium of more than 10% of the nuclei, are the usual criteria for considering a breast tumor as ER+.

"ER− tumor" as used in the present invention, refers to tumors in which less than 5% of the nuclei of tumor cells show ER expression using immunohistochemical techniques (for example, using the method described by Elizabeth H et al., 2010, Journal of Clinical Oncology, 28: 2784-2795)

"Her2− tumor" refers to tumors in which the cells do not show amplification of the HER2 gene. Tumor cells are considered to be negative for HER2 when the value obtained using a semi-quantitative immunohistochemical assay using a polyclonal anti-HER2 antibody (for example, the HercepTest Kit (Code K5204), Dako North America, Inc., (Code K5204) is 0, 1+ or 2+. Alternatively, a tumor is considered to be Her2− when the number of HER2 gene copies per nucleus is lower than 4 or when the ratio of the number of HER2 gene copies compared to the number of chromosome 17 copies determined by FISH is less than 1.8. Standard assays for determining whether a tumor is Her2+ or Her2− are described, for example, in the American Society of Clinical Oncology/College of American Pathologists guidelines (Wolff A C, et al. J Clin Oncol., 2007, 25: 118-145; Wolff A C, et al., 2007, Archives of Pathology Laboratory Medicine 131: 18-43).

"PR− tumor" refers to tumors that do not detectably express the progesterone receptor. In the current context, progesterone receptor levels less than 10 fmol/mg and/or an immunohistochemical observation less than 10 percent of positive nuclei is considered to be PR-negative.

"Triple negative tumor" refers to a breast cancer characterized by being ER−, PR− and HER2−.

The expression "reference value" refers to a laboratory value used as reference for the values/data obtained by means of samples obtained from the patients. The reference value or reference level can be an absolute value, a relative value, a value that has an upper and/or lower limit, a series of values, an average value, a median, a mean value, or a value expressed by referring to a control or reference value. A reference value may be based on the value obtained from an individual sample, such as, for example, a value obtained from a sample from the patient object of the study, but obtained at a previous point in time. The reference value may be based on a high number of samples, such as the values obtained in a population of subjects from a chronological age group coinciding with that of the patient object of the study or based on a set of inclusion or exclusion samples of the sample to be analyzed.

The expression "specific antisense oligonucleotide for a gene", as used in the present invention, refers to an oligonucleotide whose sequence is partially or totally complementary to a region of said gene, of the pre-mRNA coded by said gene or of the mRNA of said gene, so that it is able to specifically hybrid with said gene, pre-mRNA or mRNA thereby blocking the gene transcription or mRNA translation.

Antisense nucleic acids can bind to the potential target of the drug by means of conventional base complementarily or, for example, in the case of binding to bicatenary DNA, by way of specific interactions in the major groove of the double helix. In general, these methods refer to the range of techniques often used in the technique and include any method that is based on specific binding to oligonucleotide sequences.

An antisense construction of the present invention may be provided, for example, as an expression plasmid that, when transcribed in the cell, produces RNA that is complementary to at least one single part of cellular mRNA that codes the target gene. Alternatively, antisense construction is a oligonucleotide probe generated ex vivo and that, when introduced to the cell, causes inhibition of gene expression hybridizing with mRNA and/or genomic sequences of a target nucleic acid. Said oligonucleotide probes are preferably modified oligonucleotides that are resistant to endogenous nucleases, for example, exonucleases and/or endonucleases, and are therefore stable in vivo. Example nucleic acid molecules for use as antisense oligonucleotides are phosphoramidite, phosphotionate and methylphosphonate DNA analogs (see also U.S. Pat. Nos. 5,176,996; 5,264,564; and U.S. Pat. No. 5,256,775). Furthermore, general approaches to constructing oligomers useful in antisense therapy have been reviewed, for example in Van der Krol et al., BioTechniques 6: 958-976, 1988; and Stein et al., Cancer Res 48: 2659-2668, 1988.

Regarding the antisense oligonucleotide, the regions of oligodeoxyribonucleotides deriving from the translational initiation site, for example between −10 and +10 of the target gene, are preferable. Antisense approaches involve oligonucleotide design (either DNA or RNA) that is complementary to the mRNA that codes the target polypeptide. Antisense oligonucleotides will bind to the mRNA transcripts and prevent translation.

Oligonucleotides that are complementary to the 5' end of the mRNA, for example, the 5' untranslated sequence and including the AUG start codon, should function in the most efficient manner to inhibit translation. However, it has recently been shown that sequences complementary to 3' untranslated sequences of mRNA are also effective in inhibiting the translation of mRNAs (Wagner, Nature 372: 333, 1994). Therefore, complementary oligonucleotides could either be used on non-coding 5' or 3' untranslated regions of a gene in an antisense approach to inhibit translation of this mRNA. Complementary oligonucleotides to the 5' untranslated region of mRNA should be included in the complement of the AUG start codon. Complementary oligonucleotides to the coding regions of mRNA are less effective translation inhibitors but may also be sued according to the invention. If they are designed to hybrid with the 5',3' or coding region of the mRNA, antisense nucleic acids should have at least six nucleotides in length and preferably have less than around 100 and, more preferably, have less than around 50, 25, 17 or 10 nucleotides in length.

Antisense oligonucleotides may be from single-chain or double-chain DNA or RNA or chemical mixtures or derivatives or modified versions of the same. The oligonucleotide can be modified in the base group, sugar group or phosphate backbone, for example, to improve the stability of the molecule, its hybridization capacity, etc. The oligonucleotide may include other bound groups, such as peptides (for example, to guide them to host cell receptors) or agents to facilitate transport by way of the cell membrane (see, for example, Letsinger et al., Proc. Natl. Acad. Sci. U.S.A. 86: 6553-6556, 1989; Lemaitre et al., Proc. Natl. Acad. Sci. 84: 648-652, 1987; PCT publication No. WO88/09810) or blood-brain barrier (see, for example, PCT publication No. WO89/10134), intercalating agents (see, for example, Zon, Pharm. Res. 5: 539-549, 1988). For this purpose, the oligonucleotide may be conjugated to another molecule, for example, a peptide, a transporter agent, a cutting agent triggered by hybridization, etc.

Antisense oligonucleotides may include at least one group of modified base. The antisense oligonucleotide may also include at least one group of modified sugar selected from the group that includes, but is not limited to, arabinose, 2-fluorarabinose, xylulose, and hexose. The antisense oligonucleotide may also contain a backbone similar to neutral peptide. Said molecules are called peptide nucleic acid (PNA) oligomers and are described, for example, in Perry-O'Keefe et al., Proc. Natl. Acad. Sci. U.S.A. 93: 14670, 1996, and in Eglom et al., Nature 365: 566, 1993.

In another form of synthesis, the antisense oligonucleotide comprises at least a modified phosphate backbone. In an additional form of synthesis the antisense oligonucleotide is an alpha-anomeric oligonucleotide.

While antisense oligonucleotides complementary to the encoding region of the target mRNA sequence may be used, those which are complementary to the untranslated transcribed region can also be used.

In some cases, it may be difficult to reach intracellular concentrations antisense that are able to suppress the translation of endogenous mRNAs. Therefore, the preferred approach is to use a recombinant DNA construction in which the antisense oligonucleotide is placed under the control of a strong pol III or pol II promoter.

Alternatively, target gene expression may be reduced by directing deoxyribonucleotide sequences complementary to the gene regulatory region (that is, the promoter and/or potentiators) to form triple helix structures that prevent gene transcription in target cells in the body (see, in general, Helene, Anticancer Drug Des. 6(6): 569-84, 1991). In certain forms of synthesis, antisense oligonucleotides are antisense morpholinos.

The expression "RNA interference" or RNAi is a sequence specific and post-transcriptional repression process of gene expression that may occur in eukaryotic cells. In general, this process involves the degradation of a particular sequence of mRNA induced by double stranded RNA (dsRNA) that is homologous to said sequence. This dsRNA is capable of causing gene expression silencing by converting RNA into siRNA by means of a type of RNase II (Dicer).

The term "nucleic acid", as used herein, refers to a polymer that has two or more deoxyribonucleotide, ribonucleotide or nucleotide analog molecules as well as molecules that are structurally similar to a native nucleic acid, but differ from native nucleic acid (for example, by chemical modification) at one or more of the nucleic acid backbone (for example, phosphate in native nucleic acids), nucleic acid sugar (for example, deoxyribose for native DNA and ribose in native RNA) and nucleic acid base (for example, adenosine, cytosine, guanine, thymidine or purine in native nucleic acids).

An "antisense sequence", as used herein, includes antisense or sense oligonucleotides that compose a monocatenary nucleic acid sequence (RNA or DNA) capable of binding to target DNA (antisense) or mRNA (sense) sequences. The ability to create an antisense or a sense oligonucleotide based upon a cDNA sequence encoding a given protein is described, for example, in Stein and Cohen, Cancer Res. 48:2659, (1988) and van der Krol et al., BioTechniques 6:958, (1988).

As used herein, the term "ribozyme" or "RNA enzyme" or "catalytic RNA" refers to an RNA molecule that catalyzes a chemical reaction. Many natural ribozymes catalyze the hydrolysis of one or more of their own phosphodiester bonds or the hydrolysis of bonds in other RNAs, but they have also been found to catalyze the aminotransferase activity of the ribosome, the ligation activity of a DNA ligase and a number of other chemical reactions performed by conventional protein enzymes.

The term treatment refers to the administration of a drug to provide relief for or eliminate a disease, to reduce or eliminate one or more symptoms associated to said disease or so that a patient may obtain clinical benefit, widely defined as: reduction in tumor size, reduction in the occurrence or size of metastasis, reduction or detention of tumor growth, induction of remission, increase in duration before recurrence, reduction in pain associated to the tumor, inhibition of tumor cell division, extermination of tumor cells, induced apoptosis of tumor cells, reduction, reduction of tumor recurrence and/or increase in patient survival.

In Vitro Method for Predicting Metastasis in a Subject Affected by Cancer, Specifically Breast Cancer The authors of the present invention have identified a group of genes whose expression is positively or negatively correlated with the expression of c-MAF. Specifically, the authors have identified a series of genes characterized because (i) their expression in primary tumors is significantly correlated to MAF expression and (ii) their expression in MCF7 cells is modified with c-MAF overexpression (long or short isoforms) or with c-MAF silencing in cells highly metastasized to bone deriving from MCF7 that express MAF. The genes that meet these conditions are considered to be members of the program of bone metastasis mediated by c-MAF. These genes are shown in Tables 1 (genes increased by c-MAF program) and 2 (genes suppressed by MAF program). Using gain of function experiments and clinical correlation data, the inventors have functionally validated the role of PTHLH, PODXL and RERG as causal target genes of the bone metastatic processes of ER+ breast cancer and as part of the program of bone metastasis mediated by c-MAF.

Thus, as a first issue, the invention is related to an in vitro method (hereinafter, first method of the invention) for predicting the metastasis of a cancer, specifically breast cancer, colon cancer, lung cancer, kidney cancer or thyroid cancer, more specifically breast cancer, in a subject that involves determining the level of expression, in said subject's tumor tissue sample, of one or more genes whose expression is modulated in response to an increase in c-MAF expression levels in which altered expression levels of one or more genes compared to a reference value are indicative of a high risk of developing metastasis.

The first method of the invention involves, as a first step, quantifying the level of expression of one or more genes whose expression is modulated in response to an increase in c-MAF expression levels in a tumor tissue sample of a subject affected by cancer, specifically breast cancer, colon cancer, lung cancer, kidney cancer or thyroid cancer, more specifically breast cancer.

The expression "genes whose expression is modulated in response to an increase in c-MAF expression levels", as used in the present invention, refers to genes whose expression is significantly modified in response to changes in c-MAF expression levels. Genes whose expression is modulated in response to an increase in c-MAF expression levels includes genes whose expression in primary tumor samples is significantly correlated with c-MAF expression and/or genes whose expression is modified in breast cancer cells in response to changes in c-MAF expression levels.

Performed in the preferred form, genes whose expression is modulated in response to an increase in c-MAF expression levels include genes whose expression increases in primary tumor samples that show high c-MAF expression and/or genes whose expression increases in cancer cells, preferably breast, colon, lung, kidney or thyroid cells, even more preferably breast cells, in response to an increase in c-MAF expression levels and/or genes whose expression decreases in cancer cells, preferably breast, colon, lung, kidney or thyroid cells, even more preferably breast cells, in response to c-MAF expression silencing.

Performed in the preferred form, genes whose expression is modulated in response to an increase in c-MAF expression levels include genes whose expression decreases in primary tumor samples that show high c-MAF expression and/or genes whose expression decreases in cancer cells, preferably breast, colon, lung, kidney or thyroid cells, even more preferably breast cells, in response to an increase in c-MAF expression levels and/or genes whose expression increases in cancer cells, preferably breast, colon, lung, kidney or thyroid cells, even more preferably breast cells, in response to c-MAF expression silencing.

In the present invention "increased" or "augmented" expression level is understood as the level of expression that refers to levels greater than the reference value levels. In particular, it can be considered that a sample from a subject presents increased expression levels when the expression levels in the subject's sample are at least 1.1 times, 1.5 times, 5 times, 10 times, 20 times, 30 times, 40 times, 50 times, 60 times, 70 times, 80 times, 90 times, 100 times or even greater compared to the reference value.

Moreover, in the present invention "decreased" or "reduced" expression level is the expression level that refers to levels lower than the reference value. In particular, it can be considered that a sample from a subject presents decreased expression levels when the expression levels in the reference sample are at least 1.1 times, 1.5 times, 5 times, 10 times, 20 times, 30 times, 40 times, 50 times, 60 times, 70 times, 80 times, 90 times, 100 times or even greater compared to the subject's sample.

Performed in the preferred form, the first method of the invention involves quantifying the expression level of one or more genes selected from the group of genes showed in Table 1 and/or one or more genes selected from the group of genes shown in Table 2 in a tumor tissue sample of a subject affected by cancer, specifically breast cancer.

TABLE 1

Genes whose expression is positively correlated with c-MAF expression.

| | Gene | Gene ID (Homo sapiens) | A | B | C | D |
|---|---|---|---|---|---|---|
| 1 | AKR1C3 | 8644 | + | + | + | |
| 2 | APOD | 347 | + | + | | |
| 3 | C5orf4 | 10826 | + | | + | − |
| 4 | CAV1 | 857 | + | + | + | − |
| 5 | CAV2 | 858 | + | + | + | − |
| 6 | CD55 | 1604 | + | + | + | − |
| 7 | CHL1 | 10752 | + | + | | − |
| 8 | COLEC12 | 81035 | + | + | + | |
| 9 | DOCK4 | 9732 | + | + | | − |
| 10 | HCLS1 | 3059 | + | + | | − |
| 11 | MAFB | 9935 | + | + | + | |
| 12 | NAV3 | 89795 | + | | | − |
| 13 | NPR1 | 4881 | + | + | + | − |
| 14 | PRELP | 5549 | + | + | + | |
| 15 | PTPRN2 | 5799 | + | + | + | |
| 16 | SCGB2A2 | 4250 | + | + | | |
| 17 | TNFSF10 | 8743 | + | + | + | − |
| 18 | XYLT1 | 64131 | + | + | + | − |
| 19 | ACTG2 | 72 | + | | + | − |
| 20 | BCL11A | 53335 | + | | − | |

TABLE 1-continued

Genes whose expression is positively correlated with c-MAF expression.

| | Gene | Gene ID (Homo sapiens) | A | B | C | D |
|---|---|---|---|---|---|---|
| 21 | CCND2 | 894 | + | + | | − |
| 22 | CSRP2 | 1466 | + | | | − |
| 23 | DOK5 | 55816 | + | | | − |
| 24 | DZIP1 | 22873 | + | | | − |
| 25 | FMO2 | 2327 | + | | | − |
| 26 | GABRP | 2568 | + | | | − |
| 27 | IGF1 | 3479 | + | + | | − |
| 28 | IRAK3 | 11213 | + | | | − |
| 29 | KCNJ2 | 3759 | + | | | − |
| 30 | LMCD1 | 29995 | + | | | − |
| 31 | LRRC2 | 79442 | + | | | − |
| 32 | LRRN3 | 54674 | + | | | − |
| 33 | NAALAD2 | 10003 | + | | | − |
| 34 | P2RY14 | 9934 | + | | | |
| 35 | RPL22 | 6146 | + | + | | − |
| 36 | SCG5 | 6447 | + | | | − |
| 37 | VTCN1 | 79679 | + | + | + | − |
| 38 | ABCC3 | 8714 | + | + | + | |
| 39 | ALDH1A3 | 220 | + | | + | |
| 40 | ARID5B | 84159 | + | + | + | − |
| 41 | ATF1 | 466 | + | | + | − |
| 42 | BTN3A3 | 10384 | + | | + | |
| 43 | CLIP4 | 79745 | + | + | + | |
| 44 | DAB2 | 1601 | + | + | + | − |
| 45 | DIAPH2 | 1730 | + | + | + | − |
| 46 | EDN1 | 1906 | + | + | + | − |
| 47 | FAM70A | 55026 | + | | + | |
| 48 | FAS | 355 | + | | + | |
| 49 | FAT1 | 2195 | + | | + | |
| 50 | GAS1 | 2619 | + | + | + | |
| 51 | KCTD12 | 115207 | + | | + | − |
| 52 | KRT81 | 3887 | + | | + | − |
| 53 | MALL | 7851 | + | | + | |
| 54 | NT5E | 490 | + | + | + | |
| 55 | PDE1A | 5136 | + | | + | − |
| 56 | PDGFC | 5155 | + | | + | |
| 57 | PTGS2 | 5743 | + | + | + | − |
| 58 | QKI | 9444 | + | | + | |
| 59 | TNS3 | 64759 | + | + | + | |
| 60 | VGLL3 | 389136 | + | | + | |
| 61 | ABCG2 | 9429 | + | + | + | |
| 62 | CD36 | 948 | + | + | + | |
| 63 | EFEMP1 | 2202 | + | + | + | |
| 64 | FGF18 | 8817 | + | + | + | |
| 65 | GEM | 2669 | + | + | + | |
| 66 | HOPX | 84525 | + | + | + | |
| 67 | ITGB5 | 3693 | + | + | + | |
| 68 | KRT6B | 3854 | + | + | + | |
| 69 | NR3C1 | 2908 | + | + | + | |
| 70 | SEPP1 | 6414 | + | + | + | |
| 71 | WIPF1 | 7456 | + | + | + | |
| 72 | PODXL | 5420 | + | + | + | |
| 73 | STK38L | 23012 | + | | + | − |
| 74 | KRT17 | 3872 | + | + | + | |
| 75 | MME | 4311 | + | + | + | |
| 76 | PTHLH | 5744 | + | + | + | − |

A: Genes whose expression in primary tumors is significantly correlated with MAF expression.
B: Genes whose expression in MCF7 cells is modified with the expression of the c-MAF long isoform.
C: Genes whose expression in MCF7 cells is modified with the expression of the c-MAF short isoform.
D: Genes whose expression in MCF7 cells is modified with c-MAF silencing.
+ Increase in expression,
− Decrease in expression.

TABLE 2

Genes whose expression is negatively correlated with c-MAF expression.

| | Gene | Gene ID (Homo sapiens) | A | B | C | D |
|---|---|---|---|---|---|---|
| 77 | CBL | 867 | − | − | − | |
| 78 | CCNI | 10983 | − | − | − | |
| 79 | CCT2 | 10576 | − | − | − | |
| 80 | EIF2S1 | 1965 | − | − | | |
| 81 | EIF3B | 8662 | − | − | | |
| 82 | G3BP1 | 10146 | − | − | | |
| 83 | HNRNPA2B1 | 3181 | − | − | | |
| 84 | HSPD1 | 3329 | − | − | | |
| 85 | IGF1R | 3480 | − | − | − | |
| 86 | MAPK8IP3 | 23162 | − | − | | |
| 87 | MED18 | 54797 | − | − | + | |
| 88 | NOC2L | 26155 | − | − | | |
| 89 | PAFAH1B1 | 5048 | − | − | − | |
| 90 | PCBP2 | 5094 | − | − | | |
| 91 | PCCB | 5096 | − | − | | |
| 92 | PIP5K1A | 8394 | − | − | − | |
| 93 | STIP1 | 10963 | − | − | | |
| 94 | UBE2Z | 65264 | − | − | | |
| 95 | ZNF652 | 22834 | − | − | | |
| 96 | CRABP2 | 1382 | − | | | + |
| 97 | TUBB | 203068 | − | | | + |
| 98 | UPK3B | 80761 | − | | | + |
| 99 | ABHD2 | 11057 | − | − | | |
| 100 | AKAP10 | 11216 | − | − | − | |
| 101 | ANXA9 | 8416 | − | − | | + |
| 102 | BRD2 | 6046 | − | − | − | + |
| 103 | C12orf10 | 60314 | − | − | | |
| 104 | CA12 | 771 | − | − | − | + |
| 105 | DNAJC12 | 56521 | − | − | | |
| 106 | LOC339047 | 339047 | − | − | | |
| 107 | PPDPF | 79144 | − | − | | |
| 108 | UBE2S | 27338 | − | − | | |
| 109 | RERG | 85004 | − | − | − | |

A: Genes whose expression in primary tumors is significantly correlated with MAF expression.
B: Genes whose expression is modified with c-MAF long isoform expression.
C: Genes whose expression is modified with c-MAF short isoform expression.
D: Genes whose expression is modified with c-MAF silencing.
+ Increase in expression,
− Decrease in expression.

Table 1 corresponds to a group of 76 genes characterized by (i) their level of expression is directly correlated with the c-MAF expression level in primary tumor samples and (ii) their level of expression increases when c-MAF expression is induced in breast cancer cell lines or decreases when c-MAF is silenced.

According to the first method of the invention, an increase in expression level of one or more of the genes shown in Table 1 compared to the reference value is indicative that the subject presents a high probability of developing metastasis.

Performed as preferred by the first method of the invention, the expression level of the PTHLH gene is quantified, so that if the expression level of the PTHLH gene is increased compared to the reference value, the subject presents a high probability of developing metastasis. In another preferred performance of the first method of the invention, the expression level of the PODXL gene is quantified, so that if the expression level of the PODXL gene is increased compared to the reference value, the subject presents a high probability of developing metastasis.

Table 2 corresponds to a group of 33 genes characterized by (i) their level of expression is inversely correlated with the c-MAF expression level in primary tumor samples and (ii) their level of expression decreases when c-MAF expression is induced in breast cancer cell lines or increases when c-MAF is silenced in breast cancer cell lines.

According to the first method of the invention, the decrease in expression level of one or more of the genes shown in Table 2 compared to the reference value is indicative that the subject presents a high probability of developing metastasis.

Performed as preferred by the first method of the invention, the expression level of the RERG gene is quantified, so that if the expression level of the RERG gene is decreased compared to the reference value, the subject presents a high probability of developing metastasis.

As an expert in the subject will understand, the quantification of gene expression levels can be determined by measuring the messenger RNA levels of said gene or of the protein encoded by said gene.

For this purpose, the biological sample may be treated to physically or mechanically disaggregate the structure of the tissue or cell, releasing the intracellular components in an aqueous or organic solution to prepare nucleic acids. Nucleic acids are extracted by means of procedures known to an expert in the subject and which are commercially available (Sambroock, J., et al., "Molecular cloning: a Laboratory Manual", 3rd ed., Cold Spring Harbor Laboratory Press, N.Y., Vol. 1-3.)

Thus, the quantification of the expression level of a gene whose expression is modulated in response to an increase in the c-MAF expression level can be performed from the RNA resulting from the transcription of said gene (messenger RNA or mRNA) or, alternatively, from the complementary DNA (cDNA) of said gene. Therefore, in a particular performance of the invention, the quantification of the gene expression levels of a gene whose expression is modulated in response to an increase in the c-MAF expression level involves the quantification of the messenger RNA of said gene, or a fragment of said mRNA, DNA complementary to said gene, or a fragment of said cDNA, or their mixtures.

Practically any conventional method may be used under the context of the invention to detect and quantify the mRNA levels encoded by a gene whose expression is modulated in response to an increase in the c-MAF expression level or its corresponding cDNA. By way of an example, not limitation, the mRNA levels encoded by said gene can be quantified by using conventional methods, for example, methods that involve amplifying the mRNA and quantifying the product of said mRNA amplification, such as electrophoresis and staining, or alternatively, by Southern blot and use of appropriate probes, Northern blot and use of specific probes of the mRNA of the gene of interest modulated by c-MAF or of its corresponding cDNA, mapping with S1 nuclease, RT-LCR, hybridization, microarrays, etc., preferably by real time quantitative PCR using an appropriate marker. Similarly, the levels of the cDNA corresponding to said mRNA encoded by the gene c-MAF can also be quantified using conventional techniques, in this case, the method of the invention includes a step of synthesis of the corresponding cDNA by reverse transcription (RT) of the corresponding mRNA followed by amplification and quantification of the product of said cDNA amplification. Conventional methods of quantifying expression levels can be found, for example, in Sambrook et al., 2001. (Ad cited above).

In a particular embodiment, the quantification of the expression levels of a gene whose expression is modulated in response to an increase in c-MAF expression level is performed using a quantitative polymerase chain reaction (PCR) or DNA or RNA array. Furthermore, quantification of the expression level of a gene whose expression is modulated in response to an increase in the c-MAF expression level may also be performed by quantifying the expression levels of the protein encoded by this gene, or any functionally equivalent variant of the protein. Quantification of the expression level of a gene whose expression is modulated in response to an increase in the c-MAF expression level may also be performed by quantifying the expression levels of any of the isoforms of the protein. Thus, in a particular embodiment, the quantification of the protein levels encoded by a gene whose expression level is modulated in response to an increase in the c-MAF expression level involves the quantification of the protein.

The expression level of a protein may be quantified by using any conventional method that enables said protein to be detected and quantified in a subject's sample. By way of an example, not limitation, the levels of said protein may be quantified, for example, by using antibodies capable of binding to the protein (or fragments thereof containing an antigenic determinant) and subsequently quantifying the complexes formed. The antibodies used in these assays can be labeled or not. Illustrative examples of markers which can be used include radioactive isotopes, enzymes, fluorophores, chemiluminescent reagents, enzymatic substrates or cofactors, enzyme inhibitors, particles, dyes, etc. There is a wide variety of known assays that can be used in the present invention, which use unlabeled antibodies (primary antibody) and labeled antibodies (secondary antibody); these techniques include the Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of biochips or protein microarrays that include specific antibodies or assays based on colloidal precipitation in formats such as dipsticks. Other ways to detect and quantify said protein include affinity chromatography techniques, ligand binding assays, etc. When an immunological method is used, any antibody or reagent can be used that is known to bind to the protein with high affinity to detect the amount thereof. However, the use of an antibody is preferred; for example polyclonal sera, hybridoma supernatants or monoclonal antibodies, antibody fragments, Fv, Fab, Fab'and F (ab') 2, scFv, diabodies, triabodies, tetrabodies and humanized antibodies. There are commercial antibodies against PTHrP or RERG proteins on the market that can be used in the context of the present invention. Specific antibodies for the PTHrP protein include, without limitation, the mouse monoclonal antibody 3H1-5G8 that recognizes human PTHrP by Abcam (ab115488), the rabbit polyclonal antibody P12272 that recognizes rat, mouse and human PTHrP by Abbiotech (catalog number 251478), rabbit polyclonal antibody that recognizes human PTHrP by BioVision (catalog number 5652-100) or the mouse monoclonal antibody that recognizes human PTHrP by Novus Biologicals (catalog number NBP1-26542), among others. Specific antibodies for the RERG protein include, without limitation, goat polyclonal antibodies that recognize human RERG by Santa Cruz (sc-109008 and sc-109009), the rabbit polyclonal antibody that recognizes human, rat and mouse RERG by ProteinTech (10687-1-AP), the rabbit polyclonal antibody that recognizes rat RERG by Abcam (ab115806) and the mouse polyclonal antibody that recognizes human RERG by Novus Biologicals (H00085004-B01).

Specifically in this invention, protein levels are quantified by western blot, ELISA or protein array.

In a second stage, the first method of the invention comprises the comparison of the expression level obtained for genes analyzed in the first stage in relation to the reference range.

After measuring the expression levels of one or more genes, whose expression is modulated in response to an increase in the c-MAF expression levels in a tumor tissue sample of a subject affected by cancer, preferably breast cancer, colon, lung cancer, kidney cancer or thyroid cancer, even more so breast cancer, and comparing to the reference range, if the expression levels of this (these) gene(s) are increased in relation to the reference ranges, then it can be concluded that the subject has a high probability of developing metastasis.

When the first method of the invention is specifically implemented, if the expression level of one or more genes included in Table 1 in a tumor tissue sample of a subject affected by cancer, especially breast cancer, colon cancer, lung cancer, kidney cancer or thyroid cancer, and even more so breast cancer, are increased in relation to the reference range, and/or the expression level of one or more genes included in Table 2 in a tumor tissue sample of a subject affected by cancer, especially breast cancer, colon cancer, lung cancer, kidney cancer or thyroid cancer, and even more so breast cancer, is decreased in relation to the reference range, then the subject has a high probability of developing metastasis.

The determination of the gene expression level, whose expression is modulated in response to an increase in the c-MAF expression levels, needs to be correlated to the reference ranges. Depending on the type of tumor that is under analysis, the exact nature of the reference range may vary. Thus, in the event that the probability of developing metastasis is being determined, then the reference range is derived from the tumor tissue sample of the subject with cancer, especially breast cancer, lung cancer, kidney cancer or thyroid cancer, even more so breast cancer, that has not undergone metastasis or that corresponds to the median value of the expression levels measured in a tumor tissue collected in the biopsy samples of subjects with cancer, especially breast, lung, kidney or thyroid cancer, even more so breast cancer, that have not developed metastasis.

This reference sample is obtained typically by combining equal amounts of samples from a subject population. The typical references samples are generally obtained from subjects who are clinically well-documented and from those in which the absence of metastasis is well-defined. In such samples, normal (reference) concentrations of the biomarker may be determined, for example by providing the average concentration on the reference population. Upon determining the reference concentration of the marker, several considerations are taken in to account. Amongst these considerations are age, weight, sex, the patient's general physical condition, etc. For example, equal amounts from a group of at least 2, at least 10 to preferably more than 100 to more than 1000 subjects are taken as a reference group, preferably classified according to the previous considerations, for example various age categories. The samples collection resulting from the reference level will be preferably made up of subjects with the same type of cancer as the patient under study.

Once the median value is established, the level of this marker in the patients' tumor tissues can be compared with this median value, and in this way can be assigned to the "increased" expression level. Due to the variability amongst subjects (for example, aspects regarding age, race, etc.) it is very difficult (if not virtually impossible) to establish absolute reference ranges of a gene expression. Therefore, specifically in this invention, the reference range for "increased" or "decreased" expression of a gene expression whose expression is modulated in response to an increase in the c-MAF expression levels are determined by calculating the percentiles through conventional means that involves assaying, in one or several isolated samples in which the disease is well-documented by any of the aforementioned methods, the gene expression levels whose expression is modulated by c-MAF. The "reduced" levels can then be assigned, preferably, to samples in which the expression levels are equal to or less than the 50 percentile in the normal population, including, for example, expression levels equal to or less than the 60 percentile in the normal population, equal to or less than 70 percentile in the normal population, equal to or less than 80 percentile in the normal population, equal to or less than 90 percentile in the normal population, equal to or less than 95 percentile in the normal population. The "increased" expression levels can then be assigned, preferably, to samples where the expression levels are equal to or exceed the 50 percentile in the normal population, including, for example, expression levels equal to or in excess of the 60 percentile in the normal population, equal to or in excess of the 70 percentile in the normal population, equal to or in excess of the 80 percentile in the normal population, equal to or in excess of the 90 percentile in the normal population, equal to or in excess of the 95 percentile in the normal population Specifically in the invention, the cancer is selected from the grouped formed by breast cancer, colon cancer, lung cancer, kidney cancer and thyroid cancer. The preferred cancer in the invention is breast cancer. And even more preferred is any type of ER+ or triple negative breast cancer When the first method of the invention is implemented, the preferred metastasis in a subject affected by cancer, especially breast cancer, colon cancer, lung cancer, kidney cancer or thyroid cancer, even more so breast cancer, is bone metastasis. When the first method of the invention is implemented, the metastasis even more preferred in a subject affected by cancer, especially breast cancer, colon cancer, lung cancer, kidney cancer or thyroid cancer, even more so breast cancer, is osteolytic bone metastasis Design Method for Personalized Therapy for a Subject Affected by Cancer, Especially Breast Cancer As the state of the art is known, treatment administered to a subject that suffers cancer, such as breast cancer, colon cancer, lung cancer, kidney cancer or thyroid cancer, may vary based on there being associated a high probability of developing metastasis. In cases in which the probability of having metastasis is high, the treatment of choice includes a systemic treatment like chemotherapy.

Therefore, according to what is explained in this invention, given that the alteration of expression levels of one or more genes whose expression is modulated in response to an increase in the c-MAF expression levels is related to the probability of developing metastasis, the determination of the levels of these modulated genes by c-MAF helps to make decisions in regards to the most suitable therapy for the subject who has cancer.

Thus, in other aspects the invention is related to an in vitro method (hereinafter, second method of the invention) to design a personalized therapy for a subject affected by cancer, especially breast cancer, colon cancer, lung cancer, kidney cancer or thyroid cancer, and more so breast cancer, that involves determining the expression level in a tumor tissue sample of the subject of one or more genes whose expression is modulated in response to an increase in the c-MAF expression levels in which the alternated expression levels of one or more gene in relation to the reference range are indicative that the subject is susceptible to receiving therapy aimed at preventing metastasis.

The second method of the invention involves, in a first stage, quantifying the expression level of a tumor tissue sample of a subject affected by cancer, especially breast cancer, colon cancer, lung cancer, kidney cancer or thyroid cancer, and even more so breast cancer, of one or more genes whose expression is modulated in response to an increase in the c-MAF expression levels.

When the second method of the invention is specifically implemented, the gene or genes whose expression is modulated in response to an increase in the c-MAF expression levels is selected from a group formed from the genes included in Table 1 and/or one or more of the genes included in Table 2 in a tumor tissue sample of the subject, where if the expression levels of one or more of the genes from Table 1 are increased in relation to the reference range and/or the expression levels of one or more genes from Table 2 are decreased in relation to the reference range, then the subject is susceptible to receiving therapy to prevent metastasis.

When the second method of the invention is implemented, the preferred expression level of the PTHLH gene is quantified, so that if the PTHLH gene expression level is increased in relation to the reference range, the subject is susceptible to receiving the therapy aimed at preventing metastasis.

When the second method of the invention is implemented, the preferred expression level of the PODXL gene is quantified, so that if the PODXL gene expression level is increased in relation to the reference range, the subject is susceptible to receiving the therapy aimed at preventing metastasis.

When the second method of the invention is implemented, the preferred expression level of the RERG gene is quantified, so that if the RERG gene expression level is decreased in relation to the reference range, the subject is susceptible to receiving the therapy aimed at preventing metastasis.

When the second method of the invention is specifically implemented, the cancer is selected from a grouped formed by breast cancer, colon cancer, lung cancer, kidney cancer or thyroid cancer, is preferably breast cancer, When the second method of the invention is even more specifically implemented, breast cancer may be any type of ER+ or ER−HER2− (ER−HER2−PR+ o ER−HER2−PR−) breast cancer.

When the second method of the invention is specifically implemented, the metastasis is a bone metastasis. When the second method of the invention is even more specifically implemented, the bone metastasis is osteolytic metastasis.

In the case of the second method of the invention, the sample is a primary tumor tissue sample of the subject.

In a second stage, the expression of one or more genes whose expression is modulated in response to an increase in the c-MAF expression levels in the subject's tumor sample is compared in relation to the reference range. This reference range is obtained from the expression level in a control sample of the gene whose expression is modulated in response to an increase in the c-MAF expression levels. Depending on the type of tumor under analysis, the exact nature of the control sample may vary. Thus, the preferred control sample is a tumor tissue sample of the subject with breast cancer, colon cancer, lung cancer, kidney cancer or thyroid cancer that has not undergone metastasis. And even more preferred for the control sample is a tumor tissue sample of the subject with ER+ breast cancer who has not developed metastasis. Alternatively, the reference range corresponds to the median of the c-MAF expression levels measured in tumor tissue samples collected in biopsies of subjects with cancer, particularly breast cancer, colon cancer, lung cancer, kidney cancer or thyroid cancer, even more so ER+ breast cancer, who have not developed metastasis.

In a second stage of the second method of the invention, the expression levels obtained in the tumor tissue simple of the subject affected by cancer, especially breast cancer, colon cancer, lung cancer, kidney cancer or thyroid cancer, even more so breast cancer, for one or more genes whose expression is modulated in response to an increase in c-MAF expression levels are compared to the reference range, so that if the expression levels of one or more of these genes are altered in relation to the reference range, then it can be concluded that the subject is susceptible to receiving therapy aimed at preventing (if the subject has not yet developed metastasis) and/or treating metastasis (if the subject has already developed metastasis).

When the cancer has caused metastasis, systemic treatments including, but not limited to, chemotherapy, hormone treatment, immunotherapy, or a combination of these. Additionally, radiotherapy and or surgery can be used. The choice of treatment generally depends on the type of primary cancer, the size, localization of the metastasis, age, the patient's general state of health and type of treatments previously used.

Treatments aimed at preventing and/or treating metastasis in a subject with cancer, such as breast cancer, include chemotherapy, hormone therapy and immunotherapy.

Chemotherapy is the use of drugs to kill cancer cells. Amphetamines are typically taken orally or intravenously. On occasions, chemotherapy is used together with radiation treatment. Suitable chemotherapy treatment for breast cancer includes, but not limited to, anthracyclines (doxorubicin, epirubicin, pegylated, liposome-encapsulated doxorubicin), taxanes (paclitaxel, docetaxel, nanoparticle albumin-bound paclitaxel), 5-fluorouracil, Vinca alkaloids (vinorelbine, vinblastine), Gemcitabine, platinum salts (cisplatin, and carboplatin), cyclophosphamide, etoposide and regimen combinations of one or more of the above such as cyclophosphamide-anthracycline +/− 5-fluorouracil (for example, doxorubicin-cyclophosphamide (AC), epirubicin-cyclophosphamide, (EC) cyclophosphamide-epirubicin-5-fluorouracil (CEF), cyclophosphamide-doxorubicin-5-fluorouracilo (CAF), 5-fluorouracil-epirubicin-cyclophosphamide (FEC)), cyclophosphamide-methotrexate-5-fluorouracil (CMF), anthraciclines-taxanes (for example, doxorubicin-paclitaxel or doxorubicin-docetaxel), Docetaxel-capecitabine, Gemcitabine-paclitaxel, Taxane-platinum salts (for example, paclitaxel-carboplatin or docetaxel-carboplatin).

Hormone therapy is based on the fact that some hormones promote the growth of some cancers. For example, estrogen in women, which is produced by the ovaries, sometimes promote the growth of breast cancer. There are various ways to stop the production of these hormones. One way is by surgically removing the organs producing them: the ovaries in the case of women, the testicles in the case of men. More often drugs can be used to prevent these organs from producing hormones or to prevent the hormones from acting on the cancer cells.

Immunotherapy is a treatment that helps the immune system itself to combat the patient's cancer. There are several types of immunotherapy that is used to treat patients with metastasis. These include, but not limited to, cytokines, monoclonal antibodies and antitumor vaccines.

Therapeutic Methods Based on Inhibiting Genes whose Expression is Positively Correlated to the c-MAF Expression The authors of this invention have stated that the inhibition of PHTLH in a bone metastatic colonization model caused by a xenograft of the breast tumor results in a decrease in the number of osteolytic lesions within the metastasis. This indicates that the genes whose expression increases in response to the increase in c-MAF expression in a breast tumor (or whose expression decreases in response to a decrease in c-MAF expression in a breast tumor) are causal target genes in bone metastasis processes from ER+ breast cancer and, therefore, inhibiting it may be useful to stopping the appearance of breast cancer metastasis.

On the other hand, the authors of this invention has functionally validated the correlation of the expression of the metastatic gene PODXL in an assay of adhesion to bone marrow cells in an experimental model based on purified mouse bone marrow cells (Example 5). The PODXL expression was reduced in vivo in highly metastatic bone cells, MCF7, which shows high expression levels of the c-MAF responsible for the increase of the endogenous levels of the PODXL gene Therefore, this gene is valued as a prognostic marker and causal target gene in bone metastatic processes in ER+ breast cancer and as part of the bone metastasis program mediated by c-MAF.

Therefore, in other aspects, the invention is related to the use of an agent that inhibits the expression of a gene or the gene product activity for the preparation of a drug for treating and/or preventing metastatic cancer, especially breast cancer, colon cancer, lung cancer, kidney cancer or thyroid cancer, even more so breast cancer, in which the gene is characterized by its expression in tumor cells, especially those found in the breast, colon, lung, kidney or thyroid, even more so in the breast, increases in response to an increase in the c-MAF expression levels in these cells or decrease in response to a decrease in the c-MAF expression levels in these cells.

In another aspect, the invention is related to an agent that inhibits the expression of a gene or gene product activity for use in treating and/or preventing metastatic cancer, especially breast cancer, colon cancer, lung cancer, kidney cancer or thyroid cancer, even more so breast cancer, in which the gene is characterized by its expression in tumor cells, especially those found in the breast, colon, lung, kidney or thyroid, even more so in the breast, increases in response to an increase in the c-MAF expression levels in these cells or decrease in response to a decrease in the c-MAF expression levels in these cells.

In another aspect, the invention is related to a method for treating and/or preventing metastatic cancer, especially breast cancer, colon cancer, lung cancer, kidney cancer or thyroid cancer, even more so breast cancer, in a subject that involves administering an agent that inhibits gene expression or the gene product activity which is characterized by its expression in tumor cells, especially those found in the breast, colon, lung, kidney or thyroid, even more so in the breast, increases in response to an increase in the c-MAF expression levels in these cells or decrease in response to a decrease in the c-MAF expression levels in these cells.

The expression "an agent that inhibits gene expression" refers to any molecule that is capable of producing a decrease of gene transcription, destabilizing mRNA and/or decreasing mRNA translation.

Inhibitor agents of the expression can be identified by standard methods in order to determine the ability of a compound to inhibit the transcription of a certain gene (RT-PCR, Northern blot and hybridization, run-on assays, etc.), to destabilize the mRNA or inhibit the translation of mRNA (in vitro translation assays in reticulocyte lysates or wheat germ lysate). In this invention, it is considered that a compound is an inhibitor of gene expression when it is capable of decreasing the amount of mRNA of the gene, decreasing the transcription of the gene and/or the translation of the gene of at least 10%, at least 20%, at least 30%, at least 40%, at least 50%, at least 60%, at least 70%, at least 80%, at least 90% or a 100% decrease (complete inactivation of this product of expression)

Examples of inhibitor agents of gene expression for use in this invention include, but not limited to, gene-specific antisense oligonucleotides, gene-specific interference RNA (siRNA) and gene-specific catalytic RNA or ribozymes.

The preferred inhibitor agent for gene expression for use in this invention is a gene-specific antisense oligonucleotide.

The agent also preferred for inhibiting gene expression is a gene-specific interfering RNA. Small interfering RNA or siRNA are agents capable of inhibiting target gene expression through RNA interference. siRNA can be chemically synthesized, can be obtained through transcription in vitro or can be synthesized in vivo in the target cell. Typically, siRNA consists of a double-stranded RNA between 15 and 40 nucleotides of length and can contain a 3' and/or 5' protruded region of 1 to 6 nucleotides. The length of the protruded region is independent of the total length of the siRNA molecule. siRNAs act through the degradation or post-transcriptional silencing of the target messenger.

The invention's siRNAs are substantially homologous to mRNA of the gene that encodes PTHLH, to the gene that encodes PODXL, or to the genomic sequence that encodes the protein. By "substantially homologous" it is understood that they have a sequence that is sufficiently complementary or similar to the target mRNA, in a way that the siRNA is able to cause the degradation of the target mRNA by way of interference RNA. siRNAs suitable for causing this interference include siRNA formed by RNA, as well as siRNA that contain different chemical modifications such as:

- siRNA in which the link between nucleotides are different from those that appear in nature, such as phosphorothioate links.
- conjugates of the RNA chain with a functional reactive, such as fluorophore.
- Modifications of the end of the RNA chains, particularly 3' end through modification with different functional 2'-position hydroxyl groups.
- Nucleotides with modified sugars such as O-alkylated remains at position 2' such as 2'-O-methyl ribose p 2'-O-fluoro ribose
- Nucleotides with modified bases such as halogenated bases (for example, 5-bromouracil and 5-iodouracil), alkylated bases (for example 7-methylguanosine).

siRNAs can be used as is, meaning in the form of double strain RNA with the abovementioned characteristics. Alternatively, it is possible to use vectors that contain sense and antisense chains of the siRNAs under the control of the promoters suitable for expression in the cell of interest.

Vectors suitable for siRNA expression are those in the two regions of DNA that encode for the two chains of siRNA that are arranged in tandem in one single DNA chain separated by a separating region that, upon transcription, forms a loop and where a single promoter guides the transcription of the DNA molecule that gives rise to the shRNA.

Alternatively, it is possible to use vectors in which each one of the chains that form the siRNA is formed from the transcription of a different transcription unit. These vectors in turn divide into convergent and divergent transcription vectors. In divergent transcription vectors, the transcription units that encode each one of the DNA chains that form the siRNA are localized in tandem in a vector in a way that the transcription of each DNA chain depend on its own proper, that can be equal or different (Wang, J. et al., 2003, Proc. Natl. Acad. Sci. USA., 100:5103-5106 y Lee, N. S., et al., 2002, Nat. Biotechnol., 20:500-505). In convergent transcription vectors, the DNA regions that give rise to the siRNA are found forming sense and antisense chains of the DNA region that is flanked by two inverted promoters. Following the transcription of the sense and antisense RNA chains, the chains will form the hybrid to form a functional siRNA. Vectors have been described as inverted promoter systems in those that use 2 U6 promoters, (Tran, N. et al., 2003, BMC Biotechnol., 3:21), a mouse U6 promoter and a human H1 promoter (Zheng, L., et al., 2004, Proc.Natl. Acad. Sci. USA., 135-140 y WO2005026322) and a human U6 promoter and a mouse H1 promoter (Kaykas, A. y Moon, R., 2004, BMC Cell Biol., 5:16).

Promoters suitable for use in the siRNA expression from convergent and divergent vectors include any promoter or pair of promoters compatible with the cells in which it is desired to express siRNAs. Thus, promoters suitable for the development of this invention include, but not necessary limited to, constitutive promoters such as those from genomes of eukaryotic viruses such as polyomavirus, adenovirus, SV40, CMV, avian sarcoma virus, hepatitis B virus, metallothionen promotor gene, herpes simplex virus thymidine kinase promotor, LTR regions of the retroviruses, immungloblulin promoter, actin promoter, EF-1 alpha promoter as well as inducible promoters in which expression of protein depends on the addition of a molecule or an exogenous signal, such as the tetracylcine system, NF-kB and UV light system, Cre-lox system, heat shock promoter, RNA polymerase II regulating promoters described in WO/2006/135436 as well as tissue-specific promoters (for example, the PSA promoter described in WO2006012221). RNA polymerase III promoters that act constitutively are the preferred promoters for this invention. RNA polymerase III promoters appear in a limited number of genes such as 5S RNA, tRNA, 7SL RNA and U6 snRNA. Unlike other RNA polymerase III promoters, the type III promoters do not require any intragenic sequence but need 5' direction sequences that include a TATA box at positions −34 and −24, a proximal sequence element (PSE) between 66− and −47 and, in some cases, a distal sequence element (DSE) between the positions −265 and −149. RNA polymerase III type III are the preferred promoters of human or murine H1 and U6 genes. Even more preferred are 2 human or murine U6 promoters, a mouse U6 promoter and a human H1 promoter or a human U6 promoter and a mouse H1 promoter. In the context of this invention, promoters especially suitable and therefore preferred for specifically expressing genes of interest in breast tumors, preferably in ER+ breast tumors, are the alpha ER or Cyclin D1 promoters.

siRNAs can be generated intracellularly from the so-called shRNA (short hairpin RNA), characterized by the antiparallel chains that form the siRNA that are connected by loop or hairpin region. siRNAs can be coded by plasmids or viruses, particularly retroviruses and is under the control of a promoter. Promoters suitable for expressing shRNA are the ones indicated in the previous paragraph for siRNA expression.

Vectors suitable for siRNA and shRNA expression include prokaryotic expression vectors such as pUC18, pUC19, pBluescript and derivatives, mp18, mp19, pBR322, pMB9, ColE1, pCRI, RP4, phages and shuttle vectors such as pSA3 and pAT28, yeast expression vectors such as 2-micron plasmids, integration plasmids, YEp vectors, centromeric plasmids and similar vectors, expression vectors in insect cells such as pAC series and pVL series vectors, expression vectors in plant cells such as pIBI series, pEarleyGate, pAVA, pCAMBIA, pGSA, pGWB, pMDC, pMY, pORE and similar vectors and large eukaryotic cell expression vectors based on viral vectors, (adenovirus, viruses associated with the adenoviruses as well as retroviruses and, in particular, lentiviruses) as well as non-viral vectors such as pcDNA3, pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and pKSV-10, pBPV-1, pML2d and pTDTI. Lentiviral vectors are the vectors preferred for development siRNAs and shRNAs of the invention can be obtained by using a series of technique known by the expert in the field. The nucleotide sequence region that is used as a base to design siRNAs is not limited and may contain a region of the encoding sequence (between the start codon and end codon) or, alternatively, it may contain sequences of the 5' or 3' untranslated region, preferably between 25 and 50 nucleotides long and any position in the sense 3' position in relation to the start codon. A way of designing a siRNA involves identifying the AA(N19)TT motifs, in which N can be any nucleotide in the gene sequence, especially PTHLH or PODXL, and the selection of those that has a high GC-content. If no such motif is found, it is possible to identify the NA(N21), in which N can be any nucleotide.

A gene-specific DNA enzyme is the preferred agent for inhibiting gene expression. DNA enzymes incorporate some of the mechanical characteristics of the antisense technology and ribozymes. DNA enzymes are designed to recognize a target sequence of a particular nucleic acid, similar to antisense oligonucleotide, but like the ribozyme they are catalytic and specifically cleave the target nucleic acid.

The agent preferred to inhibit gene expression is a ribozyme designed to catalytically cleave transcripts of target mRNA to prevent the translation of mRNAs that encode PTHLH or PODXL whose inhibited activity is desired. Ribozymes are RNA enzyme molecules capable of catalyzing the specific cleavage of RNA. (For review, see, Rossi, Current Biology 4: 469-471, 1994). The ribozyme action mechanism involves specific molecule sequence hybridization to a complementary target RNA, followed by an endonucleolytic cleavage event. The composition of ribozyme molecules preferably includes one or more complementary sequences to the target mRNA, and the well-known sequence responsible for the mRNA cleavage or a functionally equivalent sequence (see for example U.S. Pat. No. 5,093,246).

Ribozymes used in this invention include hammerhead ribozymes, endoribonuclease RNA (hereinafter, "Cech ribozymes" (Zaug et al., Science 224:574-578, 1984.

Ribozymes can be composed of modified oligonucleotides (for example, to improve stability, guidance, etc.) and should be distributed to cells that express in vivo the target gene. A preferred distribution method involves using a DNA construction that "encodes" the ribozyme under the control of a strong pol III or pol II constitutive promoter, in a way that the transfected cell will produce sufficient quantities of ribozyme to destroy endogenous target messengers and inhibit translation. Since ribozymes, unlike other antisense molecules, are catalytic, they require little intracellular concentration to be effective.

In the case of compounds that inhibit the activity of a gene product, these compounds can be identified by using specific assays that are capable of determining the activity of such product. As preference, the compounds inhibiting the activity of the gene product can be identified by using the assay explained in example 3 of this invention characterized based on the determination of the capability of the inhibitor agent to decrease the formation of osteolytic lesions and/or differentiate osteoclasts in vitro metastatic lesion in an animal model of breast cancer metastasis with high capability of metastatic colonization. In this invention, it is considered that a compound is an inhibitor of the activity of an gene product when it is capable of decreasing the activity of such product by at least 10%, at least 20%, at least 30%, at least 40%, at least 50%, at least 60%, at least 70%, at least 80%, at least 90%, or a 100% decrease (complete inactivation of the gene product)

Examples of agents that inhibit the gene product activity for use in this invention include, but are not limited to, specific inhibitor antibodies for the gene product, negative dominant variants of the gene product and inhibitory peptides of the gene product.

Another preferred agent that inhibits the gene product activity is a specific inhibitor antibody for this product. The antibodies can be prepared by using any of the methods known by experts in the field, some of which have been previous stated. Thus, polyclonal antibodies are prepared by way of immunization of an animal with the protein of which inhibition is desired. Monoclonal antibodies is prepared by using the method described by Kohler, Milstein and et. al. (Nature, 1975, 256: 495). Suitable antibodies in the context of this invention include intact antibodies that include a variable region of binding antigen and a constant region, Fab, F(ab')2 and Fab' fragments, Fv, scFv, nanobodies, diabodies and bispecific antibodies. After the antibodies have been identified with the protein-binding ability, particularly to PTHLH or PODXL, those capable of inhibiting the activities of this protein will be selected by using an assay for identifying agent inhibitors.

Another preferred agent for inhibiting gene product activity is an inhibitory peptide of the product.

Another preferred agent for inhibiting gene product activity is a "negative dominant mutant" of this gene product. The invention considers the use of negative dominant mutants of a gene product as well as the polynucleotides that encode the mutants. The promoters that can be used to regulate the transcription of the polynucleotide of the invention can be constitutive promoters, meaning they can basically guide the transcription or inducible promoters in which transcription activity requires an external signal. Suitable constitutive promoters for the regulation of transcription are, amongst others, the CMV promoter, SV40 promoter, DHFR promoter, mouse mammary tumor virus (MMTV) promoter, elongation faction 1a (EF1a) promoter, albumin promoter, ApoA1 promoter, keratin promoter, CD3 promoter, heavy- or light-immunoglobulin chain promoter, neurofilament promoter, neuron-specific enolase promoter, L7 promoter, CD2 promoter, myosin light-chain promoter, HOX promoter, thymidine kinase promoter, RNA Polymerase II promoter, MyoD promoter, phosphoglycerokinase (PGK), low density lipoprotein promoter, actin promoter. The preferred promoter that regulates the transactivator expression is the PGK promoter. The promoter preferred to regulate polynucleotide transcription of the invention is the phage T7 RNA polymerase Preferably, the inducible promoters that can be used in the context of this invention are those that respond to an inductor agent, that shows no or insignificant basal expression in absence of an inductor agent and that are able to promote the activation of the gene localized in position 3'. Based on the type of inductor agent, the inducible promoters are classified as Tet on/off promoters (Gossen, M. y H. Bujard (1992) Proc. Natl. Acad. Sci. USA, 89:5547-5551; Gossen, M. et al., 1995, Science 268:1766-1769; Rossi, F. M. V. y H. M. Blau, 1998, Curr. Opin. Biotechnol. 9:451-456); Pip on/off promoters (US6287813); antiprogestin-dependent promoters (US2004132086), ecdysone-dependent promoters (Christopherson et al., 1992, Proc. Natl. Acad. Sci. USA, 89:6314-6318; No et al., 1996, Proc. Natl. Acad. Sci. USA, 93:3346-3351, Suhr et al., 1998, Proc. Natl. Acad. Sci. USA, 95:7999-8004 y WO9738117), un metallothionen-dependent promoter (WO8604920) y rapamycin-dependent promoter (Rivera et al., 1996, Nat.Med. 2:1028-32).

Vectors suitable for the expression of the polynucleotide that encodes the dominant-negative variants [sic: variant] of c-MAF include vectors derivative of expression vectors in prokaryotes such as pUC18, pUC19, Bluescript and its derivatives, mp18, mp19, pBR322, pMB9, ColEl, pCRa, RP4, phages and "shuttle" vectors such as pSA3 and pAT28, expression vectors in yeast such as 2 micron plasmid vectors, integration plasmids, YEp vectors, centromeric and similar plasmids, insect cell expression vectors such as pAC and pVL series vectors, plant expression vectors such as pIBI, pEarleyGate, pAVA, pCAMBIA, pGSA, pGWB, pMDC, pMY, pORE series vectors and similar, and expression vectors in higher eukaryotic cells either based on viral vectors (adenovirus or viruses associated with it, such as retrovirus, and lentivirus in particular) as well as non-viral viruses such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, pTracer-HCMV, pUB6/V5-His, pVAX1, pZeoSV2, pCI, pSVL and pKSV-10, pBPV-1, pML2d and pTDT1.

In a preferred embodiment, the gene whose expression is increased in response to an increase in the c-MAF expression levels in a tumor, especially in a breast, colon, lung, kidney or thyroid tumor, more particularly breast, or whose expression is decreased in response to a decrease in the expression levels of c-MAF in a tumor, especially breast, colon, lung, kidney or thyroid cancer, more particularly breast, the genes described in Table 1 are selected.

In an even more preferred embodiment, the gene whose expression is increased in response to an increase in the c-MAF expression levels in a breast tumor is PHTLH gene. In an alternative preferred embodiment, the gene whose expression is increased in response to an increase in the c-MAF expression levels in a breast tumor is the PODXL gene.

Thus, agents that inhibit PHTHL expression or expression product activity of the gene include, but are not limited to, a specific siRNA for the PHTHL gene, a specific antisense oligonucleotide for the PHTHL gene, a specific ribozyme for the PHTHL gene, a specific antibody inhibitor for the PHTHL protein, a dominant-negative PHTHL variant of said expression product and a PHTHL inhibitor peptide.

Inhibitor agents of the PODXL expression or of the expression product activity of the gene include, but are not limited to, a specific siRNA for the PODXL gene, a specific antisense oligonucleotide for the PODXL gene, a specific ribozyme for the PODXL gene, specific inhibitor antibody for the PODXL protein, a PODXL dominant-negative variant of the expression product and a PODXL inhibitor peptide.

PTHLH-specific siRNAs include, but are not limited to, commercially available siRNAs such as Abgent's predesigned siRNA for PTHLH (catalog No. R114318) Qiagen's siRNA for mouse PTHLH (GS19227), Cambridge Bioscience's siRNA duplex for human PTHLH (catalog No. SR303874), among others.

PODXL-specific siRNAs include, but are not limited to, commercially available siRNAs such as Santa Cruz Biotechnology's sc-44765 siRNA, OriGene's siRNA duplexes for human PODXL (SR303611), or Cambridge Bioscience's siRNA duplexes for human PODXL (catalog #SR303611), among others.

PTHLH inhibitor antibodies effective for the use in the present invention include, but are not limited to, Abcam's 3H1-5G8 mouse monoclonal antibody which recognizes human PTHLH (ab115488), Abbiotech's P12272 rabbit polyclonal antibody which recognizes rat, mouse and human PTHLH (catalog number 251478), BioVision's rabbit polyclonal antibody which recognizes human PTHLH (catalog number 5652-100), or Novus Biologicals' mouse monoclonal antibody which recognizes human PTHLH (catalog number NBP1-26542), among others.

PODXL inhibitor antibodies effective for the use in the present invention include, but are not limited to, the ab62594 rabbit polyclonal antibody which recognizes the N-terminal region of human PODXL, or the sc-23903 mouse monoclonal antibody which recognizes human PODXL by Santa Cruz Biotechnology.

PTHLH inhibiting peptides include, but are not limited to:
PTHLH truncated variants such as hPTHrP (7-34) with sequence LLHDKGKSIQDLRRRFFLHHLIAEIHTA (SEQ ID NO: 8), PTHrP (3-34), PTHrP (8-34), PTHrP (9-34), PTHrP (10-34) as well as amidated variants and variants resulting from the substitution of amino acids corresponding to PTHLH positions 10, 11 and 12 by Asn (Asn10 variants), Leu (Leu11 variants) and D-Trp (D-Trp12 variants), respectively and in particular, the peptides [Nle$^{8,18}$, Tyr$^{34}$]bPTH (7-34)NH$_2$, [Tyr$^{34}$] bPTH (7-34) NH$_2$, hPTHrP (7-34), [Leu$^{11}$, D-Trp$^{12}$] hPTHrP(7-34)$_2$, [Asn$^{10}$Leu$^{11}$]hPTHrP (7-34)-NH$_2$ and [Asn$^{10}$, Leu$^{11}$, D-Trp $^{12}$] hPTHrP(7-34)-NH$_2$ as described in Nutt et al., 1990, Endocrinology 127:491-493, Doppelt et al., 1986, Proc. Natl. Acad. Sci. USA 83:7557-7560 and U.S. Pat. Nos. 6,362,163 and 5,527,772).
TIP (tuberoinfundibular peptide) truncated derivatives as the TIP peptide (1-39) (tuberoinfundibular peptide 1-39), and derivatives thereof as described in Hoare et al, Peptides 23: 989-998, 2002).
peptide NCT00051779 (Chugai Pharmaceuticals)
Peptides described in US2007203071AA Tables 1 to 5
Peptides whose structure is shown in WO04103273A2 formula 1 of
Peptides described by Olstad et al. (Peptides 1995, 16:1031-1037) and Roubini et al. (Biochemistry, 1992, 31: 4026-4033)
Peptides [Asn10Leu11]-PTHrP(7-34)-NH2 and [Asn10, leu11, D-Trp12]-PTHrP-(7-34)-NH2 described by Nutt et al. (Endocrinology, 1990, 127:491-3)
Fc conjugates of any of the foregoing peptides, such as those described in WO04060386 peptides.

Functionally equivalent variants of these peptides.

By the term "functionally equivalent variant", as used in the present invention, are those peptides derived from the sequence of a peptide of the invention by modification, insertion and/or deletion of one or more amino acids, provided that the function of said peptide is maintained at least at 20%, at least 50%, at least 80%, with respect to the function of the corresponding peptide of the invention without modifications, insertions and/or deletions. Variants suitable for use in the present invention include those variants which exhibit at least 25%, at least 40%, at least 60%, at least 70%, at least 80%, at least 90%, at least 95%, at least 96%, at least 97%, at least 98% or at least 99% sequence identity with respect to the above mentioned peptide sequence. The degree of identity between two amino acid sequences can be determined by conventional methods, for example by standard alignment algorithms of known sequences in the prior art, such as, for example, BLAST (Altschul S F et al. Basic Local Alignment Search Tool. J Mol Biol. 1990 Oct. 5; 215(3):403-10).

Other PTHLH inhibitors include, but are not limited to, polypeptides that bind specifically to the PTHLH N-terminal region as described in WO2011003935.

In a particular form of the first use of the invention, the cancer is a cancer of the breast, colon, lung, kidney or thyroid cancer, preferably breast cancer.

In an even more particular form of the second use of the invention, the breast cancer is ER+ type or triple negative type.

In a particular form of the uses of the invention, cancer metastasis, particularly breast, colon, lung, kidney or thyroid cancer, preferably breast cancer, is bone metastasis. In an even more particular form, the bone metastasis is osteolytic metastasis.

Therapeutic Methods Based on Gene Activation with an Expression Inversely Correlated with c-MAF Expression.

The authors of the present invention have shown that the RERG gene expression levels are inversely correlated with the c-MAF expression levels and that an increase in the breast tumor RERG expression is capable of reducing the number of metastatic cells. Therefore, this demonstrates that the modulation of expression of genes whose expression is down-regulated by c-MAF can be used for the treatment and/or prevention of breast cancer metastasis. In this case, the author has shown, that use of an RERG activating agent is capable of reducing the number of metastatic cells.

Therefore, in one aspect, the invention relates to the use of an agent that stimulates the expression of a gene or activity of the expression product of said gene for the preparation of a medicament for the treatment and/or prevention of cancer metastasis, particularly breast, colon, lung, kidney or thyroid, more particularly breast cancer, wherein said gene is characterized in that its expression in tumor cells, in particular that of breast, colon, lung, kidney or thyroid cancer, more particularly breast, decreases in response to an increase in the expression levels of c-MAF in said cells or because its expression increases in response to a decrease in expression levels of c-MAF in said cells.

In another aspect, the invention relates to an agent that stimulates the expression of a gene or activity of the expression product of this gene for use in the preparation of a medicament for the treatment and/or prevention of cancer metastasis, in particular breast, colon, lung, kidney or thyroid cancer, more particularly breast cancer, wherein said gene is characterized in that its expression in tumor cells, in particular that of breast, colon, lung, kidney or thyroid cancer, more particularly breast, decreases in response to an increase in the expression levels of c-MAF in said cells or because its expression increases in response to a decrease in the expression levels of c-MAF in these cells.

In another aspect, the invention relates to method for the treatment and/or prevention of cancer metastasis, particularly breast, colon, lung, kidney or thyroid cancer, more particularly breast cancer, in a subject including the administering to said subject an agent that stimulates expression a gene or activity of the expression product of said gene wherein said gene is characterized because its tumor cell expression, in particular that of breast, colon, lung, kidney or thyroid cancer, more particularly breast, decreases in response to an increase in the expression levels of c-MAF in said cells or because its expression increases in response to a decrease in the expression levels of c-MAF in said cells.

In a preferred embodiment, the agent that stimulates the expression of said gene is a polynucleotide containing the coding sequence of said gene or wherein the agent that stimulates the activity of the expression product of said gene is a polypeptide encoded by said gene.

In another aspect, the polynucleotide that stimulates expression of this gene may become a part of a gene construct. Preferably, the gene constructs contain the polynucleotide of the invention together with regions suitable for regulating expression of the polynucleotide including promoters, transcription terminators, untranslated 5' and 3' regions, polyadenylation signals and similar.

In principle, any promoter can be used for cloning vectors in the context of the present invention provided the promoters are compatible with the cells in which it is desired to express the polynucleotide. Thus, promoters suitable for the embodiment of the present invention include but are not necessarily limited to, constitutive promoters such as the derivatives of the genomes of eukaryotic viruses such as polyoma virus, adenovirus, SV40, CMV, avian sarcoma virus, hepatitis B virus, the metallothionein gene promoter, the herpes simplex virus thymidine kinase gene promoter, LTR regions of retroviruses, the inmunoglobuina [sic: immunoglobulin] gene promoter, the actin gene promoter, the EF-1alpha gene promoter as well as inducible promoters in which the expression of the protein depends on the addition of a molecule or of an exogenous signal, such as the tetracycline system, the NFκB/UV light system, the Cre/Lox system and heat shock gene promoters, regulatable RNA polymerase II promoters as described in WO/2006/135436.

In a preferred embodiment, the polynucleotide is operably coupled to a breast tissue-specific promoter. Examples of suitable specific promoters of breast tissue for use in the present invention include, illustratively:

The stromelysin 3 promoter (Basset et al, Nature 348.: 699,1990)

The promoter of the mucin-like glycoprotein (DF3, MUCI) ((Abe et al. Proc. Natl. Acad. Sci. USA 90: 282,1993)

c-erbB-3, c-erbB-2 or c-erbB-4 promoters

The promoter of the mouse mammary tumor virus (MMTV),

The promoter of the whey acidic protein

The human α-lactalbumin promoter

The ovine β-lactoglobulin promoter.

In a preferred embodiment, the agent that stimulates the expression of a gene is part of a vector. Thus, the invention contemplates the use of vectors derived from expression vectors in prokaryotes such as pUC18, pUC19, Bluescript and their derivatives, mp18, mp19, pBR322, pMB9, ColEl, pCRI, RP4, phages and vectors "shuttle" such as pSA3 and pAT28, expression vectors in yeasts such as 2-micron plasmid type vectors, integration plasmids, YEP vectors, centromeric plasmids and the like, insect cell expression vectors such as pAC and pVL series vectors, plant expression vectors such as pIBI, pEarleyGate, pAVA, pCAMBIA, pGSA, pGWB, pMDC, pMY, pORE series vectors and the like, expression vectors in higher eukaryotic cells either based on viral vectors and [sic: or] non-viral vectors such as pcDNA3, pHCMV/Zeo, pCR3.1, pEFL/His, pIND/GS, pRc/HCMV2, pSV40/Zeo2, pTRACER-HCMV pUB6/V5-His, pVAXI, pZeoSV2, pCI, pSVL and pKSV-10, pBPV-1, pML2d and pTDTI.

In a preferred embodiment, the agent that stimulates the expression of a gene is delivered in the form of a viral vector. Suitable viral vectors for use in the present invention include, but are not limited to, adenoviral vectors, lentiviral vectors, retroviral vectors, vaccinia virus-derived vectors, adeno-associated virus (AAV) and herpes virus.

The present invention includes several non-viral methods for the transfer of expression constructs into cultured mammalian cells. These include calcium phosphate precipitation, DEAE-dextran, electroporation, direct microinjection, DNA-loaded liposomes and lipofectamine-DNA complexes, cell sonication, gene bombardment using micropoyectiles speed and receptor-mediated transfection. Some of these techniques can be adapted to use correctly in vivo or ex vivo.

In a further embodiment of this invention, the agent that stimulates the expression of a gene can be entrapped in the liposome. Liposomes are vesicular structures characterized by a phospholipid bilayer membrane and an inner aqueous medium.

The present invention contemplates the administration of agents that promote expression of a gene or the activity of the expression product of said gene locally, regionally, or systemically. The administration of the agents can be done in a localized manner in which case the agents are administered directly into the tumor, tumor vasculature, tumor-associated lymph vessel or duct associated with the tumor. The administration may be intraperitoneal, intrapleural, intravesicular, or intrathecal. Gene therapy can include regional administration in the vasculature of a tumor-associated member.

In the case of a polypeptide being used as an agent that stimulates the product activity expression of a gene, the invention contemplates the use of variants of the polypeptide modified with a peptide capable of promoting the translocation of the protein to the cell interior, such as the Tat peptide derived from the HIV-1 TAT protein, the third helix of the homeodomain of the Antennapedia protein *D. melanogaster*, the VP22 protein of the herpes simplex virus and arginine oligomers (Lindgren, A. et al., 2000, *Trends Pharmacol*. Sci, 21:99-103, Schwarze, S. R. et al., 2000, *Trends Pharmacol. Sci.,* 21:45-48, Lundberg, M et al., 2003, *Mol. Therapy* 8:143-150 and Snyder, E. L. and Dowdy, S. F., 2004, *Pharm. Res.* 21:389-393).

In a more preferred embodiment, the gene whose expression is decreased in response to an increase in the expression levels of c-MAF in a tumor, especially breast, colon, lung, kidney or thyroid, breast in particular, or whose expression is increased in response to a decrease in the expression levels of c-MAF in a tumor, especially breast, colon, lung, kidney or thyroid, breast in particular, is selected from the genes described in Table 2.

In an even more preferred embodiment, the gene whose expression is decreased in response to an increase in the expression levels of c-MAF in a tumor, especially breast, colon, lung, kidney or thyroid, breast in particular, is the RERG gene.

In a particular embodiment of the second use of the invention, the RERG activating agent is selected from the group comprised of
  (i) a nucleic acid encoding RERG or a functionally equivalent variant of RERG and
  ii) the RERG protein or a functionally equivalent variant RERG.

In a preferred embodiment, the nucleic acid encoding RERG corresponds to either of two transcriptional variants, collected in the NCBI database (in the Nov. 28, 2011 version) with accession numbers NM_032918.2 (variant 1) and NM_001190726.1 (variant 2).

The term "functionally equivalent variant of the RERG protein" is understood to mean polypeptides whose sequence derives from the RERG protein by substitution, insertion or deletion of one or more amino acids and which retain substantially the same function as the RERG protein, meaning, it acts as an inhibitor of cell proliferation and tumor formation. RERG protein variants can be identified using methods based the RERG's ability to inhibit cell proliferation such as the methods described in Example 4 of the present invention.

According to the invention, the variants preferably have a sequence identity with the nucleotide sequence of any RERG gene variant or with the amino acid sequence of any RERG protein isoforms of at least 50%, at least 60%, at least 70%, at least 80%, at least 90%, at least 91%, at least 92%, at least 93%, at least 94% to least 95%, at least 96%, at least 97%, at least 98% or at least 99%. The degree of identity between the variants and the specific sequences of the gene or RERG protein as defined above is determined using computer algorithms and methods that are well known to those skilled in the art. The identity between two nucleic acid sequences is preferably determined using the BLASTN algorithm, and the identity between two amino acid sequences is preferably determined using the BLASTP [BLAST Manual, Altschul, S., et al algorithm, NCBI NLM NIH Bethesda, Md. 20894, Altschul, S., y col., J. Mol. Biol. 215: 403-410 (1990)].

In a preferred embodiment, the cancer is breast, colon, lung, kidney, or thyroid cancer, more particularly breast cancer. In a preferred embodiment, the breast cancer is selected from the group consisting of ER+ cancer and ER-Her2- cancer. In a preferred embodiment, the bone metastasis is bone metastasis. In an even more preferred embodiment, the bone metastasis is osteolytic metastasis.

Pharmaceutical Compositions and Methods of Administration

Agents that inhibit the expression of a gene whose expression is increased in response to an increase in the expression levels of c-MAF in a tumor, especially breast, colon, lung, kidney or thyroid, more particularly breast, or whose expression is decreased in response to a decrease in the expression levels of c-MAF in a tumor, especially breast, colon, lung, kidney or thyroid cancer, more particularly breast, the agents that inhibit the activity of the expression product of a gene whose expression is increased in response to an increase in the expression levels of c-MAF in a tumor, breast in particular, colon, lung, kidney or thyroid, more particularly breast, or whose expression is decreased in response to a decrease in the expression levels of c-MAF in a tumor, especially breast, colon, lung, kidney or thyroid, more particularly breast, the agents that stimulate the expression of a gene whose expression is decreased in response to an increase in the expression levels of c-MAF in a tumor, especially breast, colon, lung, kidney or thyroid, more in particular breast, or whose expression is increased in response to a decrease in the expression levels of c-MAF in a tumor, especially breast, colon, lung, kidney or thyroid, more particularly of breast, and/or agents that stimulate the activity of the expression product of a gene whose expression is decreased in response to an increase in the expression levels of c-MAF in a tumor, especially breast, colon, lung, kidney or thyroid, more particularly breast, or whose expression is increased in response to a decrease in the expression levels of c-MAF are typically administered in combination with a pharmaceutically acceptable carrier.

The term "carrier" refers to a diluent or excipient with which the active ingredient is administered. Such pharmaceutical carriers can be sterile liquids, such as water and oils, including those of petroleum, animal, vegetable or synthetic origin, such as peanut oil, soybean oil, mineral oil, sesame oil and similar. These are preferably employed as water carriers or saline aqueous solutions and aqueous dextrose and glycerol solutions, particularly for injectable solutions. Suitable pharmaceutical carriers are described in "Remington's Pharmaceutical Sciences" by E W Martin, 1995. Preferably, the invention carriers are approved by the regulatory agency of a state of federal government or are listed in the U.S. Pharmacopeia or other generally recognized pharmacopeia for use in animals, and more particularly in humans.

The vehicles and auxiliary substances necessary to manufacture the desired pharmaceutical form of administration of the pharmaceutical composition of the invention will depend, among other factors, on the selected pharmaceutical form of administration. Said pharmaceutical forms of administration of the pharmaceutical composition will be manufactured according to conventional methods known to the skilled artisan. A review of different methods of administration of active principles, excipients to be used and procedures to produce them can be found in "Tratado de Farmacia Galenica", C. Fauli i Trillo, Luzán 5, S. A. de Ediciones, 1993. Examples of pharmaceutical compositions include any solid composition (tablets, pills, capsules, granules, etc.) or liquid (solutions, suspensions or emulsions) for oral, topical or parental administration. Furthermore, the pharmaceutical composition may contain stabilizers, suspensions, preservatives, surfactants and the like as necessary.

For use in medicine, inhibitor/activator agents of the present invention may be in the form of prodrug, salt, solvate or clathrate, either alone or in combination with additional active agents and can be formulated together with an excipient that is acceptable from a pharmaceutical standpoint. Preferred excipients for use in the present invention include sugars, starches, celluloses, gums and proteins. In a particular embodiment, the pharmaceutical composition of the invention shall be formulated into a pharmaceutical solid dosage form (e.g. tablets, capsules, dragées, granules, suppositories, sterile crystalline or amorphous solids which can be reconstituted to provide liquid forms, etc.), liquid (e.g. solutions, suspensions, emulsions, elixirs, lotions, ointments etc.) or semisolid (gels, salves, creams and the like). The pharmaceutical compositions of the invention may be administered by any route, including, but not limited to, oral, intravenous, intramuscular, intraarterial, intramedullary, intrathecal, intraventricular, transdermal, subcutaneous, intraperitoneal, intranasal, enteral, topical, sublingual or rectal. A review of the different forms of administration of active principles, excipients to be used and their manufacturing processes can be found in the Tratado de Farmacia Galénica, C. Fauli i Trillo, Luzán 5, S. A. de Ediciones 1993 in Remington's Pharmaceutical Sciences (AR Gennaro, Ed), 20th edition, Williams & Wilkins PA, USA (2000). Examples of pharmaceutically acceptable carriers are known in the prior art and include phosphate buffered saline solutions, water, emulsions such as oil/water emulsions, various types of wetting agents, sterile solutions etc. Compositions comprising such carriers can be formulated by conventional methods known in the prior art.

In the case that nucleic acids are administered (siRNA, polynucleotides encoding siRNA or shRNA or polynucleotides encoding dominant-negatives) the invention contemplates pharmaceutical compositions especially prepared for the administration of said nucleic acids. The pharmaceutical compositions can comprise said nucleic acids in naked form, i.e., in the absence of compounds protecting the nucleic acids from degradation by the nucleases of the organism, which entails the advantage that the toxicity associated to the reagents used for transfection is eliminated. Suitable routes of administration for the naked compounds include intravascular, intratumoral, intracranial, intraperitoneal, intrasplenic, intramuscular, subretinal, subcutaneous, mucosal, topical and oral route (Templeton, 2002, DNA Cell Biol, 21:857-867). Alternatively, the nucleic acids can be administered forming part of liposomes, conjugated to cholesterol or conjugated to compounds capable of promoting the translocation through cell membranes such as the Tat peptide Tat derived from the HIV-1 TAT protein, the third helix of the homeodomain of Antennapedia protein D. melanogaster, the herpes simplex virus VP22 protein, arginine oligomers and peptides such as those described in WO07069090 (Lindgren, A. et al., 2000, Trends Pharmacol. Sci, 21:99-103, Schwarze, S. R. et al., 2000, Trends Pharmacol. Sci., 21:45-48, Lundberg, M et al., 2003, Mol Therapy 8:143-150 and Snyder, E. L. and Dowdy, S. F., 2004, Pharm. Res. 21:389-393). Alternatively, the polynucleotide can be administered forming part of a plasmid vector or a viral vector, preferably vectors based on adenoviruses, in adeno-associated viruses or in retroviruses, such as viruses based on the murine leukemia virus (MLV) or lentivirus (HIV, FIV, EIAV).

The inhibitors/activators or the pharmaceutical compounds containing these can be administered in doses less than 10 mg per kilogram of body weight, preferably less than 5, 2, 1, 0.5, 0.1, 0.05, 0.01, 0.005, 0.001, 0.0005, 0.0001, 0.00005 or 0.00001 mg per kg of body weight. The unit dose can be administered by means of an injection, inhalation or through topical administration.

The dose depends on the severity and response of the condition to be treated and can vary between several days or several months until it is observed that the condition goes into remission. The optimal dosage can be determined by performing periodic measurements of the concentrations of the agent in the patient's system. The optimal dose can be determined using the values of the EC50 obtained by means of preliminary trials in vitro or in vivo in animal models. The unit dose can be administered once per day or at least once per day, preferably, at least once per day for 2, 4, 8 or 30 days. Alternatively, it is possible to administer an initial dose followed by one or several maintenance doses, generally of a lesser quantity than the initial dose. The maintenance regime can involve treating the patient with a dose ranging from 0.01 µg and 1.4 mg/kg of body weight per day, for example 10, 1, 0.1, 0.01, 0.001, or 0.00001 mg per kg of body weight per day. The maintenance dose is administered, preferably, at a maximum, once every 5, 10 or 30 days. The treatment should be continued for a period varying according to the type of affliction suffered by the patient, the severity thereof, and the status/condition of the patient.

Following treatment, the patient's evolution should be monitored in order to determine whether the dose should be increased, in the event that the disease does not respond to the treatment being administered, or whether the dose should be decreased in the event of an observed improvement in the illness, or in the event that unwanted side effects are observed.

Method for the Identification of Marker (Blueprint) Genes Indicating a Propensity for Metastases.

The authors of the present invention have developed a method by means of which it is possible to identify genes related to the propensity/susceptibility of a patient suffering from breast cancer to develop a metastasis. This methodology is based on the identification of genes whose expression in breast tumors is correlated with the expression of c-MAF and whose expression in a breast cancer cell line is observed as changing in response to a change in the levels of the expression of c-MAF.

In such a way, in another aspect, the invention is related to an in vitro method (herein below, gene identification method of the invention) for the identification of a genetic marker of the propensity for metastases in a patient suffering from cancer, in particular, breast, colon, lung, kidney or thyroid cancer, but particularly breast cancer, which involves
(i) determining the levels of expression of a candidate gene and a c-MAF gene in a primary breast cancer tumor sample, and
(ii) determining the change in the levels of expression of said candidate gene in a population of breast cancer cells in response to a modulation in the c-MAF gene expression in which the levels of expression of said gene demonstrate a significant statistical correlation with the expression of the c-MAF in the primary cancer tumor sample, in particular, breast, colon, lung, kidney or thyroid cancer, and more particularly, in breast cancer, and the change in the levels of expression as a result of the modification of the expression of the c-MAF gene demonstrates a statistical correlation with the change in the levels of said gene, which is indicative that said gene is a marker of the propensity/tendency for metastases in a patient.

In a first phase, the method for the identification of genes in the invention involves determining the levels of expression of a candidate gene and a c-MAF gene is a primary cancer tumor sample, in particular, breast, colon, lung, kidney or thyroid cancer, and more particularly, breast cancer.

The determination of the levels of the expression of said candidate gene and c-MAF gene in the primary tissue sample can be performed essentially as described in the context of the in vitro method, in order to predict the occurrence of metastases in a patient with cancer, in particular, breast cancer. In a preferred method, the levels of expression of said candidate gene and c-MAF gene can be performed using the RNA resulting from the transcription of said gene (RNA messenger or mRNA), based on the complementary DNA (cDNA) of said gene or through the quantification of the levels of expression of the protein coded by said gene.

In a second stage, the method for the identification of genes of the invention involves determining the change in the levels of the expression of said candidate gene in a population of cancer cells, in particular, breast, colon, lung, kidney or thyroid cancer, and more in particular, breast cancer, in response to a modulation of the expression of the c-MAF gene.

The determination of the change in the levels of the expression of the candidate gene requires that the levels of the expression in tumor cells be determined at two specific moments in time between which a change to the levels of the expression of c-MAF has been introduced. Said change to the levels of expression of c-MAF between said first point in time and said second point in time could represent an increase in the expression of c-MA or a decrease in the level of expression of c-MAF.

In a preferred method, the modulation of the levels of c-MAF that is performed during stage (ii) represents an increase in the levels of c-MAF. In order to achieve this, this stage requires that a polynucleotide cell that codes the c-MAF or some part of c-MAF be introduced into the cell. Appropriate methods for the introduction of a gene of interest into a cell and appropriate arrangements for the expression of a gene of interest in a cell have been described in the context of therapeutic methods based on the activation of genes whose expression demonstrates an inverse correlation to the expression of c-MAF and which are used in the same form in the present method.

With the aim of inducing an increase to the levels of expression of c-MAF in a target/given cellular population, it is possible to modify the cell through the introduction into the same of a polynucleotide that codes the c-MAF, this being operationally linked to a promoter that facilitates cellular expression in tumors, such as breast, colon, lung, kidney or thyroid cancer, but preferably, breast cancer. Said polynucleotide is created normally by forming part of a vector that contains, in addition to said polynucleotide, additional sequences to guarantee its propagation in host prokaryote organisms (for example, an origin of application) as well as selection markers. By means of illustration, the following promoters can be used, which are appropriate for the expression of a gene of interest in breast cancer tumor cells:

The promoter of stromelysin 3 (Basset et al., Nature 348: 699,1990)

The promoter of the glycoprotien similar to mucin (DF3, MUCI) ((Abe et al., Proc. Natl. Acad. Sci. USA 90: 282,1993)

The promoters c-erbB-3, c-erbB-2 or c-erbB-4

The promoter of the mouse mammary tumor virus (MMTV)

The promoter of whey acidic protein

The promoter of human alpha-lactalbumin

The promoter of bovine β-lactoglobulin

The polynucleotide that encodes c-MAF or the vector that contains said polynucleotide is introduced into the cells that are the object of the study using any of the methods of transfection known by a person skilled in the science (see sections 9.1 to 9.5 in Ausubel, F. M. et al., Current Protocols in Molecular Biology, John Wiley & Sons Inc, 2003). In particular, the cells can be transfected using DNA co-precipitation with calcium phosphate, DEAE-dextran, polibreon, electroporation, microinjection, fusion mediated by liposomes, lipofection, infection by retrovirus and biolistic transfection.

Alternatively, the cell can be modified through the introduction of the c-MAF protein into the same. For this, the invention provides for the use of variants of c-MAF modified by a peptide that is capable of promoting the translocation of the protein to the inside of the cell (sub-cellular level), such as the peptide, Tat, derived from the HIV-1 Tat protein, the third helix of the homeodomain of the Antennapedia protein of *Drosophila melanogaster*, the VP22 protein of the herpes simplex virus and oligomers of arginine (Lindgren, A. et al., 2000, *Trends Pharmacol*. Sci, 21:99-103, Schwarze, S. R. et al., 2000, *Trends Pharmacol. Sci.*, 21:45-48, Lundberg, M et al., 2003, *Mol. Therapy* 8:143-150 y Snyder, E. L. and Dowdy, S. F., 2004, Pharm. Res. 21:389-393).

In a more specific model, the increase to the expression in the c-MAF takes place during the expression of the cancer cells, in particular, breast cancer, as well as colon, lung, kidney or thyroid cancer, and more in particular, breast cancer, the short isoform of the c-MAF. In another, even more particular model, the increase to the expression of the c-MAF takes place during the expression in the cancer cells, in particular, breast cancer, as well as colon, lung, kidney or thyroid cancer, and more in particular, breast cancer, the long isoform of the c-MAF. In an even more particular model, the increase to the expression of the c-MAF takes place during the co-expression in the cancer cells, in particular, breast cancer, as well as colon, lung, kidney or thyroid cancer, and more in particular, breast cancer, of the long and short isoform of the c-MAF.

In the event that the modulation of the levels of c-MAF that takes place during the second step involves a reduction to the levels of c-MAF, this step requires the introduction of a cell of an agent that is capable of silencing c-MAF. By means of illustration and which is by no means exhaustive, examples of appropriate agents to achieve a reduction in the levels of c-MAF include antisense oligonucleotides specific to said gene, RNA interference (RNAi) processes specific to said gene, catalytic RNAs or specific ribonucleic acid enzymes for said gene, c-MAF inhibiting agents and inhibitor antibodies.

RNA interference (RNAi) processes for c-MAF include the RNAi described in WO2005046731, of which one chain is ACGGCUCGAGCAGCGACAA (SEQ ID NO: 1). Other sequences of the RNAi specific for c-MAF include, but are not limited to, CUUACCAGUGUGUUCACAA (SEQ ID NO: 2), UGGAAGACUACUACUGGAUG (SEQ ID NO: 3), AUUUGCAGUCAUGGAGAACC (SEQ ID NO: 4), CAAGGAGAAAUACGAGAAGU (SEQ ID NO: 5), ACAAGGAGAAAUACGAGAAG (SEQ ID NO: 6) y ACCUGGAAGACUACUACUGG (SEQ ID NO: 7).

Dominant negatives of c-MAF that can be used in the context of the present invention include mutants that are capable of being dimerised with the c-MAF but that are lacking the capacity to activate the transcription given that they are incapable of homodimerisation as well as heterodimerisation with other members of the AP-1 family, such as Fos y Jun. As such, negative dominants of c-MAF can be any of the small maf proteins that exist in the cell and that are lacking the two thirds of the amino-terminal ends containing the domain of the trans-activation (for example, mafK, mafF, mafg and pi 8) (Fujiwara et al (1993) Oncogene 8, 2371-2380; Igarashi et al. (1995) J. Biol.Chem. 270, 7615-7624; Andrews et al. (1993) Proc. Natl. Acad. Sci. USA 90, 11488-11492; Kataoka et al. (1995) Mol. Cell. Biol. 15, 2180-2190) (Kataoka et al. (1996) Oncogene 12, 53-62).

Alternatively, dominant negatives proteins for c-MAF include variants of c-MAF that maintain the capacity for dimerisation with other proteins but that is lacking the capacity to activate the transcription. These variants are, for example, those that are lacking the domain for the transactivation of c-MAF, located in the end N-terminal of the protein. As such, c-MAF dominant negative variants include, by way of example, the variants in which at least the amino acids 1 to 122 have been eliminated, at least the amino acids 1-187 or at least the amino acids 1 to 257 (considering the numbering of the human c-MAF as described in U.S. Pat. No. 6,274,338).

In a particular model of the method of the invention, the tumor sample that is used in step (i) is taken from a breast cancer tumor, or that of the colon, lung, kidney, or thyroid, and more in particular, a breast cancer tumor. In a more particular model of the invention method, the tumor sample, in particular, that of a breast cancer tumor, used in step (i) is taken from an ER tumor and a triple negative tumor. In a preferred model, the cancer cells, in particular, those from a breast cancer tumor, used in step (ii) are ER+ o have been taken from a triple negative tumor. In an even more particular model, the metastasis is that of a bone metastasis.

Other c-MAF compound inhibitors appropriate for use in the present invention include:

TABLE 3

Small molecules with the capacity to inhibit c-MAF

I H endriandric acid derivatives such as those described in WO2008014888 and which correspond to the general formula

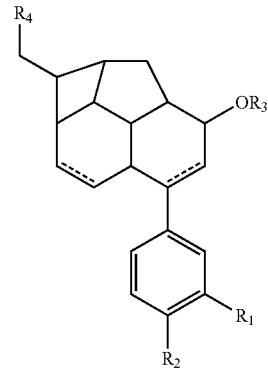

where
$R_1$ and $R_2$ are, independent, one of the other,
1.0 H 0
2.0 one group —O-alkyl $C_1$-$C_6$, —O-alkenyl $C_2$-$C_6$, —O-alkynil $C_2$-$C_6$ u —O-aril $C_6$-$C_{10}$, in which, alkenyl and alkynil appear as linear or branching, and in which of the groups alkyl, alkenyl y alkynil are mono- or di-substituted with:
2.1 —OH,
2.2 =O,
2.3 —O-alkyl $C_1$-$C_6$, in which the alkyl is either of a linear chain or branched
2.4 —O-alkenyl $C_2$-$C_6$, in which the alkyl is either of a linear chain or branched,
2.5 -aril $C_6$-$C_{10}$,
2.6 —NH -alkyl $C_1$-$C_6$, in which the alkyl is either of a linear chain or branched,
2.7 —NH-alquenilo $C_2$-$C_6$, in which the alkyl is either of a linear chain or branched,
2.8 —NH2 or
2.9 halogen,
and in which the aril group, is potentially either mono- or di-substituted with the substitute, 2.1 or 2.3 to 2.9,
in which the substitutes 2.3, 2.4, 2.6 and 2.7 can be additionally substituted with the functions, —CN, -amide u -oxime, and 2.5 can be additionally substituted with the functions —CN or amide, or $R_1$ and $R_2$ together form a ring, in which $R_1$ and $R_2$ signify one group, —O-[alkynl ($C_1$-$C_6$)]-O—,
$R_3$ is
1.0 H or
2.0 one group —O-alkyl group $C_1$-$C_6$, —O-alkenyl $C_2$-$C_6$, —O-alkynil $C_2$-$C_6$ u —O-aril $C_6$-$C_{10}$, in which, alkenyl and alkynil appear as linear or branching, and in which of the groups alkyl, alkenyl y alkynil are mono- or di-substituted with:

TABLE 3-continued

Small molecules with the capacity to inhibit c-MAF 2.1 —OH,
2.2 =O,
2.3 —O-alkyl $C_1$-$C_6$, in which the alkyl is either of a linear chain or branched,
2.4 —O-alkenyl $C_2$-$C_6$, in which the alkyl is either of a linear chain or branched,
2.5 -aril $C_6$-$C_{10}$,
2.6 —NH -alkyl $C_1$-$C_6$, in which the alkyl is either of a linear chain or branched,
2.7 —NH— alkenyl $C_2$-$C_6$, in which the alkyl is either of a linear chain or branched,
2.8 —NH2 or
2.9 halogen,
and in which the aril group, is potentially either mono- or di-substituted with the substitute, 2.1 or 2.3 to 2.9,
in which the substitutes 2.3, 2.4, 2.6 and 2.7 can be additionally substituted with the functions, —CN, -amide u -oxime, and 2.5 can be additionally substituted with the functions —CN or amide
$R_4$ is $CO_2R_3$, $CO_2NHR_3$, CHO, $CH_2OR_3$, $CH_2OSi(R_3)_3$, $CH_2Br$, $CH_2CN$, in which $R_3$ is as has been defined above
And, in particular, the compounds II Derived from 8-hydroxyquinolines as described in WO2009146546, of which the general formula

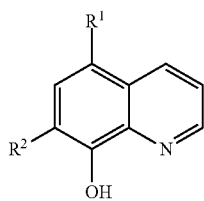

where
R1 is selected from the group of NO2, NH2, NH(C1-6alkyl) and N(C1-6alkyl)(C1-6alkyl);
R2 is selected from H, halogen, C1-6alkyl, and C1-6alkyl substituted with fluorine,
or
R1 is Cl and R2 is Br o H
and, preferably, the compounds

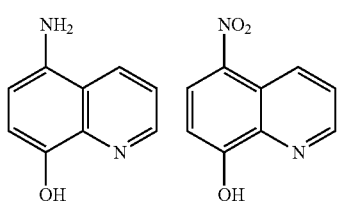

III Clioquinol (5-chloro-7-iodo-crinoline-8-lo) as described in WO09049410

IV Compounds as described in WO08098351, of which the general formula

In which
==-:-:-: is a single or double bond,
R1 is selected from the H group, C1-4alkyl, C(O)OC1-4alkyl, C(O)C1-4alkyl and C(O)NHC1-4alkyl;
R2 is selected from H and C1-4alkyl;
R3 is selected from H and C1-4alkyl;
or R2 and R3 are found bound together along with the carbon atom and nitrogen to which they are bound and together form a peperidine ring, R4 and R5 are selected independently from H, halogen, hidroxyl, C1-4alkyl, C1-4alkyl substituted by fluorine and C1-4 balcony; and X is selected from C and N.
and preferred compounds such as
Cyproheptadine (4-(5H-dibenzo[a,d]cyclopentane-S-ylidene)-1-methylpiperidine)
Amitriptyline (3-(10,11-dyhidro-5H-dibenzo[[a,d]]cycloheptene-5-ylidene)-N,N-dimethyl-1-propanamine)
Loratadine (ethyl-4-(8-chloro-S,6-dyhydro-11H-benzo[5,6]cyclohepta[1,2-b]piridine-11-ylidene)-1-)piperidine carboxylate
Ciclobenzapine (3-(5H-dibenzo[a,d]cycloheptane-5-ylidene)-N,N-dymethyl-1-propanamine)

V Nivalenole (12,13-Epoxy-3,4,7,15-tetra-hydroxytricho-tec-9-en-8-ona) as described in WO0359249

Other inhibitors of c-MAF are described in patent application WO2005063252, as shown in the following table (Table 4).

TABLE 4 c-MAF inhibitors

| Antagonist | Reference for cdk2 inhibitory activity |
|---|---|
| Purine Analogs | |
| Purvalanols such as 2-(1R-Isopropyl-2-hydroxyethylamino)-6-(3-chloroaniline)-9-isopropylpurine having a molecular formula $C_{19}H_{25}ClN_6O$ available from Sigma-Aldrich under the trade name Purvalanol A (#P4484, Sigma-Aldrich, St. Louis, MO), Purvalanol B, aminopurvalanol, compound 52 (where isopropyl of purvalanol A is replaced with H) | Gray, N. S. et al., Science, 281, 533-538 (1998); Chang, Y. T. et al., Chem. Biol., 6, 361-375 (1999). |
| 2-(Hydroxyethylamino)-6-benzylamino-9-methylpurine having a molecular formula $C_{15}H_{18}N_6O$ available from Sigma-Aldrich under the trade name Olomoucine (#O0886), 2-(2'-Hydroxyethylamino)-6-benzylamino-9-isopropylpurine having a molecular formula $C_{17}H_{22}N_6O$ available from Sigma-Aldrich under the trade name $N^9$-isopropylolomoucine (#I0763); CVT-313 | Vesely, J., et al., (1994) Eur. J. Biochem., 224, 771-86, 11; Brooks, E. E., et al., (1997) J. Biol. Chem., 272, 29207-11 |
| 6-(Benzylamino)-2(R)-[[1-(hydroxymethyl)propyl]amino]-9-sopropylpurine 2-(R)-[[9-(1-methylethyl)-6-[(phenylmethyl)amino]-9H-purin-2-yl]amino]-1-butanol having a molecular formula of $C_{19}H_{26}N_6O$ available from Sigma-Aldrich under the trade name Roscovitine (#R7772), methoxyroscovitine | Wang, D. et al., J. Virol., 75, 7266-7279 (2001); McClue, S. J. et al., Int. J. Cancer, 102, 463-468 (2002); Meijer, L., et al., (1997) Eur. J. Biochem., 243, 527-36 |
| Purine analog N2-(cis-2-Aminocyclohexyl)-N6-(3-chlorophenyl)-9-ethyl-9H-purine-2,6-diamine having a molecular formula of $C_{19}H_{24}ClN_7$ available from Sigma-Aldrich under the trade name CGP74514 (#C3353) | Imbach, P. et al., Bioorg. Med. Chem. Lett., 9, 91-96 (1999); Dreyer, M. K. et al., J. Med. Chem., 44, 524-530 (2001). |
| CGP79807, a purine analog of CGP74514 (supra) where Cl is replaced with CN, OH is removed, and the ortho position of cyclohexane ring is $NH_2$ | Imbach, P. et al., Bioorg. Med. Chem. Lett., 9, 91-96 (1999); Dreyer, M. K. et al., J. Med. Chem., 44, 524-530 (2001). |
| Purine analog such as O6-cyclohexylmethyl guanine NU2058 | Arris, C. E. et al., J. Med. Chem., 43, 2797-2804 (2000); Davies et al, Nature Structural Biology, 9: 10, 745-749, 2002 |
| Purine analog such as NU6102 | Arris, C. E. et al., J. Med. Chem., 43, 2797-2804 (2000); Davies, T. G. et al., Nat. Struct. Biol., 9, 745-749 (2002). |
| Isopentenyl-adenine | Vesely, J., et al., (1994) Eur. J. Biochem., 224, 771-86 |
| Nonpurine based agents | |
| Indirubins such as indirubin-3'-monoxime having a molecular formula of $C_{16}H_{11}N_3O_2$ available from Sigma-Aldrich under the trade name (#I0404), indirubin 5-sulfonate, 5-chloro indirubin | Davies, T. G. et at., Structure, 9, 389-397 (2001); Marko, D. et al., Br. J. Cancer, 84, 283-289 (2001); Hoessel, R., et al., (1999) Nat. Cell Biol., 1, 60-7; PCT/US02/30059 to Hellberg et al., published as WO 03/027275. |
| Oxindole 1 of Fischer as referenced in column 2 of this table, (#IN118, JMAR Chemical, Indenopyrazoles | Porcs-Makkay, M., et al., Tetrahedron 2000, 56, 5893; Org. Process Res. Dev. 2000, 4, 10 Nugiel, D. A. et al., J. Med. Chem., 44, 1334-1336 (2001); Nugiel, D. A. et al., J. Med. Chem., 45, 5224-5232 (2002); Yue, E. W. et al., J. Med. Chem., 45, 5233-5248 (2002). |
| Pyrido(2,3-d)pyrimidine-7-ones, compound 3 of Fischer | Barvian, M. et al., J. Med. Chem., 43, 4606-4616 (2000); Toogood, P. L., Med. Res. Rev., 21, 487-498 (2001). |
| Quinazolines such as anilinoquinazoline | Sielecki, T. M. et al., Bioorg. Med. Chem. Lett., 11, 1157-1160 (2001); Mettey et al., J. Med. Chem. 2003, 46, 222-236. |
| Thiazoles such as fused thiazole, 4-{[(7-Oxo-6,7-dihydro-8H-[1,3]thiazolo[5,4-e]indol-8-ylidene)methyl]amino}-N-(2-pyridyl)benzenesulfonamide having a molecular formula of $C_{21}H_{15}N_5O_3S_2$ available from Sigma-Aldrich under the trade name GW8510 (#G7791) | Davis, S. T. et al., Science, 291, 134-137 (2001); PCT/US02/30059 to Hellberg et al., published as WO 03/027275. |
| Flavopiridols such as flavopiridol (L86 8275; NCS 649890, National Cancer Institute, Bethesda, MD) and a dechloro derivative | Carlson, B. A., et al., (1996) Cancer Res., 56, 2973-8 |
| Alkaloids such as Staurosporine (#S1016, A. G. Scientific, San Diego, CA) or UCN-01 (7-hydroxystaurosporine) National Cancer Institute, Bethesda, MD | Rialet, V., et al., (1991) Anticancer Res., 11, 1581-90; Wang, Q., et al., (1995) Cell Growth Differ., 6, 927-36, Akiyama, T., et al., (1997) Cancer Res., 57, 1495-501, Kawakami, K., et al., (1996) Biochem. Biophys. Res. Commun., 219, 778-83 |

TABLE 4-continued c-MAF inhibitors

| Antagonist | Reference for cdk2 inhibitory activity |
|---|---|
| Paullones such as 9-Bromo-7,12-dihydro-indolo[3,2-d][1]benzazepin-6(5H)-one having a molecular formula of $C_{16}H_{11}BrN_2O$ available from Sigma-Aldrich under the trade name kenpaullone (#K3888), or 9-Nitro-7,12-dihydroindolo-[3,2-d][1]benzazepin-6(5)-one having a molecular formula of $C_{16}H_{11}N_3O_3$ available from Sigma-Aldrich under the trade name alsterpaullone (#A4847) | Zaharevitz, D. W. et al., Cancer Res., 59, 2566-2569 (1999); Schultz, C. et al., J. Med. Chem., 42, 2909-2919 (1999); Zaharevitz, D. W., et al., (1999) Cancer Res., 59, 2566-9; PCT/US02/30059 to Hellberg et al., published as WO 03/027275. |
| CGP 41251, an alkaloid | Begemann, M., et al., (1998) Anticancer Res., 18, 2275-82; Fabbro et al., Pharmacol Ther. 1999 May-Jun; 82(2-3): 293-301 |
| Hymenialdisines such as 10z-hymenialdisine having a molecular formula of $C_{11}H_{10}BrN_5O_2$ available from Biochemicals.net, a division of A.G. Scientific, Inc. (San Diego, CA) (H-1150) | Meijer, L., et al., (1999) Chemistry & Biology, 7, 51-63; PCT/US02/30059 to Hellberg et al., published as WO 03/027275. |
| CGP60474, a phenylaminopyrimidine | 21; WO95/09853, Zimmermann et al., Sep. 21, 1994 |
| Thiazolopyrimidine 2 | Attaby et al., Z. Naturforsch. 54b, 788-798 (1999) |
| Diarylurea | Honma, T. et al., J. Med. Chem., 44, 4628-4640 (2001), Honma, T. et al., J. Med. Chem., 44, 4615-4627 (2001). |
| (2R)-2,5-Dihydro-4-hydroxy-2-[(4-hydroxy-3-(3-methyl-2-butenyl)phenyl)methyl]-3-(4-hydroxyphenyl)-5-oxo-2-furancarboxylic acid methyl ester having a molecular formula of $C_{24}H_{24}O_7$ available from Sigma-Aldrich under the trade name Butyrolactone-I (B7930) | Kitagawa, M. et al., Oncogene, 8, 2425-2432 (1993). |
| Aloisine A, Cat. No. 128125 (Calbiochem, San Diego, CA) | Mettey et al., J. Med. Chem. 2003, 46, 222-236 |

In another model that is even more particular (specific), the decrease in the levels of expression of c-MAF are produced through the silencing of the breast cancer tumor cells, or cancer cells from the colon, lungs, kidneys or thyroid, but more in particular, breast cancer, of the short isoform of c-MAF. In another model, the decrease in the levels of c-MAF are produced through the silencing of the breast cancer tumor cells, or cancer cells from the colon, lungs, kidneys or thyroid, but more in particular, breast cancer, of the long isoform of c-MAF. In another model even more particular, the decrease in the levels of c-MAF are produced through the silencing of the breast cancer tumor cells, or cancer cells from the colon, lungs, kidneys or thyroid, but more in particular, breast cancer, of the long and short isoform of c-MAF. The population of the cancer cells, in particular breast cancer cells, or of the colon, lungs, kidneys or thyroid, more in particular, from breast cancer, can be obtained from biopsy samples taken from patients suffering from these types of cancer, or can be linear cells of these types of cancer, such as linear breast cancer cells that include, but are not limited to, cells from the lines MCF-7, T47D and MDA-MB-231, MDA-MB-435, MDA-MB-468, BT20, SkBr3, HCC-1937, BT-474 and ZR75.1. In a preferred model, step (ii) is performed using cells from the MCF7 breast cancer cell line. Colon cancer cell lines include, but are not limited to HCA-7, KM12C, KM12SM, KM12I 4a, SW480, SW620. Lung cancer cell lines include, but are not limited to, NCI-H1781, NCI-H1373, LC319, A549, PC14, SK-MES-1, NCI-H2170, NCI-H1703, NCI-H520, LU61, LX1, SBC-3, SBC-5, DMS273 and DMS114. Lung cancer cell lines include, but are not limited to 786-0, 769-P, A-498, SW-156, SW-839, A-704, ACHN, CaKi-1 and CaKi-2. Lung cancer cell lines include, but are not limited to, BCPAP, KTC-1, K1, TCP1, FTC133, ML1, 8505C, SW1736, Cal-62, T235, T238, Uhth-104, Uhth-104, HTh74, KAT18, TTA1, FRO81-2, HTh7, C643, BHT101 and KTC-2.

Once the following have been determined: (i) the levels of expression of a candidate gene and a c-MAF gene in a primary cancer tumor sample, such as from a breast cancer tumor, or from colon, lung, kidney or thyroid cancer tumor cells, more in particular, breast cancer, and (ii) the change in the levels of the expression of said candidate gene in a population of cancer cells, such as breast, lungs, kidney or thyroid, more in particular, breast cancer, in response to a modulation of the expression of the c-MAF gene, the in vitro method for the identification of marker genes for the identification of a propensity (tendency) towards metastasis includes (i) the comparison of the levels of expression of said gene and of the c-MAF gene in the primary cancer tumor sample and (ii) the comparison of the levels of expression in response to the modulation of the expression of the c-MAF gene with the changes to the levels of said gene (sic—no period here in the original)

In a performed model, if the expression of said gene defined/determined in step (i) is directly correlated to the levels of c-MAF in the primary tumor sample and if the change in the levels of expression in response to the modulation of the expression of the c-MAF gene is directly correlated to said modulation, this is indicative that elevated levels of said gene are indicative of a propensity to metastasis.

In another preferred model, if the expression of said gene determined in step (i) is inversely correlated with the levels of c-MAF in the primary tumor sample and if the change to the levels of expression in response to the modulation of the expression of the c-MAF gene is negatively correlated to said modulation, this is indicative that reduced levels of said gene are indicative of a propensity to metastasis.

The correlation between the expression of a candidate gene and the expression of c-MAF in the primary tumor sample is created through the comparison of the levels of the expression of both genes with respect to a reference value, in which it is considered that there is a correlation between the expression of both genes if both genes show, in the same sample, a variation of their expression vis-a-vis the reference value. The correlation can be direct (the increase in the expression of the candidate gene with respect to the reference value is correlated to an increase in the expression of c-MAF with respect to the reference value for said gene or the reduction in the expression of the candidate gene with respect to the reference value is related to a decrease in the expression of the c-MAF gene with respect to the reference value for said gene) or the inverse (the increase in the expression of the candidate gene with respect to the reference value is correlated to a decrease increase (sic—seems to be an error here) in the expression of c-MAF with respect to the reference value for said gene or the reduction in the expression of the candidate gene with respect to the reference value is related to an increase in the expression of the c-MAF gene with respect to the reference value for said gene)

The correlation between the change in the levels of the expression of the candidate gene in response to the modulation of the c-MAF gene is realized by determining the level of expression of said gene before inducing the modulation of the expression of the c-MAF gene and the level of expression of said gene in the same sample after the modulation in the expression of the c-MAF gene has been produced, considering that there is a correlation if a variation in the expression of the candidate gene in a concomitant manner to the change in the expression of c-MAF has been produced. The correlation may be direct (candidate gene expression increases concomitantly with increased c-MAF expression, or decreased gene expression decreases concomitantly with decreased c-MAF expression) or inverse (candidate gene expression increases concomitantly with decreased c-MAF expression, or candidate gene expression decreases, relative to the reference value, concomitantly with increased c-MAF expression, relative to the reference value for this gene).

It is considered that there exists an increase to the expression of the candidate gene in a concomitant manner with respect to the variation in the expression of c-MAF when there is produced an increase in the levels of the expression of said gene of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more with respect to the levels before the change to the expression of c-MAF is introduced.

It is considered that there exists a decrease to the expression of the candidate gene in a concomitant manner with respect to the variation in the expression of c-MAF when there is produced a decrease in the levels of the expression of said gene of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more with respect to the levels before the change to the expression of c-MAF is introduced.

In a preferred model, the metastasis is a bone metastasis.

The invention is described herein below by means of the following examples, which shall be considered solely for illustrative purposes, and do not limit the scope of the invention.

EXAMPLES

I. Materials and Methods

Experiments Study Models

New experimental models for the study of the metastasis of breast cancer ER+ and ER−PR−Her2− have been developed. To this end, the human cell line of breast cancer ER+, known as MCF7, the same which has been transfected in a stable form with a vector allowing for the expression of the GFP/Luciferasa has been used. This cell line was inoculated in immuno-deficient mice (Balb-c/nude) by injection via intraventricular or in the (tail) caudal vein in order to be able to select cells with metastatic capacity in various organs. The rats bore subcutaneous implants of estrogens in order to guarantee the presence of these hormones throughout the course of the experiment.

Selection of Metastatic Populations

The metastatic populations in different tissues were selected through the identification and isolation of the cells from the metastatic lesions. For this, bioluminescence imaging techniques were used, incorporating the technology with which it is possible to detect the establishment and growth of tumor cells in organs of interest at different times and to quantify the number of tumorous cells present. For the application of this technology, the cells have been transducted in order to express the gene of the luciferase and the GFP and with these their monitoring/observance in vivo in real time using non-invasive methods is possible. The capture of the luminescence image (luciferase activity(is done with the animal under general anesthesia, using equipment of the Xenogen IVIS type and the Livingimage software as the preferred methodology due to its level of sensibility and speed. In order to isolate the metastatic cells, the tumor lesion is dissected and, then, using cytometric techniques using sweeping with laser-induced fluorescence (GFP) (green fluorescent protein), the metastatic cells are isolated from the other cells of the host organism. Once these cells have been isolated, the process is repeated in order to enrich/feed its tropism through specific tissues. Using these procedures, specific metastatic populations having the specificity of a tissue were isolated, including metastasis in bones and the brain.

Once the metastatic populations were identified and isolated, a high-performance transcriptional analysis was performed. All in all, this strategy allowed for the identification of genes whose transcription is enhanced including some, acting as mediators of the metastatic process in cancerous cells with a poor prognosis. The implication of the genes whose expression is found altered in the colonization by means of metastatic cells in specific tissues and organs was confirmed through an unbiased in vivo selection procedure. The selected population of cells with a high capacity for colonizing bone was called BoM2.

Identification of the Group of Genes whose Expression is Correlated with the Expression of c-MAF.

Through a comparison of the genome-wide transcriptional profiles of 349 primary breast tumors, genes whose expression correlated well in a positive (direct) manner were identified, or, alternatively, in a negative (inverse) manner, with the expression of c-MAF were identified. The validation of the genes obtained in this manner was performed through the analysis of their expression in relation to the expression of c-MAF in defined cellular models. The MCF7 ER+ breast cancer cell lines were modified in order that that they expressed well the long isoform or the short isoform of the c-MAF gene and the profiles for the expression of RNAm were determined using Affymetrix U133A2Plus. Using routine technology, derivatives of the MCF-7 bone metastasis cells were obtained, in which c-MAF was depleted. The gene expression profiles were determine in the previous cellular populations and those genes that were significantly modified as a function of the expression of c-MAF were selected. These results made it possible to obtain the metastatic program of c-MAF in bone, which included 99 genes (76 of these were over-expressed, Table 1, and 33 repressed, Table 2), whose expression is significantly correlated with the level of expression of c-MAF in primary breast cancer tumors, and which vary as a function of c-MAF in at least one of the cellular conditions that are used. The metastatic program of c-MAF in bone includes cytokines, cell adhesion molecules, protease anchored to membrane, signaling mediators and transcription factors.

This group of genes, in which changes to the levels of expression in ER+ breast cancer cells were observed, was subject to validation. For this, the levels of expression of the candidate genes were compared with the profiles of gene expression obtained using primary breast cancer tumors and metastatic cohorts, which included 560 primary breast cancer tumors and 46 metastatic cells from patients suffering from breast cancer.

Bioinformatics and Computational Biology

In order to obtain the groups of genes rich in metastasis and to verify their clinical correlation, R statistical packages and Bioconductor were used. The specific functions and structures for the treatment of the data were imported and are open to public access on the website www.bioconductor.org.

Example 1

Selection of Relevant Genes

Figure 1B:
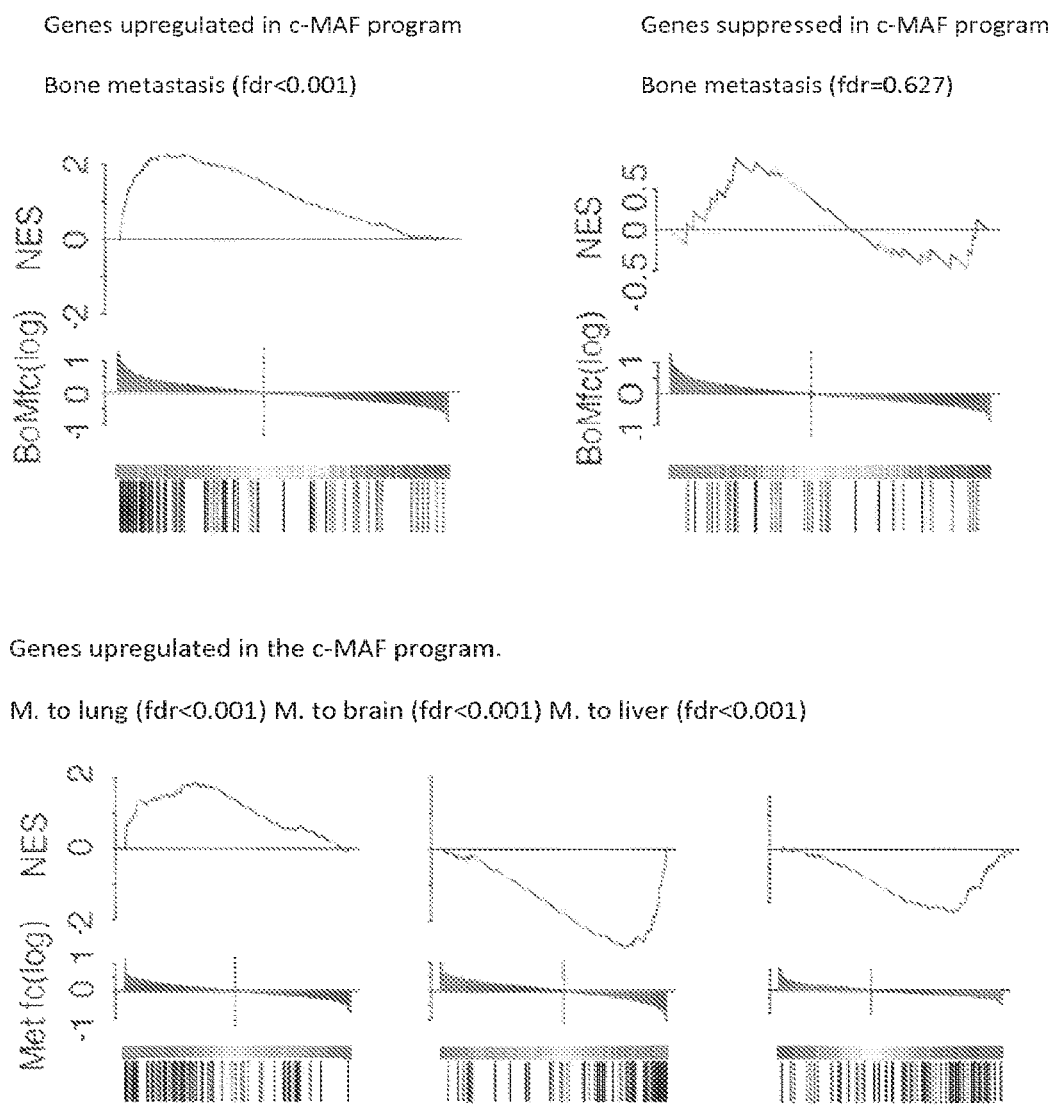
Figure 2A:
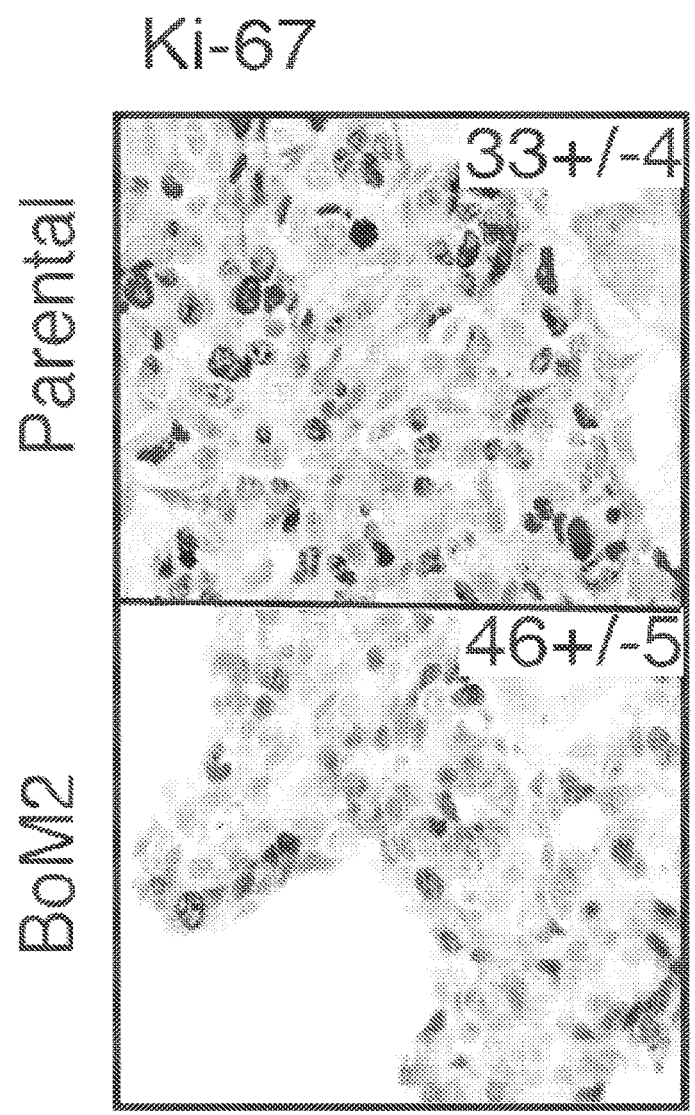
FIG. 2A-D. (2A) Analysis of Ki-67 expression levels, proliferation marker, in metastatic lesions in experimental mice models of the xenograft type using moderately metastatic (parental) ER+, MCF7 breast cancer cells and derivatives thereof which are highly metastatic to bone (BoM2). (2B) Validation using quantitative RT-PCR of the relationship between the MAF expression and the RERG gene. (2C) Bone metastasis in mice using BoM2 cells with or without MAF. The Ki-67 signal and caspasa-3 activity is quantified via inmunohistochemistry. (2D) Increased RERG is induced in cells which are highly metastatic to bone. Cell derivates with RERG expression are injected into the left ventricle of mice and the colonization of the bone is analyzed live and in real time using bioluminescent imaging techniques to validate the contribution of RERG in the presence of MAF in ER+ breast cancer metastasizing to the bone.
Figure 2B:
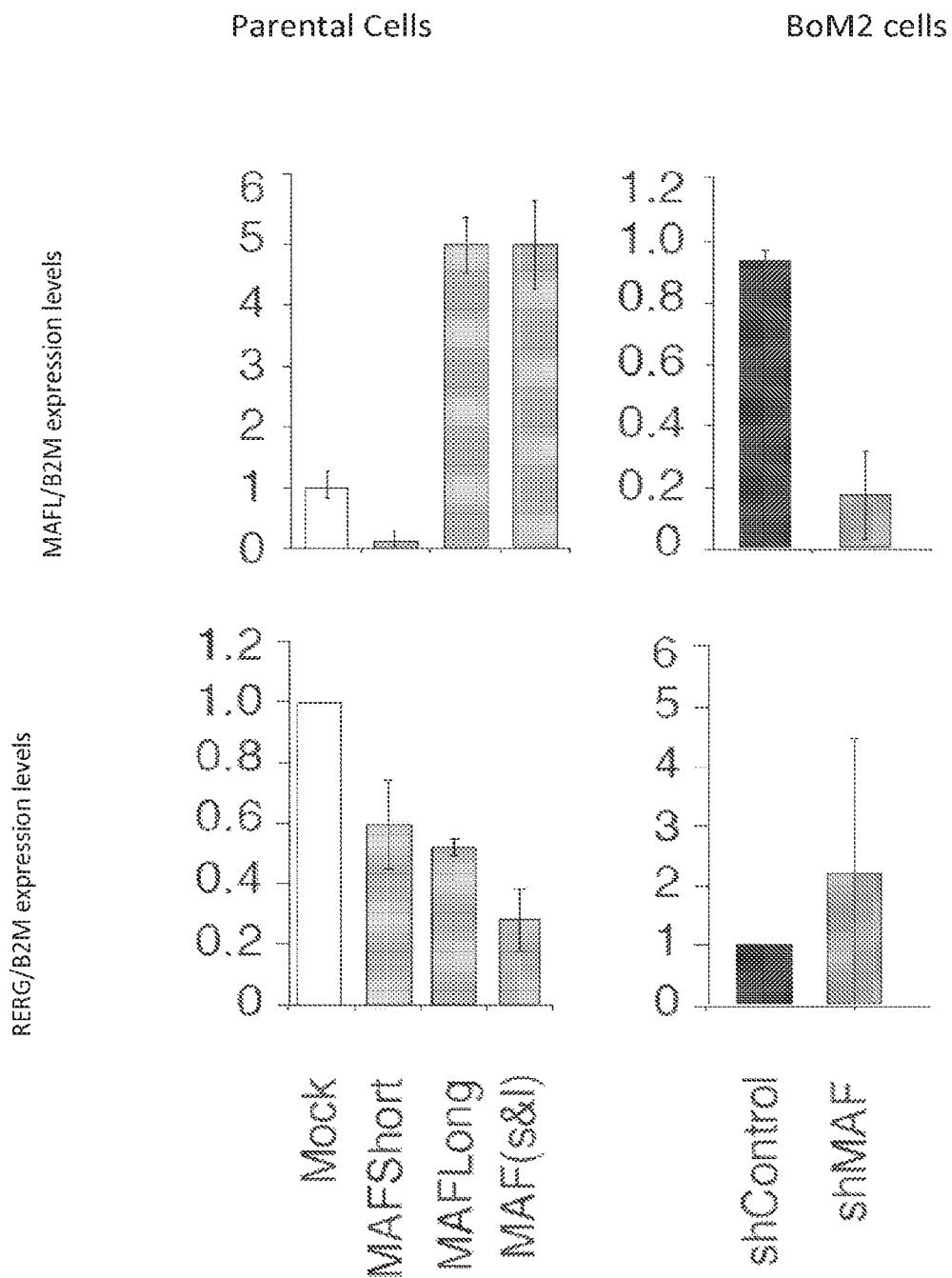
Figure 2C:
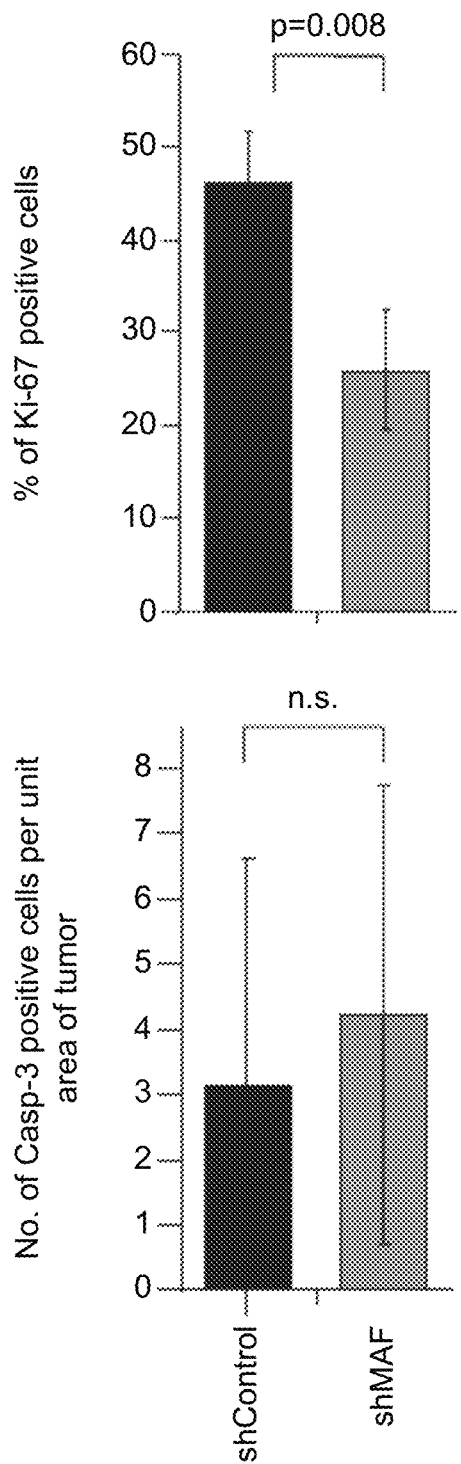
Figure 2D:
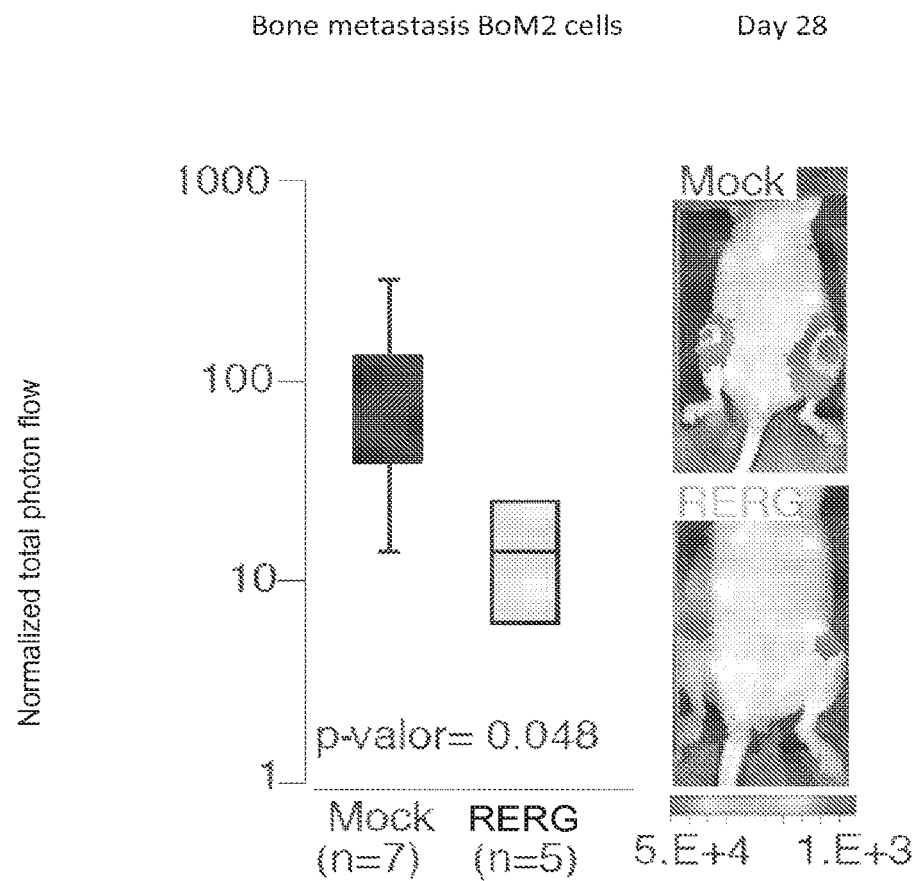
Figure 2D:
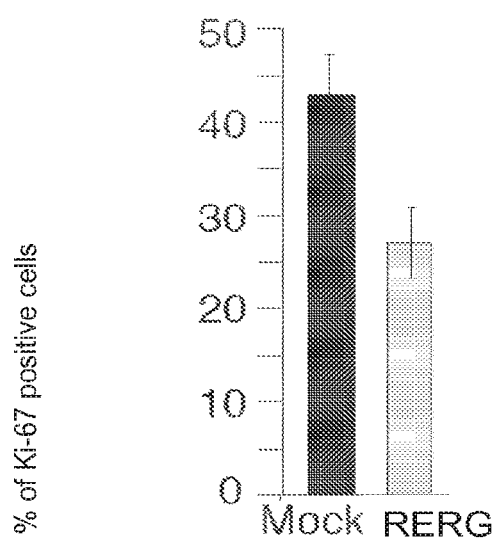
Figure 3A:
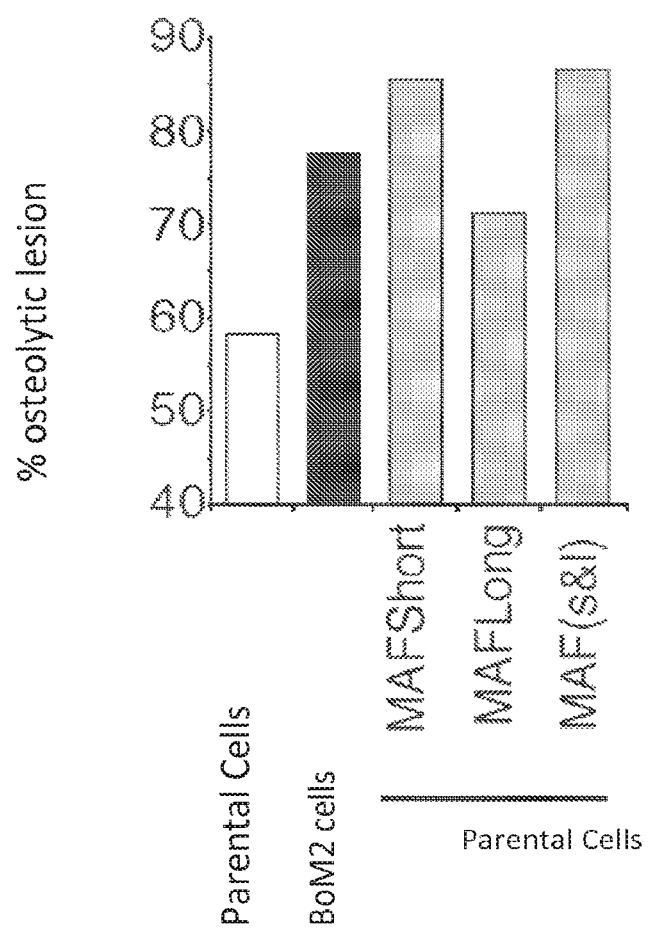
FIG. 3A-F. (3A) Quantification using X-rays of the number of osteolytic bone metastases in mice injected with different cell types featuring different MAF levels. (3B) Quantification of the number of TRAP (tartrate-resistant alkaline phosphatase) cells, osteoclast marker, on the perimeter of metastatic lesions in lesions caused by cells featuring different MAF levels. (3C) Validation using quantitative RT-PCR of the relationship between the MAF expression and the PTHLH gene. (3D) Experiment on the differentiation of in vitroosteoclasts using one stem-cells. The differentiation process is conducted in the presence of the RANK ligand, G-CSF and medium from the different populations. Parental cells, parental cells which express short and long MAF isoforms and the latter cells in the presence of a peptide neutralizing the PTHLH function. (3E) A bone metastasis experiment in an experimental metastasis model in mice. Cells are injected with or without c-MAF expression, and, in the latter case, a group with an intraperitoneal antagonist PTHLH peptide inoculation twice a day (12 micrograms/mouse/day) to the left ventricle of the mouse, whereby the appearance and growth of the lesion to the bone is quantified. The graph on the left illustrates the strength of the endpoint signal. The graph on the right specifies the number of osteolytic lesions in each group. (3F) On the left, a panel showing an X-ray image (the white area shows the osteolytic lesion, missing bone) and a TRAP+ stain (osteoclast marker) in bones representative of the groups described in (3E). The white triangles indicate the osteoclasts. On the right, a panel showing the area of the TRAP signal standardized by the perimeter.
Figure 3B:
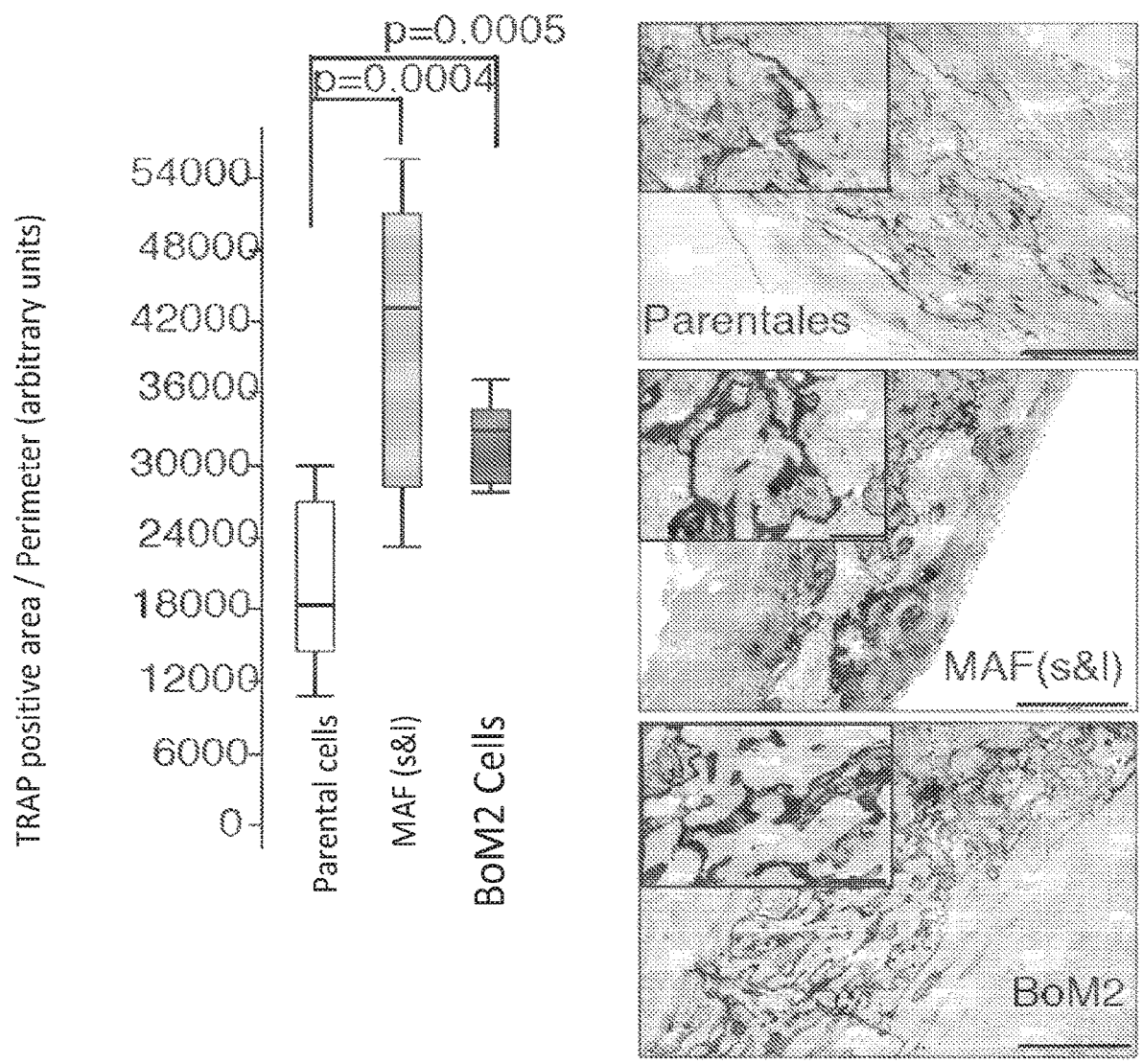
Figure 3C:
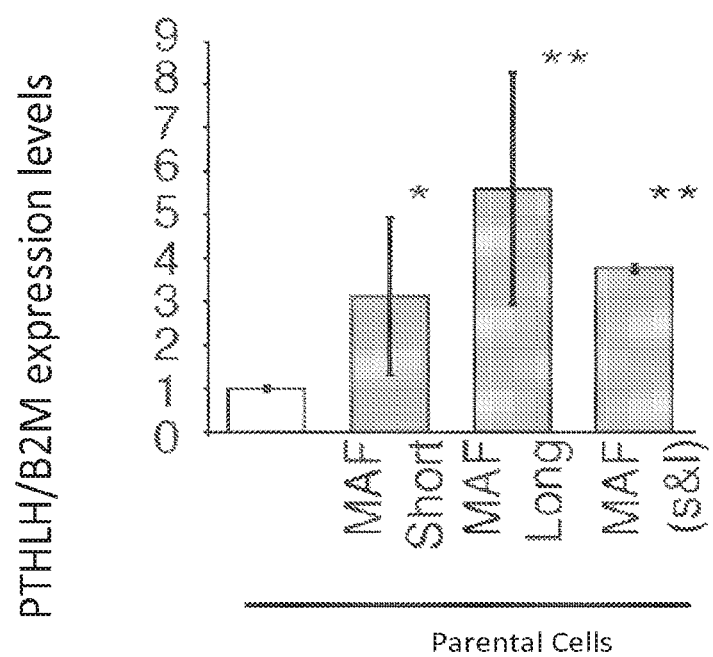
Figure 3D:
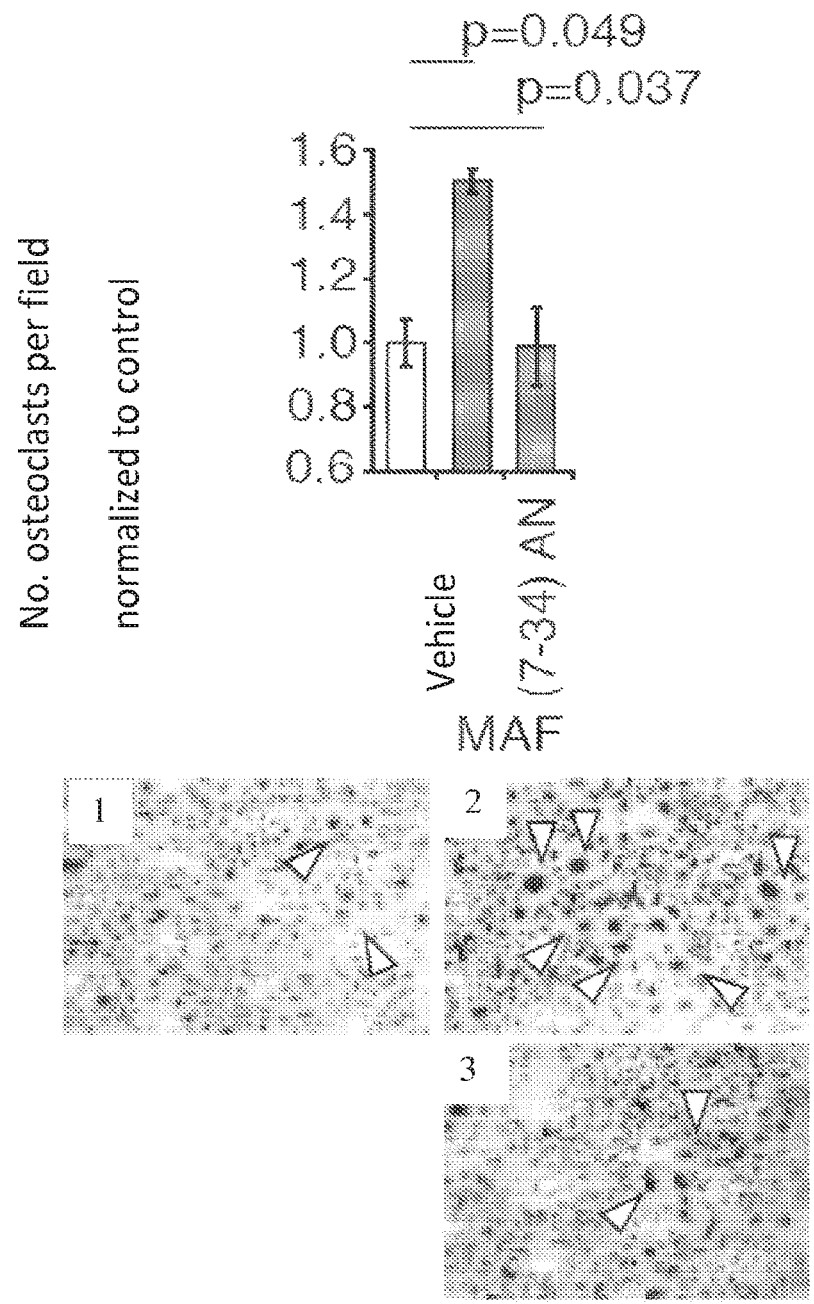
Figure 3E:
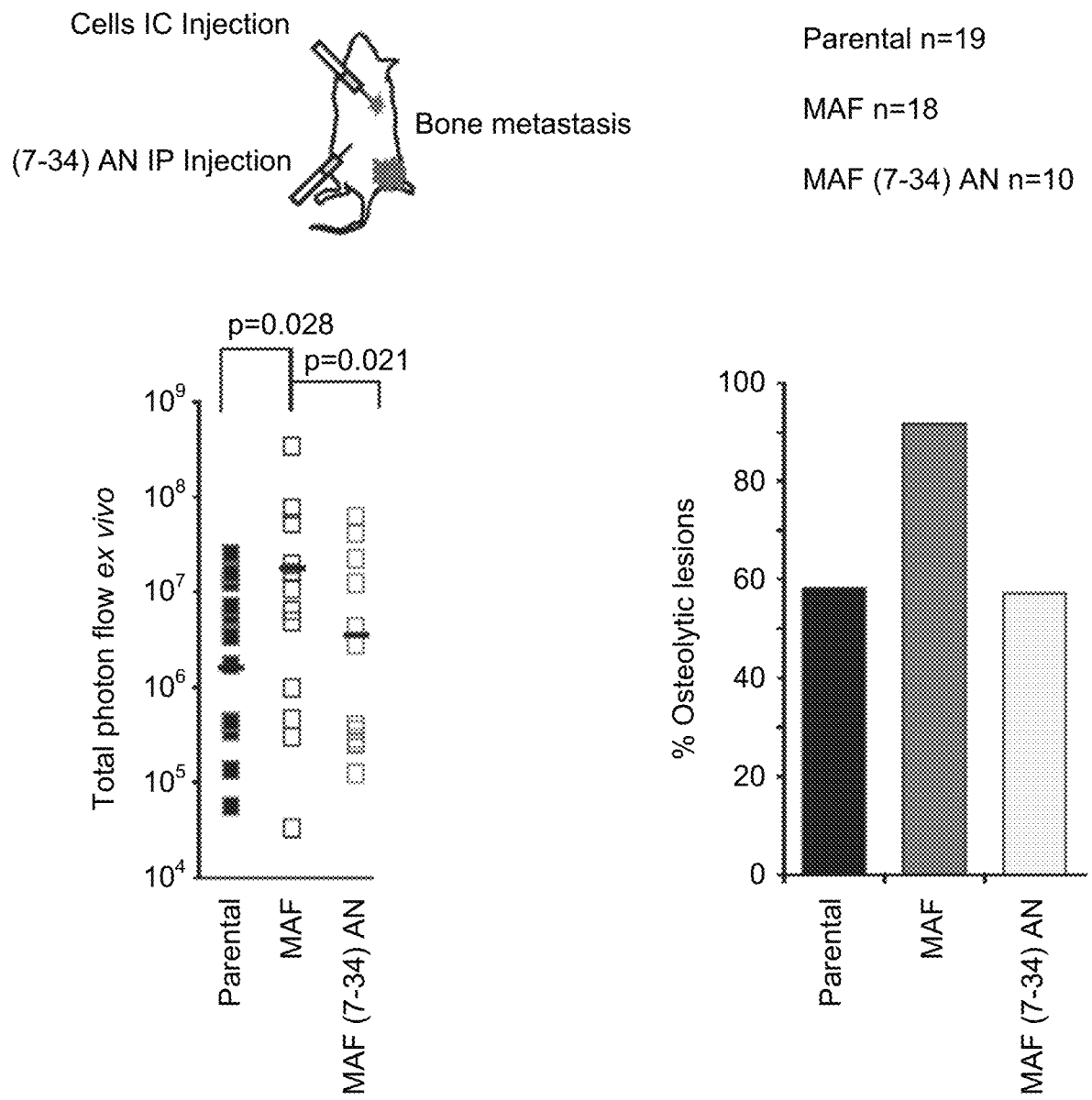
Figure 3F:
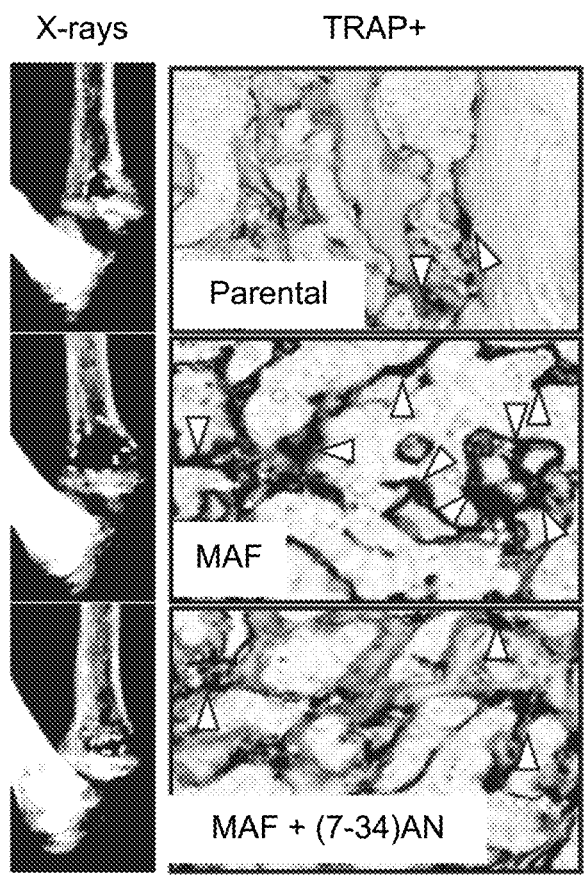
Figure 3F:
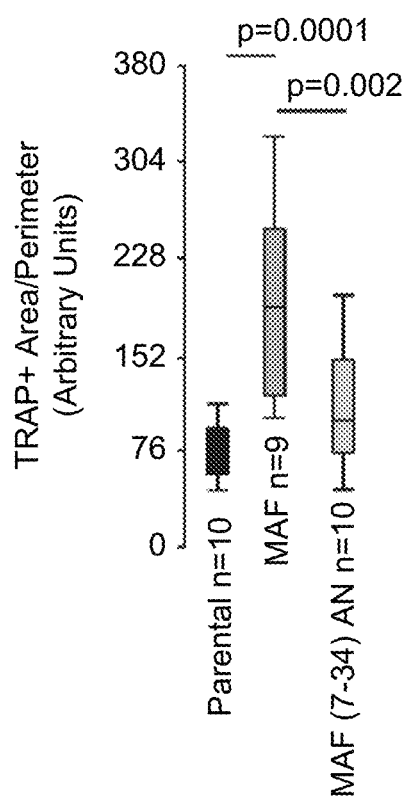
Figure 4A:
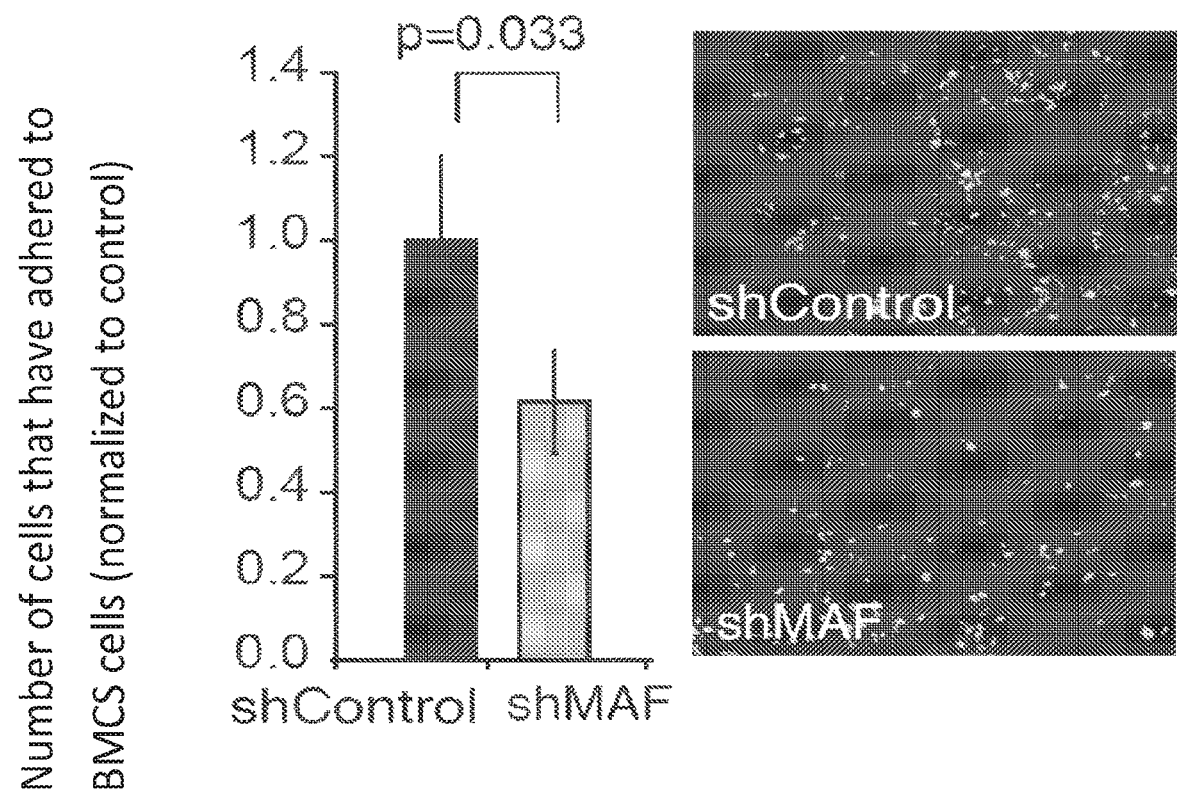
FIG. 4A-D. (4A) Quantification by fluorescence of the number of cells expressing high (shControl) or reduced (shMAF) c-MAF gene levels which bind to a layer of cells derived from bone marrow (BMSC). (4B) Quantification by fluorescence of the number of cells expressing high (shControl) or reduced (shMAF #1 or #2) c-MAF gene levels which bind to a layer of extracellular lung matrix protein such as fibronectin. This case reveals the opposite effect to that of bone marrow cells. (4C) Panel of genes whose expression changes with the changes in c-MAF expression and which have been validated by RT-PCR. Among which is PODXL, a gene which expresses a protein from the selectin family (glycoproteins) capable of participating in transitional and weak intercellular binding processes. (4D) Functional validation of the PODXL gene as responsible for cancerous breast cells expressing c-MAF binding with bone marrow cells. Comparison with the competitive effect of a neutral (RGES) or blocking (RGDS) peptide of integrin-mediated adhesions. This process is specific as it is not reproduced in human umbilical vein endothelial cells (HUVEC)
Figure 4B:
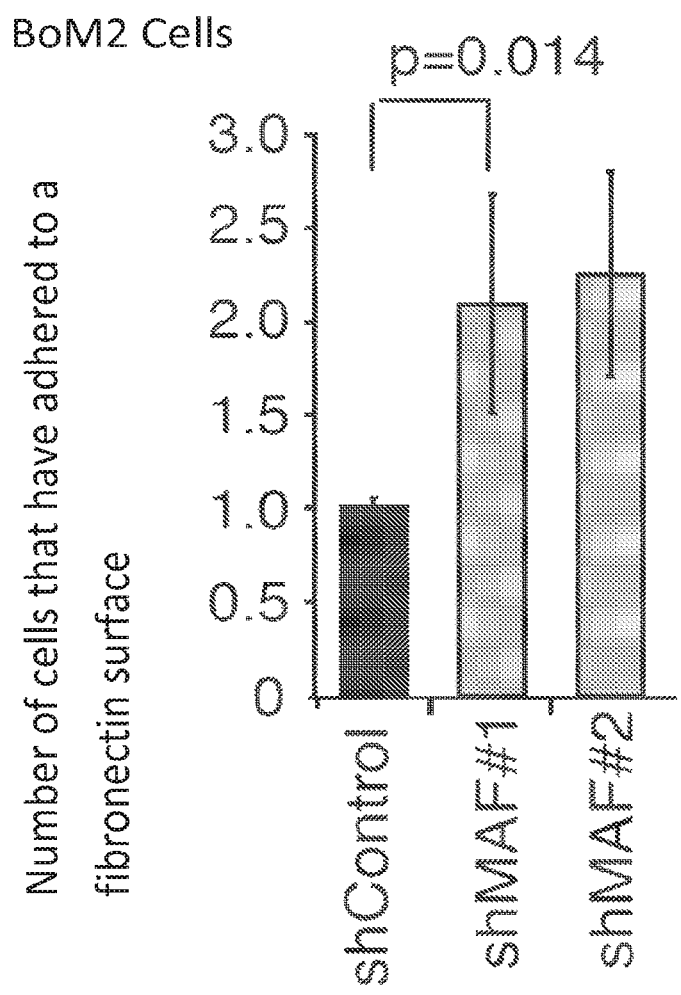
Figure 4C:
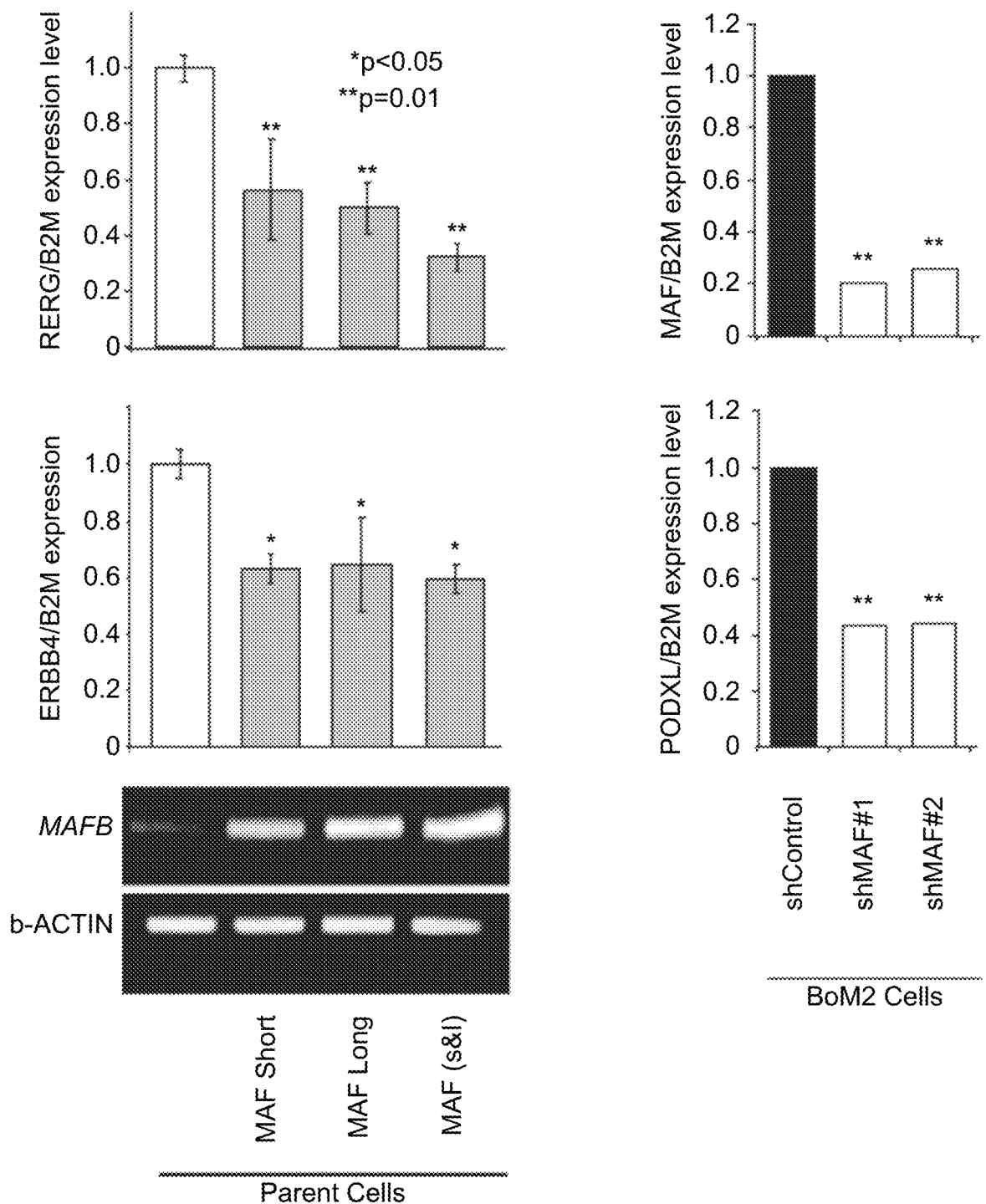
Figure 4D:
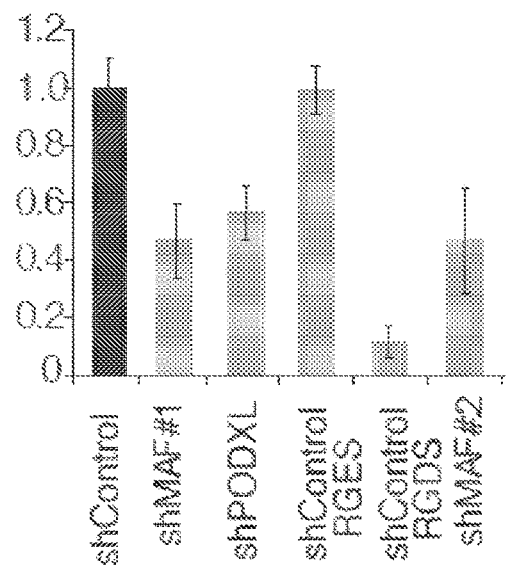
Figure 4D:
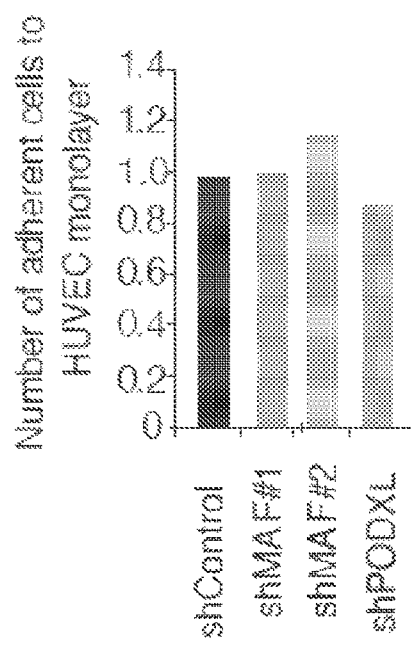

An analysis was performed, the purpose of which was to select genes that express in a differential manner in cells derived from a single ER+ breast cancer cell line in response to changes in the levels of expression of c-MAF (Table 1, FIG. 1B). The genes and functions that were determinative of the bone metastasis program mediated by c-MAF were selected following the below criteria:
  i) Genes the expression of which in primary tumors is significantly correlated with the expression of c-MAF.
  ii) Genes whose expression is modified with the expression of c-MAF, either when c-MAF is over-expressed (long or short isoform) in MCF7 cells, or when the expression of c-MAF in highly metastatic bone cells derived from MCF7 expressing c-MAF is reduced, and
  iii) Genes that are correlated to the expression of MAF in primary tumors and in one of the mentioned cellular conditions in ii) are considered members of the bone metastatic program mediated by c-MAF.

Based on these criteria, genes whose level of expression is correlated with the level of expression of c-MAF were identified and how its variations in the levels of expression were related to the expression of c-MAF in ER+ primary breast cancer tumors was determined (Table 1).

Example 2

The therapeutic value and prognostic value of genes enriched for the development of bone metastasis.

The genes enriched in bone metastasis through the experimental system for the selection of metastatic cell populations developed here were evaluated vis-a-vis two different databases containing the expression profiles and the clinical records of 560 primary breast cancer tumors and 58 metastases from patients suffering from breast cancer. These tumors are representative of all of the sub-types of breast cancer and localizations of metastases. Both databases and the related clinical records are available to the public (GSE 2603, 2034, 12276 and 14020).

The gene expression in ER+ primary tumors of the genes taken from bone metastases demonstrated a significant correlation with a recurrence in bones and was also correlated with metastasis to bone (FIG. 1A) but not with metastasis to other tissues (FIG. 1B).

Example 3

In Vivo Functional Validation of the Members of the Program for Bone Metastasis Mediated by c-MAF: PTHLH Gene The metastatic PTHLH gene, positive during prior analysis and directly correlated with the expression of c-MAF (Table 1 and FIG. 3), was functionally validated in a metastatic colonization trial in bones in an xenograft experimental model of breast cancer metastasis in mice. The standard approximations/approaches to validate the candidate gene to direct the process of metastasis were the samples of the loss of PTHLH function in low-metastatic cells that express c-MAF. The expression of the c-MAF gene was induced in cells that were moderately metastatic in bone, in vivo, MCF7, that present low levels of expression of the gene, c-MAF. The overexpression of c-MAF was responsible for the increase in the endogenous levels of the PTHLH gene (FIG. 3). In this context the activity of the cytokine PTHLH was then blocked using an antagonist peptide (FIG. 3).

In the process for the transduction of the gene, lentiviral systems were used to infect and introduce the expression of the candidate gene in the tumor cells. The functions facilitating the metastasis of the c-MAF gene and its effector PTHLH were determined using monitoring technology incorporating bioluminescent imaging of the metastatic cells inoculated in mice intra-cardially. In all cases, the corresponding control cells infected with empty lentiviral vectors were injected into a parallel cohort in immuno-deficient rats for comparative purposes. (FIG. 3.) The capacity for the formation of osteolytic lesions was evaluated, as was the differentiation of osteoclasts in the metastatic lesions in vivo and the causal function of PTHLH in this process (FIG. 3).

The experiments of gain of function as well as the data related to clinical correlation made it possible to functionally validate the role of the PTHLH as a prognostic marker and a target gene effectively causational in processes of bone metastasis in ER+ breast cancer cases and as part of the program of bone metastasis mediated by the c-MAF gene.

Example 4

In Vivo Functional Validation of the Members of the Bone Metastasis Program Mediated by the c-MAF Gene; RERG Gene The metastasis suppressor gene RERG is implicated in proliferation. The performed prior analysis demonstrated that the expression of the RERG gene is inversely correlated with the expression of c-MAF (Table 2 and FIG. 2). The RERG gene was functionally validated in a metastatic colonization trial in bones in a xenograft experimental model of breast cancer metastasis in rats.

The implication of the RERG gene in metastasis was validated through a trial of functional gain in highly metastatic cells. The expression of RERG in highly metastatic cells in bone selected in vivo, BoM2 was induced, the same which presented elevated levels of expression of the c-MAF gene, responsible for the suppression of the endogenous levels of RERG (FIG. 2).

In the gene transduction process, lentiviral systems were used in order to infect and introduce the expression of the candidate gene in tumor cells. The functions that facilitate the metastasis of the suppression of RERG were determined using bioluminescent imaging techniques to monitor metastatic cells inoculated intracardially in mice. In all cases, the corresponding control cells infected with empty lentiviral vectors were injected into a parallel cohort in immunodeficient rats for comparative purposes. (FIG. 2.) The loss of c-MAF is associated with greater RERG expression and a decrease in the proliferation of the metastatic cells (FIG. 2). The overexpression of RERG in cells that are highly metastatic to bone (BoM2), which express high levels of c-MAF, led to a reduction in the capacity of those cells to colonize the bone (FIG. 2). This reduction was accompanied by a reduction in the rates of proliferation as measured by the marker Ki-67 (FIG. 2).

The experiments of gain of function in the context of c-MAF overexpression as well as the data related to clinical correlation made it possible to functionally validate the role of RERG as a prognostic marker and a target gene effectively causational in processes of bone metastasis in ER+ breast cancer cases and as part of the program of bone metastasis mediated by the c-MAF gene.

Example 5

In Vivo Functional Validation of the Members of the Program of Metastasis in Bone Mediated by c-MAF: PODXL Gene The PODXL metastatic gene, positive in the prior analysis and directly correlated to the expression of c-MAF (Table 1 and FIG. 4), was functionally validated in a trial of adhesion to cells derived from bone marrow in an experimental model based on purified bone marrow cells from mice. This adhesion process is specific for bone cells given that if it is repeated using endothelial cells or proteins from the extracellular matrix of the lung, taken from the vasculature, neither a greater adhesion in the presence of PODXL nor high levels of c-MAF are observed, but rather quite the opposite (FIG. 4). The standard approximations to validate the candidate gene to direct the metastasis process were the trials of loss of function in highly metastatic cells, in either bone or endothelial cells. The expression of the PODXL gene was reduced in highly-metastatic cells in bone, in vivo, MCF7, presenting high levels of expression of the c-MAF gene responsible for the increase of the endogenous levels of the PODXL gene.

In the process of transduction of the interference RNA, lentiviral systems to infect and introduce the expression of the RNAi candidate in the tumor cells were used. The functions that facilitated the metastasis of the PODXL gene were determined using the fluorescent imaging techniques (technology) applied to the metastatic cells on a layer of endothelial cells or cells derived from bone marrow. In all cases, the corresponding control cells infected with empty lentiviral vectors were used for comparative purposes. (FIG. 4). It was evaluated whether this process is associated with the activity of integrins using two peptides, RGES and RGDS, the first which is not bound to the integrins, while the second competes with these and prevents cellular adhesion. In conclusion, the causal function of PODXL in this process was validated potentially through the interaction via integrins (FIG. 4).

The experiments related to loss of function as well as the correlative data allow for the functional validation of the role of PODXL as a prognostic marker and a target gene that is causal in the process of metastasis of ER+ breast cancer into bone and as part of the program of metastasis to bone as mediated by the c-MAF gene.

The terms "Sequence listing" and "Artificial sequence" from the list of sequences are translated, respectively, as "Sequence listing" and "Artificial sequence". (sic)

The invention claimed is:

1. A method for the treatment and/or prevention of breast cancer metastasis in a subject comprising
    (i) quantifying an expression level of c-MAF in a breast cancer tumor sample of the subject,
    (ii) quantifying an expression level of a gene whose expression level is increased in response to an increase in the level of expression of c-MAF in a breast cancer tumor sample of the subject,
    (iii) determining that the subject has an increased expression level of c-MAF and of the gene whose expression level is increased in response to an increase in the level of expression of c-MAF,
    (iv) administering to the subject an agent capable of inhibiting the activity of the expression product of the gene whose expression level is increased in response to an increase in the level of c-MAF expression,
    wherein the agent capable of inhibiting the activity of the expression product of the gene whose expression level is increased in response to an increase in the level of c-MAF expression is an inhibitor antibody specific for an expression product of the gene whose expression level is increased in response to an increase in the level of expression of c-MAF, and
    wherein the gene whose expression level is increased in response to an increase in the level of expression of c-MAF is CD36.

2. The method of claim 1, wherein the breast cancer is ER+ cancer or triple negative cancer.

3. The method of claim 1, wherein the metastasis is bone metastasis.

4. The method of claim 3, wherein the bone metastasis is osteolytic bone metastasis.

5. The method of claim 1, wherein the increase in the level of c-MAF expression is an increase in the level of expression of the short isoform of c-MAF.

6. The method of claim 1, wherein the increase in the level of c-MAF expression is an increase in the level of expression of the long isoform of c-MAF.

7. The method of claim 1, wherein the subject is human.

8. The method of claim 1, wherein quantifying the expression level of the gene whose expression level is increased in response to an increase in the level of expression of c-MAF in the breast cancer tumor sample of the subject occurs before quantifying the expression level of c-MAF in the breast cancer tumor sample of the subject.

* * * * *

SEQUENCE LISTING

```
<160> NUMBER OF SEQ ID NOS: 8

<210> SEQ ID NO 1
<211> LENGTH: 19
<212> TYPE: RNA
<213> ORGANISM: Artificial Sequence
<220> FEATURE:
<223> OTHER INFORMATION: ARNip specific for c-MAF

<400> SEQUENCE: 1
acggcucgag cagcgacaa                                                19

<210> SEQ ID NO 2
<211> LENGTH: 19
<212> TYPE: RNA
<213> ORGANISM: Artificial Sequence
<220> FEATURE:
<223> OTHER INFORMATION: ARNip specific for c-MAF

<400> SEQUENCE: 2
cuuaccagug uguucacaa                                                19
```

```
<210> SEQ ID NO 3
<211> LENGTH: 20
<212> TYPE: RNA
<213> ORGANISM: Artificial Sequence
<220> FEATURE:
<223> OTHER INFORMATION: ARNip specific for c-MAF

<400> SEQUENCE: 3
uggaagacua cuacuggaug                                        20

<210> SEQ ID NO 4
<211> LENGTH: 20
<212> TYPE: RNA
<213> ORGANISM: Artificial Sequence
<220> FEATURE:
<223> OTHER INFORMATION: ARNip specific for c-MAF

<400> SEQUENCE: 4
auuugcaguc auggagaacc                                        20

<210> SEQ ID NO 5
<211> LENGTH: 20
<212> TYPE: RNA
<213> ORGANISM: Artificial Sequence
<220> FEATURE:
<223> OTHER INFORMATION: ARNip specific for c-MAF

<400> SEQUENCE: 5
caaggagaaa uacgagaagu                                        20

<210> SEQ ID NO 6
<211> LENGTH: 20
<212> TYPE: RNA
<213> ORGANISM: Artificial Sequence
<220> FEATURE:
<223> OTHER INFORMATION: ARNip specific for c-MAF

<400> SEQUENCE: 6
acaaggagaa auacgagaag                                        20

<210> SEQ ID NO 7
<211> LENGTH: 20
<212> TYPE: RNA
<213> ORGANISM: Artificial Sequence
<220> FEATURE:
<223> OTHER INFORMATION: ARNip specific for c-MAF

<400> SEQUENCE: 7
accuggaaga cuacuacugg                                        20

<210> SEQ ID NO 8
<211> LENGTH: 28
<212> TYPE: PRT
<213> ORGANISM: Artificial Sequence
<220> FEATURE:
<223> OTHER INFORMATION: hPTHrP

<400> SEQUENCE: 8

Leu Leu His Asp Lys Gly Lys Ser Ile Gln Asp Leu Arg Arg Arg Phe
1               5                   10                  15

Phe Leu His His Leu Ile Ala Glu Ile His Thr Ala
            20                  25
```